United States Patent
King-Underwood et al.

(10) Patent No.: US 9,024,041 B2
(45) Date of Patent: *May 5, 2015

(54) P38 MAP KINASE INHIBITORS

(75) Inventors: John King-Underwood, Pendock (GB);
Peter John Murray, London (GB);
Jonathan Gareth Williams, Nottingham (GB); Ildiko Buck, Nottingham (GB);
Stuart Thomas Onions, Nottingham (GB)

(73) Assignee: Respivert Ltd., Buckinghamshire (GB)

(*) Notice: Subject to any disclaimer, the term of this patent is extended or adjusted under 35 U.S.C. 154(b) by 0 days.

This patent is subject to a terminal disclaimer.

(21) Appl. No.: 13/639,959

(22) PCT Filed: Apr. 8, 2011

(86) PCT No.: PCT/GB2011/050706
§ 371 (c)(1),
(2), (4) Date: Oct. 8, 2012

(87) PCT Pub. No.: WO2011/124930
PCT Pub. Date: Oct. 13, 2011

(65) Prior Publication Data
US 2013/0040962 A1    Feb. 14, 2013

(30) Foreign Application Priority Data
Apr. 8, 2010 (EP) .................................. 10159380

(51) Int. Cl.
| | |
|---|---|
| C07D 231/10 | (2006.01) |
| A61K 31/415 | (2006.01) |
| C07D 401/12 | (2006.01) |
| C07D 401/14 | (2006.01) |
| C07D 405/14 | (2006.01) |
| C07D 409/14 | (2006.01) |

(52) U.S. Cl.
CPC ............ *C07D 401/12* (2013.01); *C07D 401/14* (2013.01); *C07D 405/14* (2013.01); *C07D 409/14* (2013.01)

(58) Field of Classification Search
None
See application file for complete search history.

(56) References Cited

U.S. PATENT DOCUMENTS

| | | | |
|---|---|---|---|
| 8,293,748 B2 * | 10/2012 | Ito et al. .................... 514/253.09 |
| 8,293,771 B2 * | 10/2012 | Ito et al. .......................... 514/340 |
| 8,299,073 B2 * | 10/2012 | Ito et al. ........................ 514/236.5 |
| 8,299,074 B2 * | 10/2012 | Ito et al. ........................ 514/236.5 |
| 2003/0232865 A1 | 12/2003 | Cirillo et al. | |
| 2006/0035922 A1 | 2/2006 | Mathias et al. | |
| 2008/0113967 A1 | 5/2008 | Flynn et al. | |
| 2011/0212962 A1 * | 9/2011 | Ito et al. ....................... 514/236.5 |
| 2011/0269800 A1 * | 11/2011 | Ito et al. .......................... 514/341 |
| 2011/0294812 A1 * | 12/2011 | Ito et al. ....................... 514/236.5 |
| 2011/0312963 A1 * | 12/2011 | Ito et al. ....................... 514/236.5 |

FOREIGN PATENT DOCUMENTS

| | | |
|---|---|---|
| WO | WO 00/43384 A1 | 7/2000 |
| WO | 2000/55139 A2 | 9/2000 |
| WO | WO 2004/100946 A1 | 11/2004 |
| WO | 2005/110994 A2 | 11/2005 |
| WO | 2005/110994 A3 | 11/2005 |
| WO | 2006/071940 A2 | 7/2006 |
| WO | WO 2006/072589 A2 | 7/2006 |
| WO | 2007/064872 A2 | 6/2007 |
| WO | 2007/087448 A1 | 8/2007 |
| WO | 2007/089512 A1 | 8/2007 |
| WO | 2007/091176 A1 | 8/2007 |
| WO | 2007/053394 A1 | 10/2007 |
| WO | 2008/121666 A1 | 10/2008 |
| WO | 2008/125014 A1 | 10/2008 |
| WO | 2009/077766 A8 | 9/2009 |
| WO | 2009/117080 A2 | 9/2009 |
| WO | WO 2010/038085 A2 | 4/2010 |
| WO | WO 2010/038086 A2 | 4/2010 |

(Continued)

OTHER PUBLICATIONS

"Chemical Structures of Compounds Disclosed in Ito et al. '812, '963, '962, and '800," retrieved from CAPlus (Nov. 2013).*
"Bioisosterism" in The Organic Chemistry of Drug Design and Drug Action by Silverman, Academic Press (San Diego), pp. 19-23 (1992).*
International Search Report and Written Opinion for PCT/GB2011/050706, Dated Aug. 19, 2011.

(Continued)

*Primary Examiner* — Theodore R West
(74) *Attorney, Agent, or Firm* — Brian C. Carey

(57) ABSTRACT

There is provided a compound of formula (I): wherein: J represents (A): or (B): compositions comprising same, processes for preparing said compounds and use thereof in treatment, particularly in the treatment of inflammatory disease, such as asthma, COPD and 15 rheumatoid arthritis.

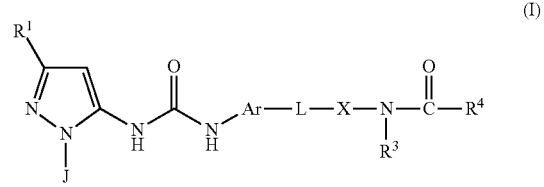

(I)

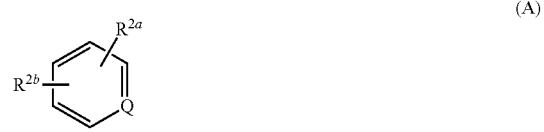

(A)

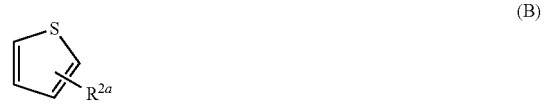

(B)

28 Claims, No Drawings

(56) References Cited

FOREIGN PATENT DOCUMENTS

| WO | WO 2010/067130 A1 | 6/2010 |
|----|-------------------|--------|
| WO | WO 2010/067131 A1 | 6/2010 |
| WO | WO 2010/112936 A1 | 10/2010 |
| WO | WO 2011/070369 A1 | 6/2011 |
| WO | WO 2011/121366 A1 | 10/2011 |
| WO | WO 2011/124923 A2 | 10/2011 |

OTHER PUBLICATIONS

Chemical Abstracts, Database accession No. 1124306-29-1, Mar. 20, 2009.

Karcher et al., "Successful structure-based design of recent p38 MAP kinase inhibitors", Current Topics in Medicinal Chemistry (2009) 655-676 vol. 9 (7), Bentham Science, NL.

Moss et al., "New modifications to the area of pyrazole-naphthyl urea based p38 MAP kinase inhibitors that bind to the adenine/ATP site", Bioorganic & Medicinal Chemistry Letters (2007) 4242-4247 vol. 17 (15), Elsevier Science, GB.

Simard et al., "Development of a fluorescent-tagged kinase assay system for the detection and characterization of allosteric kinase inhibitors", Journal of the American Chemical Society (2009) 13286-13296 vol. 131 (37), American Chemical Society, US.

Shmueli, O. et al., "GeneNote: whole genome expression profiles in normal human tissues", Comptes Rendus Biologies, 2003, 326(10-11):1067-1072/Genecard.

Smith, S. et al., "Inhibitory effect of p38 mitogen-activated protein kinase inhibitors on cytokine releases from human macrophages", J. Br. J. Pharmacol., 2006, 149:393-404.

Hale, K. K. et al., "Differential Expression and Activation of p38 Mitogen-Activated Protein Kinase $\alpha$, $\beta$, $\gamma$ and $\delta$ in Inflammatory Cell Lineages", J. Immunol., 1999, 162(7):4246-52.

Wang, X. S. et al., "Molecular Cloning and Characterization of a Novel p38 Mitogen-activated Protein Kinase", J. Biol. Chem., 1997, 272(38):23668-23674.

Court, N. W. et al., "Cardiac Expression and Subcellular Localization of the p38 Mitogen-activated Protein Kinase Member, Stress-activated Protein Kinase-3 (SAPK3)", J. Mol. Cell. Cardiol., 2002, 34(4):413-26.

Mertens, S. et al., "SAP kinase-3, a new member of the family of mammalian stress-activated protein kinases", FEBS Lett., 1996, 383(3):273-6.

Kuma, Y. "BIRB796 inhibits all p38 MAPK isoforms in vitro and in vivo", J. Biol. Chem., 2005, 280:19472-19479.

Underwood D.C. et al., "SB239063, a p38 MAPK inhibitor, reduces neutrophilia, inflammatory cytokines, MMP-9, and fibrosis in lung", Am. J. Physiol. Lung Cell. Mol. Physiol., 2000, 279:895-902.

Nath, P. et al., "Importance of p38 mitogen-activated protein kinase pathway in allergic airway remodeling and bronchial hyper-responsiveness", Eur. J Pharmacol., 2006, 544:160-167.

Irusen, E. et al., "p38 Mitogen-activated protein kinase-induced glucocorticoid receptor phosphorylation reduces its activity: Role in steroid-insensitive asthma", J. Allergy Clin. Immunol., 2002, 109:649-657.

Lee et al., "MAP Kinase p38 Inhibitors: Clinical Results and an Intimate Look at Their Interactions with p38$\alpha$ Protein", Current Med. Chem., 2005, 12:2979-2994.

Regan, J. et al.; Structure-Activity Relationships of the p38$\alpha$ MAP Kinase Inhibitor 1-(5-tert-Butyl-2-p-tolyl-2H-pyrazol-3-2H-pryazol-3-yl)-3-(4-(2-morpholin-4-yl-ethoxy)naphthalene-1-7-yflurea.2-p-tolyl-2H-pyrazol-3-2H-pryazol-3-yl)-3-(4-(2-morpholin-4-yl-ethoxy)naphthalene-1-7-yl)urea (BIRB 795) Journal of Medicinal Chemistry., 2003, 46, 4676-4686.

\* cited by examiner

P38 MAP KINASE INHIBITORS

This application is a National Stage application under 35 U.S.C. 371 of PCT International Application No. PCT/GB2011/050706, filed Apr. 8, 2011, which claims priority from European patent application number EP 10159380.4, filed Apr. 8, 2010, the contents of which are hereby incorporated by reference in their entirety.

FIELD OF THE INVENTION

The invention relates to compounds which are inhibitors of p38 mitogen-activated protein kinase enzymes (referred to herein as p38 MAP kinase inhibitors), for example the alpha and gamma kinase sub-types thereof, and their use in therapy, including in pharmaceutical combinations, especially in the treatment of inflammatory diseases, including inflammatory diseases of the lung, such as COPD.

BACKGROUND OF THE INVENTION

Four p38 MAPK isoforms (alpha, beta, gamma and delta respectively) have been identified, each displaying a tissue-specific expression pattern. The p38 MAPK alpha and beta isoforms are ubiquitously expressed throughout the body and are found in many different cell types. The p38 MAPK alpha and beta isoforms are inhibited by certain known small molecule p38 MAPK inhibitors. Earlier generations of compounds were highly toxic due to the ubiquitous expression pattern of these isoforms and off-target effects of the compounds. More recent inhibitors are improved to be highly selective for p38 MAPK alpha and beta isoforms and have a wider safety margin.

Less is known about the p38 MAPK gamma and delta isoforms. These isoforms are expressed in specific tissues/cells (unlike the p38 alpha and p38 beta isoforms). The p38 MAPK-delta isoform is expressed more in the pancreas, testes, lung, small intestine and kidney. It is also abundant in macrophages and detectable in neutrophils, CD4+ T cells and endothelial cells (Shmueli, O. et al., *Comptes Rendus Biologies* 326(10-11):1067-1072, (2003)/Genecard; Smith, S. J. *Br. J. Pharmacol.*, 2006, 149:393-404; Hale, K. K., *J. Immunol.*, 1999, 162(7):4246-52; Wang, X. S. et al., *J. Biol. Chem.*, 1997, 272(38):23668-23674.) Very little is known about the expression of p38 MAPK gamma although it is expressed more highly in brain, skeletal muscle and heart, as well as in lymphocytes and macrophages. (Shmueli, O. et al., *Comptes Rendus Biologies*, 2003, 326(10-11):1067-1072, (2003)/Genecard; Hale, K. K., *J. Immunol.*, 1999, 162(7):4246-52: Court, N. W. et al., *J. Mol. Cell. Cardiol.*, 2002, 34(4):413-26; Mertens, S. et al., *FEBS Lett.*, 1996, 383(3):273-6.)

Selective small molecule inhibitors of p38 MAPK-gamma and p38 MAPK-delta are not currently available, although one existing compound, BIRB 796, is known to have pan-isoform inhibitory activity. The p38 MAPK gamma and delta isoform inhibition is observed at higher concentrations of the compound than those required to inhibit p38 MAPK alpha and p38 beta (Kuma, Y. *J. Biol. Chem.*, 2005, 280:19472-19479). BIRB 796 also impaired the phosphorylation of p38 MAPKs or JNKs by the upstream kinase MKK6 or MKK4. Kuma discussed the possibility that the conformational change caused by the binding of the inhibitor to the MAPK protein may affect the structure of both its phosphorylation site and the docking site for the upstream activator, therefore impairing the phosphorylation of p38 MAPKs or JNKs.

p38 MAP kinase is believed to play a pivotal role in many of the signalling pathways that are involved in initiating and maintaining chronic, persistent inflammation in human disease, for example, in severe asthma and COPD. There is now abundant literature which demonstrates that p38 MAP kinase is activated by a range of pro-inflammatory cytokines and that its activation results in the recruitment and release of further pro-inflammatory cytokines. Indeed, data from some clinical studies demonstrate beneficial changes in disease activity in patients during treatment with p38 MAP kinase inhibitors. For instance Smith, S. J. *Br. J. Pharmacol.*, 2006, 149:393-404 describes the inhibitory effect of p38 MAP kinase inhibitors on TNFα (but not IL-8) release from human PBMCs. Use of inhibitors of p38 MAP kinase in the treatment of chronic obstructive pulmonary disease (COPD) is proposed. Small molecule inhibitors targeted to p38 MAPKα/β have proved to be effective in reducing various parameters of inflammation in cells and tissues obtained from patients with COPD, who are generally corticosteroid insensitive, (Smith, S. J. *Br. J. Pharmacol.*, 2006, 149:393-404) and in vivo animal models (Underwood, D. C. et al. *Am. J. Physiol.*, 2000, 279:L895-902; Nath, P. et al., *Eur. J. Pharmacol.*, 2006, 544:160-167). Irusen and colleagues also suggested the possibility of involvement of p38 MAPKα/β on corticosteroid insensitivity via reduction of binding affinity of glucocorticoid receptor (GR) in nuclei (Irusen, E. et al., *J. Allergy Clin. Immunol.*, 2002, 109:649-657). Clinical experience with a range of p38 MAP kinase inhibitors, including AMG548, BIRB 796, VX702, SCIO469 and SCIO323 has been described (Lee M. R. and Dominguez, C. *Current Med. Chem.*, 2005, 12:2979-2994).

COPD is a condition in which the underlying inflammation is reported to be substantially resistant to the anti-inflammatory effects of inhaled corticosteroids. Consequently, a superior strategy for treating COPD would be to develop an intervention which has both inherent anti-inflammatory effects and the ability to increase the sensitivity of the lung tissues of COPD patients to inhaled corticosteroids. The recent publication of Mercado et al (2007; *American Thoracic Society Abstract A56*) demonstrates that silencing p38 gamma has the potential to restore sensitivity to corticosteroids. Thus there may be a "two pronged" benefit to the use of a p38 MAP kinase inhibitor for the treatment of COPD and severe asthma.

However, the major obstacle hindering the utility of p38 MAP kinase inhibitors in the treatment of human chronic inflammatory diseases has been the toxicity observed in patients. This has been sufficiently severe to result in the withdrawal from clinical development of many of the compounds progressed, including all those specially mentioned above.

There remains a need to identify and develop new compounds therapeutically useful as p38 MAP kinase inhibitors which have improved therapeutic potential, in particular which are more efficacious, longer acting and/or less toxic at the relevant therapeutic dose. An objective of the present invention is to provide compounds which inhibit p38 MAP kinase, for example with certain sub-type specificity, which show good anti-inflammatory potential, in particular suitable for use in therapy.

SUMMARY OF THE INVENTION

According to the invention, there is provided a compound of formula (I)

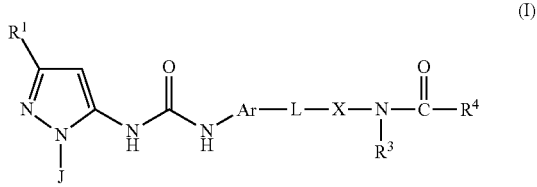

wherein:

J represents

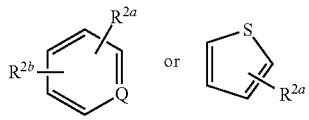

Ar is a naphthylene or phenyl ring either of which may be optionally substituted by one or more groups (e.g. 1, 2 or 3 groups) independently selected from $C_{1-6}$ alkyl, $C_{1-6}$ alkoxy, amino, $C_{1-4}$ mono alkyl amino and $C_{2-8}$ di-alkyl amino;

Q is N, or CH;

$R^1$ is H, phenyl, or a saturated or unsaturated branched or unbranched $C_{1-10}$ alkylene in the form of an acyclic or alicyclic chain wherein one or more carbons in the chain (for example 1 to 3, such as 1, 2 or 3 carbons) are optionally replaced by a heteroatom(s) independently selected from —O—, —N— and $S(O)_n$ and the chain is optionally substituted by:

one oxo group, and/or one or more halogen atoms (for example 1 to 6);

$R^{2a}$ is H, halo, saturated or unsaturated branched or unbranched $C_{1-8}$ alkylene chain, wherein one or more carbons (for example 1 to 3, such as 1, 2 or 3 carbons) are optionally replaced by a heteroatom(s) independently selected from —O—, —N— and/or $S(O)_m$ and the chain is optionally substituted by one or more halogen atoms (for example 1 to 6);

$R^{2b}$ is H, halo, $C_{1-6}$ alkoxy or $C_{1-6}$ alkyl optionally substituted by OH;

L is saturated or unsaturated branched or unbranched $C_{1-6}$ alkylene chain (such as a $C_{1-3}$ alkylene), wherein one or more carbons (for example 1 to 3, such as 1, 2 or 3 carbons) are optionally replaced by a heteroatom selected from —O— and/or S, and the chain is optionally substituted by one or two oxo groups (for example 1 or 2);

X is a pyridine or pyrimidine ring optionally substituted by $C_{1-3}$ alkyl, or $C_{1-3}$ haloalkyl;

$R^3$ is H or $C_{1-4}$ alkyl;

$R^4$ is selected from:

a) a saturated or unsaturated, branched or unbranched $C_{1-10}$ alkyl chain, wherein optionally at least one carbon (for example 1, 2 or 3 carbons, suitably 1 or 2, in particular 1 carbon) is replaced by a heteroatom independently selected from O, N, $S(O)_p$, wherein said chain is optionally, substituted by one or more groups (for example 1, 2 or 3 groups) independently selected from oxo, halogen, a $C_{6-10}$ aryl group, a 5 or 6 membered heteroaryl group, a 5 or 6 membered heterocyclyl group or a $C_{3-8}$ cycloalkyl group, each aryl, heteroaryl, heterocyclyl or cycloalkyl group bearing 0 to 3 substituents selected from halogen, hydroxyl, $C_{1-6}$ alkyl, $C_{1-6}$ alkoxy, $C_{1-6}$ haloalkyl, amino, $C_{1-4}$ mono or $C_{2-8}$ di-alkyl amino, $C_{1-4}$ mono or $C_{2-8}$ di-acyl amino, $S(O)q C_{1-6}$ alkyl, $C_{0-6}$ alkylC(O)$C_{1-6}$ alkyl or $C_{0-6}$ alkylC(O)N$C_{0-6}$ alkyl $C_{0-6}$ alkyl, $C_{0-6}$ alkylC(O)$C_{1-6}$ heteroalkyl, with the proviso that the atom linked directly to the carbonyl in —$NR^3C(O)$— is not an oxygen or a sulfur atom; and b) a $C_{0-8}$ alkyl-heterocycle wherein the heterocyclyl group has 5 or 6 members and comprises at least one heteroatom (for example 1, 2 or 3, suitably 1 or 2, in particular 1 heteroatom) selected from O, N, and S, and said heterocycle is optionally substituted by one, two or three groups independently selected from halogen, hydroxyl, $C_{1-6}$ alkyl, $C_{1-6}$ alkoxy, $C_{1-6}$ haloalkyl, amino, $C_{1-4}$ mono and $C_{2-8}$ di-alkyl amino, $C_{1-4}$ mono or $C_{2-8}$ di-acyl amino, $S(O)_q$ $C_{1-6}$ alkyl, $C_{0-6}$ alkylC(O)$C_{1-6}$ alkyl, $C_{0-6}$ alkylC(O)N$C_{0-6}$ alkyl $C_{0-6}$ alkyl or $C_{0-6}$ alkylC(O)$C_{0-6}$ heteroalkyl;

n is 0, 1 or 2;

m is 0, 1 or 2;

p is 0, 1 or 2;

q is 0, 1 or 2;

or a pharmaceutically acceptable salt thereof, including all stereoisomers, tautomers and isotopic derivatives thereof with the proviso that when:

L represents a saturated or unsaturated branched or unbranched $C_{1-8}$ alkylene chain wherein one or more carbons are optionally replaced by —O— and the chain is optionally substituted by one or more halogen atoms, and $R^1$ is $C_{1-6}$ alkyl optionally substituted by a hydroxyl group, and J represents:

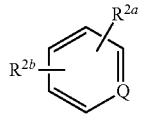

wherein Q is CH, and $R^{2a}$ is hydrogen, then $R^{2b}$ does not represent H or $C_{1-6}$ alkyl optionally substituted by a hydroxyl group.

DETAILED DESCRIPTION OF THE INVENTION

Alkyl as used herein refers to straight chain or branched chain alkyl, such as, without limitation, methyl, ethyl, n-propyl, iso-propyl, butyl, n-butyl and tert-butyl. In one embodiment alkyl refers to straight chain alkyl. Alkylene is to be interpreted in a similar manner to alkyl.

An acyclic chain refers to a chain without ring atoms. An alicyclic chain refers to an aliphatic chain with ring atoms.

Alkoxy as used herein refers to straight or branched chain alkoxy, for example methoxy, ethoxy, propoxy, butoxy. Alkoxy as employed herein also extends to embodiments in which the oxygen atom is located within the alkyl chain, for example —$C_{1-3}$ alkylO$C_{1-3}$ alkyl, such as —$CH_2CH_2OCH_3$ or —$CH_2OCH_3$. Thus in one embodiment the alkoxy is linked through carbon to the remainder of the molecule. In one embodiment the alkoxy is linked through oxygen to the remainder of the molecule, for example —$OC_{1-6}$ alkyl. In one embodiment the disclosure relates to a straight chain alkoxy.

Heteroalkyl as employed herein is intended to refer to a branched or straight chain alkyl wherein one or more, such as 1, 2 or 3 carbons are replaced by a heteroatom, selected from N, O or $S(O)_r$, wherein r represents 0, 1 or 2. The heteroatom may replace a primary, secondary or tertiary carbon, that is, for example, SH, OH or $NH_2$ for $CH_3$, or NH or O or $SO_2$ for —$CH_2$— or N for a —CH— or a branched tertiary carbon, as technically appropriate.

Haloalkyl as employed herein refers to alkyl groups having 1 to 6 halogen atoms, for example 1 to 5 halogens, including perhaloalkyl, in particular perchloroalkyl or perfluoroalkyl, more specifically —$CCl_3$, —$CF_2CF_3$ or $CF_3$.

$C_{1-4}$ mono acyl amino and $C_{2-8}$ di-acyl amino are intended to refer to —$NHC(O)C_{1-4}$ alkyl and to —$N(C=OC_{1-4}$ alkyl)$(C=OC_{1-4}$ alkyl) respectively.

$C_{1-4}$ mono alkyl amino and $C_{2-8}$ di-alkyl amino are intended to refer to —$NHC_{1-4}$ alkyl and to —$N(C_{1-4}$ alkyl)($C_{1-4}$ alkyl) respectively.

Aryl as used herein refers to, for example $C_{6-14}$ mono or polycyclic systems having from 1 to 3 rings wherein at least one ring is aromatic including phenyl, naphthyl, anthracenyl, 1,2,3,4-tetrahydronaphthyl and the like, such as phenyl and naphthyl.

Heteroaryl is a 6 to 10 membered aromatic monocylic ring or bicyclic ring system wherein at least one ring is an aromatic nucleus comprising one or more, for example 1, 2, 3 or 4 heteroatoms independently selected from O, N and S. Examples of heteroaryls include: pyrrole, oxazole, thiazole, isothiazole, imidazole, pyrazole, isoxazole, pyridine, pyridazine, pyrimidine, pyrazine, benzothiophene, benzofuran, or 1, 2, 3 and 1, 2, 4 triazole.

Heterocyclyl as employed herein refers to a 5 to 6 membered saturated or partially unsaturated non-aromatic ring comprising one or more, for example 1, 2, 3 or 4 heteroatoms independently selected from O, N and S optionally one or two carbons in the ring may bear an oxo substituent. The definition of $C_{5-8}$ heterocycle as employed herein refers to a 5 to 6 membered saturated or partially unsaturated non-aromatic carbocyclic ring comprising one or more, for example 1, 2, 3 or 4 heteroatoms independently selected from O, N and S, wherein each heteroatom replaces a carbon atom and optionally one or two carbons may bear an oxo substitutent. Clearly any valancies of a heteroatom not employed in forming or retaining the ring structure may be filled by hydrogen or a substituent, as appropriate. Thus substituents on heterocycles may be on carbon or on a heteroatom, such as nitrogen, as appropriate. Examples of heterocycles and $C_{5-6}$ heterocycles include pyrroline, pyrrolidine, tetrahydrofuran, tetrahydrothiophene, pyrazoline, imidazoline, pyrazolidine, imidazolidine, oxoimidazolidine, dioxolane, thiazolidine, isoxazolidine, pyran, dihydropyran, piperidine, piperazine, morpholine, dioxane, thiomorpholine and oxathiane.

Halogen includes fluoro, chloro, bromo or iodo, in particular fluoro, chloro or bromo, especially fluoro or chloro.

Oxo as used herein refers to C=O and will usually be represented as C(O).

$S(O)_q C_{1-6}$ alkyl may, for example, include —$SO_2Me$.

$C_{3-8}$ cycloalkyl as employed herein is intended to refer to a saturated or partially unsaturated non-aromatic ring containing 3 to 8 carbon atoms, where the ring contains less than 8 carbons the ring may optionally bear one or more alkyl groups such that the number of carbon atoms in the ring plus the number of carbons in the alkyl substituents is not more than eight in total or 10 in the case of $C_{3-10}$ cycloalkyl.

$C_{1-10}$ alkyl includes $C_2$, $C_3$, $C_4$, $C_5$, $C_6$, $C_7$, $C_8$ or $C_9$ as well as $C_1$ and $C_{10}$.

$C_{0-8}$ alkyl includes $C_1$, $C_2$, $C_3$, $C_4$, $C_5$, $C_6$, or $C_7$ as well as $C_0$ and $C_8$.

In relation to a saturated or unsaturated, branched or unbranched $C_{1-10}$ alkyl chain (or similar language used herein), wherein at least one carbon (for example 1, 2 or 3 carbons, suitably 1 or 2, in particular 1) is replaced by a heteroatom selected from O, N, $S(O)_p$, wherein said chain is optionally, substituted by one or more groups independently selected from oxo, halogen, an aryl group, a heteroaryl group or a heterocyclyl group, it will be clear to persons skilled in the art that the heteroatom may replace a primary, secondary or tertiary carbon, that is $CH_3$, —$CH_2$— or a —CH—, a tertiary carbon group or —CH=, as technically appropriate.

Saturated or unsaturated, branched or unbranched $C_{1-10}$ alkyl alicyclic chain is intended to refer to $C_{3-10}$ cycloalkyl.

In one embodiment J represents:

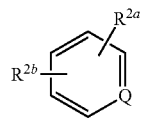

In one embodiment J represents:

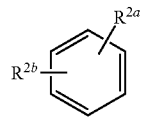

In one embodiment $R^1$ is —$C_{1-6}$ alkyl (optionally substituted by OH) $C_{3-10}$ cycloalkyl, $C_{3-10}$ heterocycloalkyl, $C_{1-6}$ haloalkyl, $C_{1-6}$ alkylOC(O)$CH_3$.

In one embodiment of the disclosure there is provided compounds of formula (I), wherein $R^1$ is methyl, ethyl, propyl, iso-propyl, butyl or tert-butyl, in particular tert-butyl.

In one embodiment $R^1$ is —$C(CH_3)_2CH_2OH$.

In one embodiment $R^1$ is cyclopropyl, or 1-methylcyclopropyl, cyclopentyl, cyclohexyl, or 1-methylcyclohexyl, or adamantly.

In one embodiment $R^1$ is tetrahydropyranyl or 4-methyltetrahydro-2H-pyran-4-yl.

In one embodiment $R^1$ is —$CF_3$, —$CF_2CF_3$ or —$CCl_3$.

In one embodiment $R^1$ is phenyl.

In one embodiment $R^{2a}$ is in the 2, 3, or 4 position (i.e. ortho, meta or para position), in particular the para (4) position.

In one embodiment $R^{2a}$ is methyl, ethyl, n-propyl, iso-propyl, n-butyl or tert-butyl, in particular methyl, for example in position 3 or 4.

In one embodiment $R^{2a}$ is —OH, for example in position 3 or 4.

In one embodiment $R^{2a}$ is halo, such as chloro, for example in position 3 or 4.

In one embodiment $R^{2a}$ is —$C_{1-6}$ alkyl substituted by a hydroxyl group such as —$CH_2OH$, for example in position 3 or 4.

In one embodiment $R^{2a}$ is —$C_{1-6}$ alkoxy, such as —$OCH_3$, for example in position 3 or 4.

In one embodiment $R^{2a}$ a is —$SC_{1-6}$ alkyl, such as —$SCH_3$, for example in position 3 or 4.

In one embodiment $R^{2a}$ is —$SO_2C_{1-6}$ alkyl, such as —$SO_2CH_3$ for example in the 3 or 4 position.

In one embodiment $R^{2a}$ is —$OCF_3$, for example located in position 3 or 4.

In one embodiment $R^{2a}$ a is —NR'R" wherein R' is H, —$C_{1-3}$ alkyl or —$SO_2C_{1-3}$alkyl, and R" is H or —$C_{1-3}$ alkyl, for example located in position 3 or 4. In one embodiment $R^{2a}$ is —$NH_2$, for example in position 3 or 4.

In one embodiment $R^{2a}$ is —$NHSO_2CH_3$, for example in position 3 or 4.

In one embodiment $R^{2b}$ is H.

In one embodiment $R^{2b}$ is halo such as chloro, for example in position 3.

In one embodiment $R^{2a}$ is chloro and $R^{2b}$ is chloro, for example 3,4-dichloro.

In one embodiment $R^{2a}$ chloro is and $R^{2b}$ is —OCH$_3$, for example in positions 3,4 respectively.

In one embodiment $R^{2a}$ is —OCH$_3$ and $R^{2b}$ is —OCH$_3$, for example in position 3,4.

In one embodiment $R^{2a}$ chloro is and $R^{2b}$ is —OH, for example in position 3,4 respectively.

In one embodiment at least one of $R^{2a}$ or $R^{2b}$ is not hydrogen.

In one embodiment both $R^{2a}$ and $R^{2b}$ are not hydrogen

In embodiments of the invention wherein the group Q represents N, the substituents $R^{2a}$ and $R^{2b}$ on the ring are pharmaceutically acceptable and do not include those of a highly reactive nature (such as a halogen atom disposed ortho to the heteroatom) such that compounds of formula (I) would be unstable and thereby unsuitable for their intended utility.

In one embodiment J is pyridine and $R^{2a}$ is methyl, ethyl, n-propyl, iso-propyl, n-butyl or tert-butyl, in particular methyl, for example in position 2 or 3.

In one embodiment J is pyridine and $R^{2a}$ is —C$_{1-6}$ alkyl substituted by a hydroxyl group such as —CH$_2$OH, for example in position 2 or 3.

In one embodiment J is pyridine and $R^{2a}$ is —C$_{1-6}$ alkoxy, such as —OCH$_3$, for example in position 2 or 3.

In one embodiment J is pyridine and $R^{2a}$ is —SC$_{1-6}$ alkyl, such as —SCH$_3$, for example in position 2 or 3.

In one embodiment J is pyridine and $R^{2a}$ is —SO$_2$C$_{1-6}$ alkyl, such as —SO$_2$CH$_3$ for example in the 3 position.

In one embodiment J is pyridine and $R^{2a}$ is —OCF$_3$, for example located in position 3.

In one embodiment when J is pyridine and $R^{2a}$ is —NR'R" wherein R' is H, —C$_{1-3}$ alkyl or —SO$_2$C$_{1-3}$alkyl, and R" is H or —C$_{1-3}$ alkyl, for example located in position 2 or 3. In one embodiment $R^{2a}$ is —NH$_2$, for example in position 2 or 3.

In one embodiment J is pyridine and $R^{2a}$ is NHSO$_2$CH$_3$, for example in position 2 or position 3.

In one embodiment J is pyridine and $R^{2b}$ is H.

In one embodiment L represents O, CH$_2$, C=O or S(O)$_t$ where t is 0, 1 or 2, in particular 0 or 2.

In one embodiment L represents —OCH$_2$— or —OCH$_2$CH$_2$—.

In one embodiment X is pyridine.

In one embodiment $R^3$ is H.

In one embodiment $R^4$ is selected from:

a) a saturated or unsaturated, branched or unbranched C$_{1-10}$ alkyl chain, wherein at least one carbon (for example 1, 2 or 3 carbons, suitably 1 or 2, in particular 1 carbon) is replaced by a heteroatom independently selected from O, N, S(O)$_p$, wherein said chain is optionally, substituted by one or more groups (for example 1, 2 or 3 groups) independently selected from oxo, halogen, a C$_{6-10}$ aryl group, a 5 or 6 membered heteroaryl group, a 5 or 6 membered heterocyclyl group or a C$_{3-8}$ cycloalkyl group, each aryl, heteroaryl, heterocyclyl or cycloalkyl group bearing 0 to 3 substituents selected from halogen, hydroxyl, C$_{1-6}$ alkyl, C$_{1-6}$ alkoxy, C$_{1-6}$ haloalkyl, amino, C$_{1-4}$ mono or C$_{2-8}$ di-alkyl amino, C$_{1-4}$ mono or C$_{2-8}$ di-acyl amino, S(O)qC$_{1-6}$ alkyl, C$_{0-6}$ alkylC(O)C$_{1-6}$ alkyl or C$_{0-6}$ alkylC(O)NC$_{0-6}$ alkyl C$_{0-6}$ alkyl, C$_{0-6}$ alkylC(O)C$_{1-6}$ heteroalkyl, with the proviso that the atom linked directly to the carbonyl in —NR$^3$C(O)— is not an oxygen or a sulfur atom; and b) a C$_{0-8}$ alkyl-heterocycle wherein the heterocyclyl group has 5 or 6 members and comprises at least one heteroatom (for example 1, 2 or 3, suitably 1 or 2, in particular 1 heteroatom) selected from O, N, and S, and said heterocycle is optionally substituted by one, two or three groups independently selected from halogen, hydroxyl, C$_{1-6}$ alkyl, C$_{1-6}$ alkoxy, C$_{1-6}$ haloalkyl, amino, C$_{1-4}$ mono and C$_{2-8}$ di-alkyl amino, C$_{1-4}$ mono or C$_{2-8}$ di-acyl amino, S(O)$_q$ C$_{1-6}$ alkyl, C$_{0-6}$ alkylC(O)C$_{1-6}$ alkyl, C$_{0-6}$ alkylC(O)NC$_{0-6}$ alkyl C$_{0-6}$ alkyl or C$_{0-6}$ alkylC(O)C$_{0-6}$ heteroalkyl.

In one embodiment 1, 2, 3 or 4 carbon atoms are replaced in the alkyl chain of $R^4$ by heteroatoms independently selected from O, N, S(O)$_p$.

In one embodiment the heteroatom(s) replacing carbon(s) in the alkyl chain fragment of $R^4$ are selected from N and O.

In one embodiment the fragment $R^4$ is a saturated or unsaturated, branched or unbranched C$_{1-10}$ alkyl chain wherein at least one carbon (for example 1, 2, 3 or 4 carbons, in particular 1 or 2 carbons) is replaced by a heteroatom selected from O, N, S(O)$_p$, wherein said chain is optionally substituted by one or more groups selected from oxo, halogen, an aryl group, a heteroaryl group, a heterocyclyl group, or a C$_{3-8}$ cycloalkyl each aryl, heteroaryl, heterocyclyl or cycloalkyl group as per defined above for compounds of formula (I).

In one embodiment $R^4$ is a saturated or unsaturated, branched or unbranched C$_{1-8}$ alkyl chain or a C$_{1-6}$ alkyl chain, wherein at least one carbon is replaced by a heteroatom selected from —O, —N, S(O)$_p$. Alternatively, in this embodiment the alkyl chain may be a C$_{2-8}$ alkyl or a C$_{3-6}$ alkyl group, such as a C$_4$ alkyl or a C$_5$ alkyl group.

In one embodiment a nitrogen atom in the alkyl chain of $R^4$ is directly bonded to the carbonyl of the fragment —NR$^3$C(O) and additionally may, for example, be a terminal amino group. Thus in one embodiment $R^4$ represents N(C$_{1-4}$ alkyl)C$_{1-4}$ alkyl, NHC$_{1-9}$ alkyl or NH$_2$.

In one embodiment $R^4$ represents —NHC$_{1-6}$ alkyl such as —NHCH$_3$ or —NHCH$_2$CH$_3$ or —NHCH(CH$_3$)$_2$.

Thus in one embodiment the C$_{1-10}$ alkyl chain of $R^4$ is substituted by at least or only one oxo group, for example substitution on the chain consists of a single oxo group.

In one embodiment the C$_{1-10}$ alkyl chain of $R^4$ is substituted by at least or only 1, 2, 3, 4, 5 or 6 halogen atoms.

In one embodiment $R^4$ is C$_{1-4}$alkyl-V—R$^5$, such as C$_{1-3}$alkyl-V—R$^5$ wherein:

V is a heteroatom selected from NR$^v$, O or S(O)$_p$;

R$^v$ represents H or C$_{1-3}$ alkyl;

R$^5$ is H or —C$_{1-3}$ alkyl, and p is as defined above, with the proviso that the total alkyl chain length is not more than 10 carbon atoms, including replacement heteroatoms and that the resulting radical $R^4$ is a stable group, for example —CH$_2$SCH$_3$, —CH$_2$SO$_2$CH$_3$, —CH$_2$NHCH$_3$, —CH$_2$N(CH$_3$)$_2$—C(CH$_3$)$_2$NHCH$_3$, —CH(CH$_3$)N(CH$_3$)$_2$, —(CH$_2$)$_3$CHNHCH$_3$, —(CH$_2$)$_3$N(CH$_3$)$_2$, —CH$_2$OH, —CH$_2$OCH$_3$, —CH(CH$_3$)OCH$_3$, or —(CH$_2$)$_2$OCH$_3$.

In one embodiment $R^4$ is C$_{1-3}$ alkyl-V—(C$_{2-3}$ alkyl-Z—R$^6$)$_k$ wherein:

V is a heteroatom selected from N, NH, O or S(O)$_p$, such as N or NH (V is N in the case where k=2, or will be selected from NH, O or S(O)$_p$, in the case where k is 1, in particular NH);

Z is independently selected from NH, O or S(O)$_p$;

R$^6$ is H or —C$_{1-3}$alkyl;

k is an integer 1 or 2 (such as 1); and p is as defined above, with the proviso that the total alkyl chain length is not more than 10 carbon atoms, including replacement heteroatoms and that the resulting radical R$^6$ is a stable group. Suitably $R^4$ is C$_{1-3}$alkyl-V—C$_{1-3}$alkyl-OCH$_3$ for example C$_{1-3}$alkyl-V—

$C_{2-3}$alkyl-$OCH_3$ such as $C_{1-3}$alkyl-V—$(CH_2)_2OCH_3$, in particular —$CH_2$—O—$(CH_2)_2OCH_3$ and $CH_2S(CH_2)_2OCH_3$, or —$CH_2NH(CH_2)_2OCH_3$, $C_{1-3}$alkyl-V—$(C_{1-3}$alkyl-$OCH_3)_k$ wherein k represents 2, for example $C_{1-3}$alkyl-V—$(C_{2-3}$alkyl-$OCH_3)_k$ such as —$CH_2N[(CH_2)_2OCH_3]_2$.

In one embodiment $R^4$ is $C_{1-3}$ alkyl-V—$C_{2-3}$ alkyl-Z—$C_{2-3}$ alkyl-Y—$R^7$, wherein V, Z and Y are independently a heteroatom selected from NH, O or $S(O)_p$, $R^7$ is H or methyl, and p is as defined above, with the proviso that the total alkyl chain length is not more than 10 carbon atoms, including replacement heteroatoms and that the resulting radical $R^4$ is a stable group. Suitably $R^4$ is —$CH_2V(CH_2)_2O(CH_2)_2OCH_3$, such as —$CH_2O(CH_2)_2O(CH_2)_2OCH_3$, —$CH_2NH(CH_2)_2O(CH_2)_2OCH_3$ or —$CH_2S(CH_2)_2O(CH_2)_2OCH_3$.

In one embodiment $R^4$ represents —$NR^8R^9$ and thus —$NR^3C(O)R^4$ forms a urea, where $R^8$ and $R^9$ independently represent hydrogen or a $C_{1-9}$ saturated or unsaturated, branched or unbranched alkyl chain, wherein one or more carbons, such as 1, 2 or 3 are optionally replaced by a heteroatom selected from O, N or $S(O)_p$. Said chain is optionally substituted by one or more groups independently selected from oxo, halogen, an aryl group, a heteroaryl group, a heterocyclyl or $C_{3-8}$ cycloalkyl group (such as oxo, halogen, an aryl group, a heteroaryl group or a heterocyclyl group), each aryl, heteroaryl or heterocyclyl group bearing 0 to 3 substituents independently selected from the relevant substituents listed above for compounds of formula (I), for example halogen, $C_{1-6}$ alkyl, $C_{1-6}$ alkoxy, $C_{1-6}$ haloalkyl, amino, $C_{1-4}$ mono or $C_{2-8}$ di-alkyl amino and $C_{1-4}$ mono or $C_{2-8}$ di-acyl amino with the proviso that the total alkyl chain length is not more than 10 carbon atoms, including replacement heteroatoms and that the resulting radical $R^4$ is a stable group.

In this urea embodiment in one sub-embodiment $R^8$ represents hydrogen.

Examples of ureas include those in which $R^8$ and $R^9$ are both hydrogen and thus $R^4$ is —$NH_2$, or where $R^4$ is —$NHCH_3$ or —$N(CH_3)_2$ thereby providing, for example, a fragment —$NR^3C(O)NH_2$ or —$NR^3C(O)NHCH_3$ or —$NR^3C(O)N(CH_3)_2$.

Examples of ureas containing a heteroatom in the alkyl chain include those in which $R^4$ is —$NH(CH_2)_2OCH_3$ or —$N[(CH_2)_2OCH_3]_2$. In one embodiment $R^4$ represents —$NHC_{2-6}$ alkyl$OC_{1-3}$ alkyl, such as —$NHCH_2CH_2OCH_3$.

Examples of ureas containing an oxo substituent include those in which $R^4$ is —$NHCH_2C(O)NH—C_{2-3}$ alkyl-$X^1$—$C_{1-3}$ alkyl, wherein $X^1$ is a heteroatom selected from N, O or $S(O)_p$ and p is defined as above. Examples of the latter include those wherein $R^6$ is —$NHCH_2C(O)NHCH_2CH_2OCH_3$. Thus in one embodiment $R^4$ represents —$NHC_{1-4}$ alkylC(O)NHC_2$alkylOCH_3$ such as —$NHCH_2C(O)NHCH_2CH_2OCH_3$.

In one embodiment $R^4$ represents $NHC_{1-4}$ alkylC(O)$R^{10}$ wherein $R^{10}$ is selected from OH or —$NR^{11}R^{12}$ where $R^{11}$ is hydrogen or $C_{1-3}$ alkyl and $R^{12}$ is hydrogen or $C_{1-3}$ alkyl, for example —$NHCH_2C(O)OH$, —$NHCH_2C(O)NH_2$ or —$NHCH_2C(O)NHCH_3$ such as —$NHCH_2C(O)OH$ or —$NHCH_2C(O)NHCH_3$.

In one embodiment $R^4$ represents —$NHC_{1-4}$ alkylC(O)$OC_{1-3}$ alkyl, such as —$NHCH_2C(O)OCH_2CH_3$.

In a further urea sub-embodiment $R^4$ represents —$N(R^{13})C_{2-3}$ alkyl-V—$(C_{2-3}$alkyl-Z—$R^{14})_k$ wherein:

V represents N, NH, O, $S(O)_p$;

Z represents NH, O, $S(O)_p$;

k is an integer 1 or 2;

p is an integer 0, 1 or 2

$R^{13}$ represents H or $C_{2-3}$ alkyl-V—$(C_{2-3}$alkyl-Z—$R^{14})_k$; and $R^{16}$ is H or $C_{1-3}$ alkyl such as $C_{1-3}$ alkyl;

with the proviso that the total alkyl chain length is not more than 10 carbon atoms, including replacement heteroatoms and that the resulting radical $R^4$ is a stable group.

In one embodiment $R^4$ is a saturated or unsaturated, branched or unbranched $C_{1-10}$ alkyl chain, wherein at least one carbon is replaced by a heteroatom selected from O, N, and $S(O)_p$, wherein said chain is substituted by an aryl group bearing 0 to 3 substituents, for example 1, 2 or 3, such as 1 or 2 substituents independently selected from the relevant substituents listed above for compounds of formula (I), for example from halogen, $C_{1-6}$ alkyl, $C_{1-6}$ alkoxy, $C_{1-6}$ haloalkyl, amino and $C_{1-4}$ mono or $C_{2-8}$ di-alkyl amino and $C_{1-4}$ mono or $C_{2-8}$ di-acyl amino, such as a saturated or unsaturated, branched or unbranched $C_{1-10}$ alkyl chain, wherein at least one carbon is replaced by a heteroatom selected from O, N, and $S(O)_p$, wherein said chain is substituted by an aryl group bearing 0 to 3 substituents, for example 1, 2 or 3, such as 1 or 2 substituents independently selected from halogen, $C_{1-6}$ alkyl, $C_{1-6}$ alkoxy, $C_{1-6}$ haloalkyl, amino and $C_{1-4}$ mono or $C_{2-8}$ di-alkyl amino. In one embodiment the said aryl group is phenyl, for example substituted phenyl or unsubstituted phenyl.

In one embodiment $R^4$ represents —$NHC_{0-6}$ alkylphenyl, such as —NHphenyl or —NHbenzyl.

Examples of the fragment —$NR^3C(O)R^4$ wherein $R^4$ comprises substituted benzyl include: —$NR^3C(O)CH_2NHCH_2C_6H_4(OCH_3)$ such as —$NHC(O)CH_2NHCH_2C_6H_4(OCH_3)$, for example where the methoxy substituent is in the ortho, meta or para position, such as the para position.

In one embodiment $R^4$ is a saturated or unsaturated, branched or unbranched $C_{1-10}$ alkyl chain, wherein at least one carbon is replaced by a heteroatom selected from O, N, and $S(O)_p$, wherein said chain is substituted by a heteroaryl group bearing 0 to 3 substituents (for example 1, 2 or 3, such as 1 or 2 substituents) independently selected from the relevant substituents listed above for compounds of formula (I), for example halogen, $C_{1-6}$ alkyl, $C_{1-6}$ alkoxy, $C_{1-6}$ alkyl amino, $C_{1-4}$ mono or $C_{2-8}$ di-alkyl amino and $C_{1-4}$ mono or $C_{2-8}$ di-acyl amino, such as a saturated or unsaturated, branched or unbranched $C_{1-10}$ alkyl chain, wherein at least one carbon is replaced by a heteroatom selected from O, N, and $S(O)_p$, wherein said chain is substituted by a heteroaryl group bearing 0 to 3 substituents for example 1, 2 or 3, such as 1 or 2 substituents selected from halogen, $C_{1-6}$ alkyl, $C_{1-6}$ alkoxy, $C_{1-6}$ alkyl amino, $C_{1-4}$ mono or $C_{2-8}$ di-alkyl amino. In one embodiment the said heteroaryl group is selected from, thiophene, oxazole, thiazole, isothiazole, imidazole, pyrazole, isoxazole, isothiazole, oxadiazole, 1,2,3 or 1,2,4 triazole, pyridine, pyridazine, pyrimidine, pyrazine and, in particular pyridine and pyrimidine, especially pyridine.

In one embodiment $R^4$ represents —$NHC_{1-6}$ alkylheteroaryl, for example —$NH(CH_2)_3$imidazolyl or —$NHCH_2$isoxazole wherein the isoxazole is optionally substituted such as —$NHCH_2$ isoxazole($CH_3$).

In one embodiment $R^4$ represents —$NHC_{1-4}$ alkylC(O)NHC_{1-3}$ alkylheteroaryl, for example a nitrogen containing heteroaryl group or a nitrogen and oxygen containing heteroaryl, more specifically —$NHCH_2C(O)$ NHCH₂CH₂pyridinyl, in particular where pyridinyl is linked through carbon, for example pyridin-4-yl or —NHCH₂C(O)NHCH₂CH₂CH₂imidazolyl, in particular where imidazolyl is linked through nitrogen.

In one embodiment $R^4$ is a saturated or unsaturated, branched or unbranched $C_{1-10}$ alkyl chain, wherein at least one carbon is replaced by a heteroatom selected from O, N and $S(O)_p$ wherein said chain is substituted by a heterocyclyl group bearing 0 to 3 substituents (for example 1, 2 or 3, such as 1 or 2 substituents) independently selected from the relevant substituents listed above for compounds of formula (I), for example halogen, $C_{1-6}$ alkyl, $C_{1-6}$ alkoxy, $C_{1-6}$ haloalkyl amino, $C_{1-4}$ mono or $C_{2-8}$ di-alkyl amino and $C_{1-4}$ mono or $C_{2-8}$ di-acyl amino, such as a saturated or unsaturated, branched or unbranched $C_{1-10}$ alkyl chain, wherein at least one carbon is replaced by a heteroatom selected from O, N and $S(O)_p$ wherein said chain is substituted by a heterocyclyl group bearing 0 to 3 substituents, for example 1, 2 or 3, such as 1 or 2 substituents selected from halogen, $C_{1-6}$ alkyl, $C_{1-6}$ alkoxy, $C_{1-6}$ haloalkyl amino, $C_{1-4}$ mono or $C_{2-8}$ di-alkyl amino.

In one embodiment a heterocyclyl of $R^4$ is selected, from a 5 or 6 membered saturated or partially unsaturated ring system comprising one or more (for example 1, 2 or 3 in particular 1 or 2) heteroatoms independently selected from O, N and S, for example pyrrolidine, tetrahydrofuran, tetrahydrothiophene, piperidine, piperazine, morpholine, 1,4-dioxane, pyrrolidine and oxoimidazolidine such as pyrrolidine, tetrahydrofuran, tetrahydrothiophene, piperidine, piperazine, morpholine, and 1,4-dioxane, in particular piperidine, piperazine, and morpholine.

In one embodiment a heterocyclic group may be linked to the alkyl chain of $R^6$ or to the carbonyl of —$NR^3C(O)$— through carbon or nitrogen, in particular a nitrogen atom.

In one embodiment $R^4$ is —$C_{0-3}$ alkylheterocycle (for example —$C_{0-1}$ alkylheterocycle) said heterocyclyl group comprising at least one heteroatom (for example 1, 2 or 3, in particular 1 or 2, heteroatoms) selected from O, N and S, and is optionally substituted by one or two or three groups independently selected from the relevant substituents listed above for compounds of formula (I), for example halogen, $C_{1-6}$ alkyl, $C_{1-6}$ alkoxy, $C_{1-6}$ haloalkyl, amino, $C_{1-4}$ mono and $C_{2-8}$ di-alkyl amino and $C_{1-4}$ mono or $C_{2-8}$ di-acyl amino.

In one embodiment $R^4$ is —$C_0$ alkylheterocycle, for example a tetrahydropyranyl or a pyrrolidinyl or a morpholinyl or a piperazinyl or an oxoimidazolinyl group, such as 2-oxoimidazolidinyl group.

In one embodiment in which $R^4$ is —$C_0$ alkylheterocycle, the heterocycle is linked through carbon, and is, for example, a C-linked tetrahydropyran or a C-linked piperidine or a C-linked morpholine or a C-linked piperazine.

In one embodiment in which $R^4$ is —$C_0$ alkylheterocycle, the heterocyclic group containing one or more N atoms is linked through N. This embodiment provides for ureas in which one of the urea nitrogens is embedded within a heterocyclic ring. Examples of this embodiment include, but are not limited to, an N-linked morpholine or an N-linked piperidine or an N-linked piperazine, said N-linked piperizinyl group optionally bearing an additional C- or N-substituent (such as an N-methyl group or N—CH₂CH₂OCH₃ group. In one embodiment $R^4$ is a heterocyclyl linked through nitrogen such as piperidinyl, in particular 4-hydroxypiperidinyl or piperazinyl, such as 4-methyl piperazinyl. Thus in one embodiment $R^4$ represents a heterocyclyl group, for example a nitrogen containing heterocyclyl group, in particular linked through N, such as morpholinyl or piperazinyl optionally substituted by methyl, especially 4-methyl, or piperidinyl.

In one embodiment $R^4$ represents tetrahydrofuranyl, morpholinyl, piperidinyl such as piperidinyl bearing one hyroxyl substituent, piperazinyl such as piperazinyl bearing one methyl substituent or pyrrolidinyl such a pyrrolidinyl bearing one di-methyl amino substituent. The ring may be linked through the heteroatom, such as nitrogen. Alternatively, the ring may be linked through carbon. The substituent may, for example be para relative to the atom through which the ring is linked to the remainder of the molecule.

In one embodiment $R^4$ is a —$C_1$ alkylheterocycle, for example tetrahydropyranylmethyl or a C- or N-linked piperazinylmethyl optionally bearing a substituent (for example a $C_{1-6}$ alkyl substitutent such as methyl or a $C_{1-6}$ alkoxy substituent such as —CH₂CH₂OCH₃). Additional examples include a C- or N-linked pyrrolidinylmethyl, or a C- or N-linked oxoimidazolinylmethyl (such as 2-oxoimidazolidinylmethyl, said heterocycle optionally bearing a substitutent (such as N-methyl or N—SO₂CH₃).

In one embodiment $R^4$ represents —NHheterocyclyl (wherein the heterocyclyl bears 0 to 3 substituents selected from the relevant list of substituents listed above for compounds of formula (I), for example halogen, hydroxy, $C_{1-6}$ alkyl, $C_{1-6}$ alkoxy, $C_{1-6}$ haloalkyl, amino, $C_{1-4}$ mono or $C_{2-8}$ di-alkyl amino, —$S(O)_q C_{1-6}$ alkyl, $C_{1-4}$ mono or $C_{2-8}$ di-acyl amino, $C_{0-6}$ alkylC(O) $C_{1-6}$ alkyl or $C_{0-6}$ alkylC(O)$C_{1-6}$ heteroalkyl), such as where the ring is linked through carbon, for example 2-piperidinyl or 3-piperidinyl or 4-piperidinyl, in particular 1-acetylpiperidin-4-yl, 1-methylpiperidin-4-yl, 1-(methylsulfonyl)piperidin-4-yl or 1-(2-(2-methoxy ethoxy)acetyl)piperidin-4-yl.

In one embodiment $R^4$ represents —$NHC_{1-6}$ alkylheterocyclyl for example a nitrogen containing heterocyclyl group, in particular one linked through nitrogen, such as —NHCH₂CH₂-morpholine, —NH(CH₂)₃-morpholine or —NH(CH₂)₄-morpholine.

In one embodiment $R^4$ represents —$NHC_{1-6}$ alkylC(O) heterocyclyl (wherein the heterocyclyl bears 0 to 3 substituents selected from the relevant list of substituents listed above for compounds of formula (I), for example halogen, hydroxy, $C_{1-6}$ alkyl, $C_{1-6}$ alkoxy, $C_{1-6}$ haloalkyl, amino, $C_{1-4}$ mono or $C_{2-8}$ di-alkyl amino, $C_{1-4}$ mono or $C_{2-8}$ di-acyl amino, $C_{0-6}$ alkylC(O)$C_{1-6}$ alkyl or $C_{0-6}$ alkylC(O)$C_{1-6}$ heteroalkyl) for example a nitrogen containing heterocyclyl group, in particular one linked through nitrogen, such as —NHCH₂C(O)-1-pyrrolindinyl, —NHCH₂C(O)-1-piperidinyl, —NHCH₂C(O)-4-morpholinyl or —NHCH₂C(O)piperazinyl such as —NHCH₂C(O)-4-methyl-1-piperazinyl.

In one embodiment $R^4$ represents —$NHC_{1-4}$ alkylC(O) $NHC_{1-3}$ alkylheterocyclyl for example a nitrogen containing heterocyclyl group or a nitrogen and/or oxygen containing heterocyclyl, such as —NHCH₂C(O) NHCH₂CH₂morpholinyl, in particular where morpholinyl is linked through nitrogen.

In one embodiment $R^4$ represents —$N(C_{1-3}$ alkyl)$C_{1-6}$ alkylheterocyclyl, for example a nitrogen containing heterocyclyl group, in particular linked through nitrogen, such as —N(CH$_3$)CH$_2$CH$_2$-morpholine, —N(CH$_3$)(CH$_2$)$_3$morpholine or —N(CH$_3$)(CH$_2$)$_4$morpholine.

In one embodiment R$^4$ is —C$_{1-3}$alkyl-G-C$_{1-3}$alkylheterocycle wherein G is a heteroatom selected from NH, O or S(O)$_p$ said heterocyclyl group comprising at least one heteroatom (for example 1, 2 or 3, in particular 1 or 2, heteroatoms) selected from O, N, and S, and is optionally substituted by one or two or three groups independently selected from relevant substituents listed above for compounds of formula (I), for example halogen, C$_{1-6}$ alkyl, C$_{1-6}$ alkoxy, C$_{1-6}$ haloalkyl, amino, C$_{1-4}$ mono and C$_{2-8}$ di-alkyl amino and C$_{1-4}$ mono or C$_{2-8}$ di-acyl amino such as one or two or three groups halogen, C$_{1-6}$ alkyl, C$_{1-6}$ alkoxy, C$_{1-6}$ haloalkyl, amino, C$_{1-4}$ mono and C$_{2-8}$ di-alkyl amino. Suitably R$^4$ is —CH$_2$G(CH$_2$)$_2$heterocycle for example —CH$_2$G(CH$_2$)$_2$tetrahydropyranyl; or —CH$_2$G(CH$_2$)$_2$morpholinyl in which the heterocyclyl is linked through nitrogen or carbon; or CH$_2$G(CH$_2$)$_2$ piperazinyl in which the heterocyclyl is linked through nitrogen or carbon and optionally bearing a further C- or N-substituent (for example a C$_{1-6}$ alkyl substitutent such as methyl or a C$_{1-6}$ alkoxy substituent such as —CH$_2$CH$_2$OCH$_3$); or —CH$_2$G(CH$_2$)$_2$pyrrolidinyl, in which the heterocyclyl is linked through nitrogen or carbon, for example linked through nitrogen; or —CH$_2$G(CH$_2$)$_2$oxoimidazolinyl (such as 2-oxo imidazolidinyl) for example linked through N and optionally bearing an additional C- or N-substitutent (such as N-methyl or N—SO$_2$CH$_3$), and in which G is O or NH.

In one embodiment G is O.

In one embodiment G is NH.

In one embodiment R$^4$ is a saturated or unsaturated C$_{1-10}$ alkyl chain wherein at least one carbon (for example 1, 2 or 3 carbons) is replaced by a heteroatom selected from O, N, S(O)$_p$ wherein said chain is substituted by a C$_{3-8}$ carbocyclyl group and said alkyl chain is optionally substituted by one or more (for example 1 or 2) groups selected from oxo and halogen. In one embodiment said C$_{3-8}$ carbocyclyl group bears one or more groups (for example 1, 2 or 3 groups) independently selected from halogen, hydroxyl, C$_{1-6}$ alkyl, C$_{1-6}$ alkoxy, C$_{1-6}$ haloalkyl, amino, C$_{1-4}$ mono or di-alkyl amino, C$_{1-4}$ mono or di-acyl amino, S(O)$_q$C$_{1-6}$ alkyl, C$_{0-6}$ alkylC(O)C$_{1-6}$ alkyl or C$_{0-6}$ alkylC(O)C$_{1-6}$ heteroalkyl.

In one embodiment R$^4$ represents NHC$_{3-6}$ cycloalkyl, such as —NHcyclopropyl, —NHcyclopentyl or —NHcyclohexyl.

In one embodiment the aryl, heteroaryl or heterocyclyl group bears at least one —S(O)$_q$C$_{1-6}$ alkyl substituent and optionally bears one or two further relevant substituents independently selected from the list of substituents defined above for compounds of formula (I).

In one embodiment the C$_{5-6}$ heterocycle bears at least one —S(O)$_q$C$_{1-6}$ alkyl substituent and optionally bears one or two further substituents independently selected from the relevant list of substituents defined above for compounds of formula (I).

In one embodiment the aryl, heteroaryl or heterocyclyl group bears at least one hydroxyl substituent and optionally bears one or two further substituents independently selected from the relevant list of substituents defined above for compounds of formula (I).

In one embodiment the C$_{5-6}$ heterocycle bears at least one hydroxyl substituent and optionally bears one or two further substituents independently selected from the relevant list of substituents defined above for compounds of formula (I).

In one embodiment the aryl, heteroaryl or heterocyclyl group bears at least one C$_{1-4}$ mono and/or C$_{2-8}$ di-acyl amino substituent and optionally bears one or two further substituents independently selected from the relevant list defined above for compounds of formula (I).

In one embodiment the C$_{6-6}$ heterocycle bears at least one C$_{1-4}$ mono and/or C$_{2-8}$ di-acyl amino substituent and optionally bears one or two further substituents independently selected from the relevant list defined above for compounds of formula (I).

In one embodiment the aryl, heteroaryl or heterocyclyl group bears at least one C$_{0-6}$ alkylC(O)C$_{1-6}$ heteroalkyl substituent and optionally bears one or two further substituents independently selected from the relevant list defined above for compounds of formula (I).

In one embodiment the C$_{5-6}$ heterocycle bears at least one C$_{0-6}$ alkylC(O)C$_{1-6}$ heteroalkyl substituent and optionally bears one or two further substituents independently selected from the relevant list defined above for compounds of formula (I).

In one embodiment the aryl, heteroaryl or heterocyclyl group bears at least one C$_{0-6}$ alkylC(O)C$_{1-6}$ alkyl substituent and optionally bears one or two further substituents independently selected from the relevant list defined above for compounds of formula (I).

In one embodiment the C$_{5-6}$ heterocycle bears at least one C$_{0-6}$ alkylC(O)C$_{1-6}$ alkyl substituent and optionally bears one or two further substituents independently selected from the relevant substituents defined above for compounds of formula (I).

In one embodiment the alkyl chain fragment of R$^4$ does not bear any optional substituents.

In one embodiment the alkyl chain of R$^4$ is saturated.

In one embodiment the alkyl chain of R$^4$ is unbranched.

In one embodiment the alkyl chain fragment of R$^4$ bears 1, 2, or 3, for example 1 or 2, in particular 1 optional substituent.

It will be clear to persons skilled in the art that the heteroatom may replace a primary, secondary or tertiary carbon, that is a CH$_3$, —CH$_2$— or a —CH—, group, as technically appropriate.

In one embodiment p is 0 or 2.

In one embodiment p is 1.

In one embodiment compounds of the disclosure include those in which the fragment R$^4$ is:
—CH$_2$OH;
—CH$_2$OC$_{1-6}$ alkyl, in particular —CH$_2$OCH$_3$;
—CH$_2$CH$_2$OCH$_3$;
—CH$_2$O(CH$_2$)$_2$OCH$_3$;
—CH(CH$_3$)OCH$_3$;
—CH$_2$NHCH$_3$ or —CH$_2$N(CH$_3$)$_2$;
—CH$_2$NHCH$_2$CH$_2$OCH$_3$ or —CH$_2$NHC(O)CH$_2$OCH$_3$;
—CH$_2$SCH$_3$, —CH$_2$S(O)$_2$CH$_3$ or —CH$_2$NHC(O)CH$_2$S(O)$_2$CH$_3$; or
—CH$_2$NHC(O)CH$_2$.

In one embodiment compounds of the disclosure include those in which R$^4$ in formula (I) is represented by:
—CH$_2$OH;
—CH$_2$OC$_{1-6}$ alkyl, in particular —CH$_2$OCH$_3$;
—CH$_2$O(CH$_2$)$_{2-4}$OCH$_3$, in particular —CH$_2$O(CH$_2$)$_2$OCH$_3$;
—CH(CH$_3$)OCH$_3$;
—CH(CH$_3$)NHC$_{1-3}$alkyl in particular —CH(CH$_3$)NHCH$_3$;
—CH(CH$_3$)N(C$_{1-3}$alkyl)$_2$ in particular —CH(CH$_3$)N(CH$_3$)$_2$;
—C(CH$_3$)$_2$NHCH$_3$ in particular —C(CH$_3$)$_2$NHCH$_3$;
—(CH$_2$)$_2$OC$_{1-6}$ alkyl, in particular —(CH$_2$)$_2$OCH$_3$;
—(CH$_2$)$_3$NHC$_{1-3}$alkyl in particular —(CH$_2$)$_3$NHCH$_3$;
—(CH$_2$)$_3$N(C$_{1-3}$alkyl)$_2$ in particular —(CH$_2$)$_3$N(CH$_3$)$_2$;
—CH$_2$NHC$_{1-3}$alkyl in particular —CH$_2$NHCH$_3$;
—CH$_2$NH(CH$_2$)$_2$OCH$_3$;

—CH$_2$SCH$_3$;
—CH$_2$S(CH$_2$)$_2$OCH$_3$;
—CH$_2$S(CH$_2$)$_2$O(CH$_2$)$_2$OCH$_3$;
—CH$_2$SOCH$_3$;
—CH$_2$S(O)$_2$CH$_3$;
—CH$_2$N[(CH$_2$)$_2$OCH$_3$]$_2$;
—NH$_2$;
—NHC$_{1-9}$ alkyl, such as —NHC$_{1-7}$ alkyl, in particular —NHCH$_3$
—N(C$_{1-4}$ alkyl)C$_{1-5}$ alkyl in particular —N(CH$_3$)$_2$; or —NHCH$_2$CONH(CH$_2$)$_2$OCH$_3$.

In one embodiment compounds of the disclosure include compounds of formula (I) in which C$_{0-8}$alkylheterocyclyl of R$^4$ is represented by:
-tetrahydropyranyl, such as -tetrahydro-2H-pyran-4-yl:
-morpholinyl such as -4-morpholinyl or —NHC(O)(3-morpholinyl);
-pyrrolidinyl, such as -pyrrolidin-1-yl;
-piperazinyl, such as -piperazin-1-yl;
-methylpiperazinyl, such as -4-methylpiperazin-1-yl;
-[(methoxyethyl)piperazinyl], such as -[4-(2-methoxyethyl)piperazin-1-yl];
-oxoimidazolidinyl such as -2-oxoimidazolidinyl, in particular-2-oxoimidazolidin-1-yl;
—CH$_2$-tetrahydropyranyl, such as —CH$_2$-tetrahydro-2H-pyran-4-yl;
—CH$_2$-morpholinyl, such as —CH$_2$-4-morpholinyl;
—CH$_2$-pyrrolidinyl, such as —CH$_2$-pyrrolidin-1-yl;
—CH$_2$-piperazinyl, such as —CH$_2$-piperazin-1-yl;
—CH$_2$-(methylpiperazinyl), such as —CH$_2$-(4-methylpiperazin-1-yl);
—CH$_2$-[(methoxyethyl)piperazinyl], such as —CH$_2$-[4-(2-methoxyethyl)piperazin-1-yl];
—CH$_2$SCH$_2$CH$_2$-morpholinyl, such as, for example, —CH$_2$SCH$_2$CH$_2$-4-morpholinyl, or —CH$_2$SCH$_2$CH$_2$-3-morpholinyl; and
—CH$_2$SO$_2$CH$_2$CH$_2$-morpholinyl, such as for example —CH$_2$SO$_2$CH$_2$CH$_2$-4-morpholinyl, or —CH$_2$SO$_2$CH$_2$CH$_2$-3-morpholinyl.

In one embodiment of the fragment R$^4$, the saturated or unsaturated, branched or unbranched C$_{1-10}$ alkyl chain, wherein at least one carbon is replaced by a heteroatom selected from —O, —N, S(O)$_p$ is a linker selected from:
—CH$_2$OCH$_2$—, —CH$_2$NHCH$_2$—, —CH$_2$NH— and —CH$_2$OCH$_2$CH$_2$—. These fragments may optionally terminate in an aryl group, a heteroaryl group a heterocyclyl group or C$_{3-8}$ cycloalkyl group, such as an aryl group, a heteroaryl group a heterocyclyl group as defined for fragment R$^4$ above.

In one embodiment the disclosure relates to compounds of formula (IA):

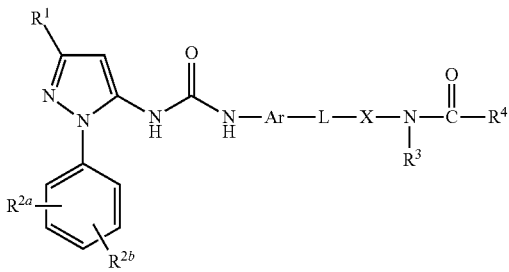

(IA)

wherein Ar, R$^1$, R$^{2a}$, R$^{2b}$, R$^3$, R$^4$, L and X, are defined above for compounds of formula (I).

In one embodiment the disclosure relates to compounds of formula (IB):

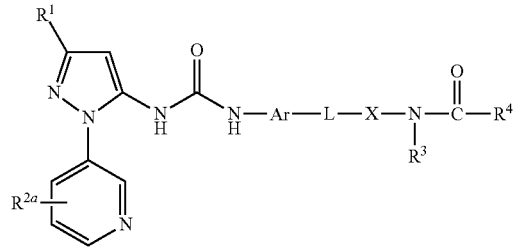

(IB)

wherein Ar, R$^1$, R$^{2a}$, R$^3$, R$^4$, L and X are defined above for compounds of formula (I).

In one embodiment the disclosure relates to compounds of formula (IC):

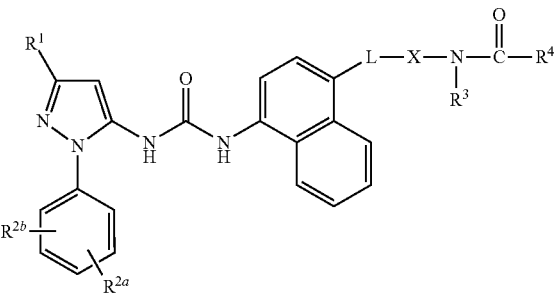

(IC)

wherein R$^1$, R$^{2a}$, R$^{2b}$, R$^3$, R$^4$, L and X are defined above for compounds of formula (I).

In one embodiment the disclosure relates to compounds of formula (ID):

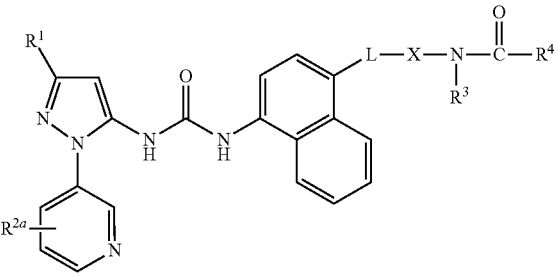

(ID)

wherein R$^1$, R$^{2a}$, R$^3$, R$^4$, L and X are defined above for compounds of formula (I).

In one embodiment the disclosure relates to compounds of formula (IE):

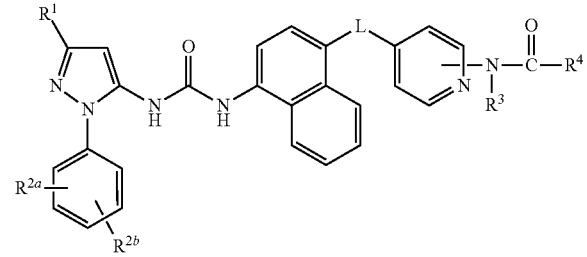

(IE)

wherein R$^1$, R$^{2a}$, R$^{2b}$, R$^3$, R$^4$ and L are defined above for compounds of formula (I).

In one embodiment in compounds of formula (IE) the nitrogen linked substituent is located at position 2 of the pyridine.

In one embodiment the disclosure relates to compounds of formula (IF):

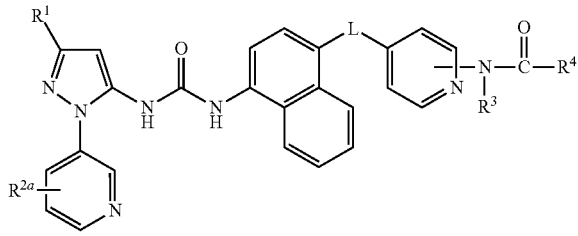

wherein $R^1$, $R^{2a}$, $R^3$, $R^4$ and L are defined above for compounds of formula (I).

In one embodiment in compounds of formula (IF) the nitrogen linked substituent is located at position 2 of the pyridine.

The preferences described above for compounds of formula (I) may also apply to compounds of formula (IA) to (IF).

In one embodiment the compound is:
N-(4-(4-(3-(1-(4-aminophenyl)-3-tert-butyl-1H-pyrazol-5-yl)ureido)naphthalen-1-yloxy)pyridin-2-yl)-2-methoxyacetamide;
N-(4-(4-(3-(3-tert-butyl-1-(6-methoxypyridin-3-yl)-1H-pyrazol-5-yl)ureido)naphthalen-1-yloxy)pyridin-2-yl)-2-methoxyacetamide;
N-(4-(4-(3-(3-tert-butyl-1-(4-methylthiophen-2-yl)-1H-pyrazol-5-yl)ureido)naphthalen-1-yloxy)pyridin-2-yl)-2-methoxyacetamide;
2-methoxy-N-(4-(4-(3-(3-(4-methyltetrahydro-2H-pyran-4-yl)-1-p-tolyl-1H-pyrazol-5-yl)ureido) naphthalen-1-yloxy)pyridin-2-yl)acetamide;
1-(3-tert-butyl-1-(4-methoxyphenyl)-1H-pyrazol-5-yl)-3-(4-(2-(3-cyclopropylureido)pyridin-4-yloxy)naphthalen-1-yl)urea;
N-(4-(4-(3-(3-tert-butyl-1-(4-(methylthio)phenyl)-1H-pyrazol-5-yl)ureido)naphthalen-1-yloxy)pyridin-2-yl)pyrrolidine-1-carboxamide;
N-(4-(4-(3-(3-tert-butyl-1-p-tolyl-1H-pyrazol-5-yl)ureido) naphthalen-1-ylthio)pyridin-2-yl)-2-methoxyacetamide;
N-(4-(4-(3-(3-tert-butyl-1-p-tolyl-1H-pyrazol-5-yl)ureido)-1-naphthoyl)pyridin-2-yl)-2-(2-methoxyethoxy)acetamide;
1-(3-tert-butyl-1-p-tolyl-1H-pyrazol-5-yl)-3-(4-((2-(3-ethylureido)pyridin-4-yl)methyl) naphthalen-1-yl)urea;
N-(4-((4-(3-(3-tert-butyl-1-(3-chloro-4-hydroxyphenyl)-1H-pyrazol-5-yl)ureido)naphthalen-1-yl)oxy)pyridin-2-yl)morpholine-4-carboxamide;
or a pharmaceutically acceptable salt of any one thereof, including all stereoisomers, tautomers and isotopic derivatives thereof.

In one embodiment the compound is:
N-(4-(4-(3-(1-(4-aminophenyl)-3-tert-butyl-1H-pyrazol-5-yl)ureido) naphthalen-1-yloxy)pyridin-2-yl)-2-methoxyacetamide;
N-(4-(4-(3-(3-tert-butyl-1-(4-(methylsulfonamido)phenyl)-1H-pyrazol-5-yl)ureido)naphthalen-1-yloxy)pyridin-2-yl)-2-methoxyacetamide;
N-(4-((4-(3-(3-tert-butyl-1-(4-methoxyphenyl)-1H-pyrazol-5-yl)ureido) naphthalen-1-yl)oxy)pyridin-2-yl)-2-methoxyacetamide;
N-(4-(4-(3-(3-tert-butyl-1-(4-methoxyphenyl)-1H-pyrazol-5-yl)ureido)naphthalen-1-yloxy)pyridin-2-yl)-2-hydroxyacetamide;
N-(4-((4-(3-(3-tert-butyl-1-(4-hydroxyphenyl)-1H-pyrazol-5-yl)ureido)naphthalen-1-yl)oxy)pyridin-2-yl)-2-methoxyacetamide;
1-(3-tert-butyl-1-(4-methoxyphenyl)-1H-pyrazol-5-yl)-3-(4-(2-(3-cyclopropylureido)pyridin-4-yloxy)naphthalen-1-yl)urea;
3-(4-(4-(3-(3-tert-butyl-1-(4-methoxyphenyl)-1H-pyrazol-5-yl)ureido)naphthalen-1-yloxy)pyridin-2-yl)-1,1-dimethylurea;
N-(4-(4-(3-(3-tert-butyl-1-(4-methoxyphenyl)-1H-pyrazol-5-yl)ureido)naphthalen-1-yloxy)pyridin-2-yl)pyrrolidine-1-carboxamide;
N-(4-(4-(3-(3-tert-butyl-1-(4-methoxyphenyl)-1H-pyrazol-5-yl)ureido)naphthalen-1-yl)oxy)pyridin-2-yl)morpholine-4-carboxamide;
N-(4-(4-(3-(3-tert-butyl-1-(4-methoxyphenyl)-1H-pyrazol-5-yl)ureido)naphthalen-1-yloxy)pyridin-2-yl)-4-methylpiperazine-1-carboxamide;
N-(4-(4-(3-(3-tert-butyl-1-(3,4-dimethoxyphenyl)-1H-pyrazol-5-yl)ureido)naphthalen-1-yloxy)pyridin-2-yl)-2-methoxyacetamide;
N-(4-((4-(3-(3-tert-butyl-1-(3-chloro-4-hydroxyphenyl)-1H-pyrazol-5-yl)ureido)naphthalen-1-yl)oxy)pyridin-2-yl)morpholine-4-carboxamide;
N-(4-(4-(3-(3-tert-butyl-1-(3-chloro-4-(hydroxymethyl)phenyl)-1H-pyrazol-5-yl)ureido) naphthalen-1-yloxy)pyridin-2-yl)-2-methoxyacetamide;
N-(4-(4-(3-(3-tert-butyl-1-(4-(methylthio)phenyl)-1H-pyrazol-5-yl)ureido)naphthalen-1-yloxy)pyridin-2-yl)pyrrolidine-1-carboxamide;
3-(4-(4-(3-(3-tert-butyl-1-(4-(methylsulfonyl)phenyl)-1H-pyrazol-5-yl)ureido)naphthalen-1-yloxy)pyridin-2-yl)-1,1-dimethylurea;
N-(4-(4-(3-(3-tert-butyl-1-(6-methoxypyridin-3-yl)-1H-pyrazol-5-yl)ureido)naphthalen-1-yloxy)pyridin-2-yl)-2-methoxyacetamide;
N-(4-(4-(3-(3-tert-butyl-1-(6-hydroxypyridin-3-yl)-1H-pyrazol-5-yl)ureido)naphthalen-1-yloxy)pyridin-2-yl)-2-methoxyacetamide;
N-(4-(4-(3-(3-tert-butyl-1-(4-methylthiophen-2-yl)-1H-pyrazol-5-yl)ureido)naphthalen-1-yloxy)pyridin-2-yl)-2-methoxyacetamide;
N-(4-((4-(3-(1,3-diphenyl-1H-pyrazol-5-yl)ureido)naphthalen-1-yl)oxy)pyridin-2-yl)-2-methoxy acetamide;
2-methoxy-N-(4-(4-(3-(3-(4-methyltetrahydro-2H-pyran-4-yl)-1-p-tolyl-1H-pyrazol-5-yl)ureido) naphthalen-1-yloxy)pyridin-2-yl)acetamide;
N-(4-(4-(3-(3-tert-butyl-1-p-tolyl-1H-pyrazol-5-yl)ureido) naphthalen-1-ylthio)pyridin-2-yl)-2-methoxyacetamide;
N-(4-(4-(3-(3-tert-butyl-1-p-tolyl-1H-pyrazol-5-yl)ureido)-1-naphthoyl)pyridin-2-yl)-2-(2-methoxyethoxy)acetamide;
1-(3-tert-butyl-1-p-tolyl-1H-pyrazol-5-yl)-3-(4-((2-(3-ethylureido)pyridin-4-yl)methyl) naphthalen-1-yl)urea;
N-(4-((4-(3-(3-cyclopropyl-1-p-tolyl-1H-pyrazol-5-yl)ureido)naphthalen-1-yl)oxy)pyridin-2-yl)-2-methoxyacetamide;
2-methoxy-N-(4-(4-(3-(3-(1-methylcyclopropyl)-1-p-tolyl-1H-pyrazol-5-yl)ureido)naphthalen-1-yloxy)pyridin-2-yl)acetamide;

2-methoxy-N-(4-(4-(3-(3-(1-methylcyclohexyl)-1-p-tolyl-1H-pyrazol-5-yl)ureido)naphthalen-1-yloxy)pyridin-2-yl)acetamide;
N-(4-(4-(3-(3-(adamantan-1-yl)-1-p-tolyl-1H-pyrazol-5-yl)ureido)naphthalen-1-yloxy)pyridin-2-yl)-2-methoxyacetamide;
2-methoxy-N-(4-(4-(3-(3-(tetrahydro-2H-pyran-4-yl)-1-p-tolyl-1H-pyrazol-5-yl)ureido) naphthalen-1-yloxy)pyridin-2-yl)acetamide;
2-methoxy-N-(4-(4-(3-(1-p-tolyl-3-(trifluoromethyl)-1H-pyrazol-5-yl)ureido)naphthalen-1-yloxy)pyridin-2-yl)acetamide;
2-methoxy-N-(4-(4-(3-(3-(perfluoroethyl)-1-p-tolyl-1H-pyrazol-5-yl)ureido)naphthalen-1-yloxy)pyridin-2-yl)acetamide;
N-(4-(4-(3-(3-tert-butyl-1-(4-((N-methylsulfamoyl)methyl)phenyl)-1H-pyrazol-5-yl)ureido) naphthalen-1-yloxy)pyridin-2-yl)-2-methoxyacetamide;
N-(4-(4-(3-(3-tert-butyl-1-(3-hydroxyphenyl)-1H-pyrazol-5-yl)ureido)naphthalen-1-yloxy)pyridin-2-yl)-2-methoxyacetamide;
1-(3-tert-butyl-1-(4-hydroxyphenyl)-1H-pyrazol-5-yl)-3-(4-(2-(3-methylureido)pyridin-4-yloxy)naphthalen-1-yl)urea;
3-(4-(4-(3-(3-tert-butyl-1-(4-hydroxyphenyl)-1H-pyrazol-5-yl)ureido)naphthalen-1-yloxy)pyridin-2-yl)-1,1-dimethylurea;
N-(4-(4-(3-(3-tert-butyl-1-(4-hydroxyphenyl)-1H-pyrazol-5-yl)ureido)naphthalen-1-yloxy)pyridin-2-yl)pyrrolidine-1-carboxamide;
N-(4-(4-(3-(3-tert-butyl-1-(3-methoxyphenyl)-1H-pyrazol-5-yl)ureido)naphthalen-1-yloxy)pyridin-2-yl)-2-methoxyacetamide;
1-(4-(4-(3-(3-tert-butyl-1-(4-methoxyphenyl)-1H-pyrazol-5-yl)ureido)-2,3-dimethylphenoxy)pyridin-2-yl)-3-methylurea;
1-(4-(4-(3-(3-tert-butyl-1-(4-methoxyphenyl)-1H-pyrazol-5-yl)ureido)naphthalen-1-yloxy)pyridin-2-yl)-3-methylurea;
1-(4-(4-(3-(3-tert-butyl-1-(6-methoxypyridin-3-yl)-1H-pyrazol-5-yl)ureido)-2,3-dimethyl phenoxy)pyridin-2-yl)-3-methylurea;
N-(4-(4-(3-(3-tert-butyl-1-(6-methoxypyridin-3-yl)-1H-pyrazol-5-yl)ureido)naphthalen-1-yloxy)pyridin-2-yl)morpholine-4-carboxamide;
N-(4-(4-(3-(3-tert-butyl-1-(4-(trifluoromethoxy)phenyl)-1H-pyrazol-5-yl)ureido)naphthalen-1-yloxy)pyridin-2-yl)-2-methoxyacetamide;
N-(4-(4-(3-(3-tert-butyl-1-(4-chlorophenyl)-1H-pyrazol-5-yl)ureido)naphthalen-1-yloxy)pyridin-2-yl)-2-methoxyacetamide;
Methyl-4-(3-tert-butyl-5-(3-(4-((2-(2-methoxyacetamido)pyridin-4-yl)oxy)naphthalen-1-yl)ureido)-1H-pyrazol-1-yl)benzoate;
N-(4-(4-(3-(3-tert-butyl-1-(4-(methylthio)phenyl)-1H-pyrazol-5-yl)ureido)naphthalen-1-yloxy)pyridin-2-yl)-2-methoxyacetamide;
1-(3-tert-butyl-1-(4-(methylsulfonyl)phenyl)-1H-pyrazol-5-yl)-3-(4-((2-ureidopyridin-4-yl)oxy)naphthalen-1-yl)urea;
1-(3-tert-butyl-1-(4-(methylsulfonyl)phenyl)-1H-pyrazol-5-yl)-3-(4-((2-(3-methylureido)pyridin-4-yl)oxy)naphthalen-1-yl)urea;
1-(3-tert-butyl-1-(4-(methylsulfonyl)phenyl)-1H-pyrazol-5-yl)-3-(4-(2-(3-cyclopropylureido) pyridin-4-yloxy)naphthalen-1-yl)urea;
N-(4-(4-(3-(3-tert-butyl-1-(4-(methylsulfonyl)phenyl)-1H-pyrazol-5-yl)ureido)naphthalen-1-yloxy)pyridin-2-yl)-4-methylpiperazine-1-carboxamide;
N-(4-(4-(3-(3-tert-butyl-1-(4-(methylsulfonyl)phenyl)-1H-pyrazol-5-yl)ureido)naphthalen-1-yloxy)pyridin-2-yl) morpholine-4-carboxamide;
N-(6-(4-(3-(3-tert-butyl-1-(4-(methylsulfonyl)phenyl)-1H-pyrazol-5-yl)ureido)naphthalen-1-yloxy)pyrimidin-4-yl)-2-methoxyacetamide;
N-(4-(4-(3-(3-tert-butyl-1-(4-(hydroxymethyl)-3-methoxyphenyl)-1H-pyrazol-5-yl)ureido) naphthalen-1-yloxy)pyridin-2-yl)-2-methoxyacetamide;
N-(4-(4-(3-(3-tert-butyl-1-(3-chloro-4-hydroxyphenyl)-1H-pyrazol-5-yl)ureido)naphthalen-1-yloxy)pyridin-2-yl)-2-methoxyacetamide;
N-(4-(4-(3-(3-tert-butyl-1-(3,5-dimethoxyphenyl)-1H-pyrazol-5-yl)ureido)naphthalen-1-yloxy)pyridin-2-yl)-2-methoxyacetamide;
N-(4-(4-(3-(3-tert-butyl-1-(3-chloro-4-methoxyphenyl)-1H-pyrazol-5-yl)ureido)naphthalen-1-yloxy)pyridin-2-yl)-2-methoxyacetamide;
N-(4-(4-(3-(3-tert-butyl-1-(3,4-dichlorophenyl)-1H-pyrazol-5-yl)ureido)naphthalen-1-yloxy)pyridin-2-yl)-2-methoxyacetamide;
N-(4-(4-(3-(3-tert-butyl-1-(thiophen-2-yl)-1H-pyrazol-5-yl)ureido)naphthalen-1-yloxy)pyridin-2-yl)-2-methoxyacetamide;
N-(4-(4-(3-(3-tert-butyl-1-(6-methylpyridin-3-yl)-1H-pyrazol-5-yl)ureido)naphthalen-1-yloxy)pyridin-2-yl)-2-methoxyacetamide;
N-(4-((4-(3-(3-tert-butyl-1-p-tolyl-1H-pyrazol-5-yl)ureido)-2,3-dimethylphenoxy)methyl)pyridin-2-yl)-2-methoxyacetamide;
N-(4-((4-(3-(3-tert-butyl-1-(4-methoxyphenyl)-1H-pyrazol-5-yl)ureido)-2,3-dimethylphenoxy)methyl)pyridin-2-yl)-2-methoxyacetamide;
1-(4-((4-(3-(3-tert-butyl-1-(4-methoxyphenyl)-1H-pyrazol-5-yl)ureido)-2,3-dimethylphenoxy)methyl)pyridin-2-yl)-3-methylurea;
N-(4-((4-(3-(3-tert-butyl-1-(6-methoxypyridin-3-yl)-1H-pyrazol-5-yl)ureido)-2,3-dimethyl phenoxy)methyl)pyridin-2-yl)-2-methoxyacetamide;
1-(4-((4-(3-(3-tert-butyl-1-(6-hydroxypyridin-3-yl)-1H-pyrazol-5-yl)ureido)-2,3-dimethyl phenoxy)pyridin-2-yl)-3-methylurea;
1-(4-((4-(3-(3-tert-butyl-1-(6-methoxypyridin-3-yl)-1H-pyrazol-5-yl)ureido)-2,3-dimethyl phenoxy)methyl)pyridin-2-yl)-3-methylurea;
N-(4-((4-(3-(3-tert-butyl-1-p-tolyl-1H-pyrazol-5-yl)ureido) naphthalen-1-yl)methyl)pyridin-2-yl)-2-methoxyacetamide;
N-(4-((4-(3-(3-tert-butyl-1-p-tolyl-1H-pyrazol-5-yl)ureido) naphthalen-1-yl)methyl)pyridin-2-yl)-2-(2-methoxyethoxy)acetamide;
N-(4-(4-(3-(3-tert-butyl-1-p-tolyl-1H-pyrazol-5-yl)ureido)-1-naphthoyl)pyridin-2-yl)-2-methoxy acetamide;
1-(3-tert-butyl-1-p-tolyl-1H-pyrazol-5-yl)-3-(4-(2-(3-ethylureido)isonicotinoyl)naphthalen-1-yl)urea;
or a pharmaceutically acceptable salt of any one thereof, including all stereoisomers, tautomers and isotopic derivatives thereof.

In one embodiment the compound of formula (I) is not 2-(5-(3-(4-(2-(2-methoxyacetamido)pyridin-4-yloxy)naphthalen-1-yl)ureido)-1-(p-tolyl)-1H-pyrazol-3-yl)-2-methylpropyl acetate.

Compounds of formula (I) as employed herein, unless the context indicates otherwise, is intended to refer to compounds of formula (IA) to (IF) and specifically named compounds, as technically appropriate.

The pharmaceutically acceptable salts as mentioned hereinabove are meant to include therapeutically active non-toxic acid addition salt forms that the compounds of formula (I) is/are able to form. These pharmaceutically acceptable acid addition salts can conveniently be obtained by treating the base form with such appropriate acid. Appropriate acids comprise, for example, inorganic acids such as hydrohalic acids, e.g. hydrochloric or hydrobromic acid, sulfuric, nitric, phosphoric and the like acids; or organic acids such as, for example, acetic, propanoic, hydroxyacetic, lactic, pyruvic, oxalic (i.e. ethanedioic), malonic, succinic (i.e. butanedioic acid), maleic, fumaric, malic, tartaric, citric, methanesulfonic, ethanesulfonic, benzenesulfonic, p-toluenesulfonic, cyclamic, salicylic, p-aminosalicylic, pamoic and the like acids.

Examples of salts of compound (I) include all pharmaceutically acceptable salts, such as, without limitation, acid addition salts of mineral acids such as HCl and HBr salts and addition salts of organic acids such as a methansulfonic acid salt.

The disclosure herein extends to solvates of compounds of formula (I). Examples of solvates include hydrates.

The compounds of the disclosure include those where the atom specified is a naturally occurring or non-naturally occurring isotope. In one embodiment the isotope is a stable isotope. Thus the compounds of the disclosure include, for example deuterium containing compounds and the like.

The compounds described herein may include one or more stereogenic centres, and the disclosure extends to include racemates, and to both enantiomers (for example each substantially free of the other enantiomer) and all stereoisomers, such as diastereomers resulting therefrom. In one embodiment one enantiomeric form is present in a purified form that is substantially free of the corresponding enantiomeric form.

The disclosure also extends to all polymorphic forms of the compounds herein defined.

Compounds of formula (I) can be prepared by a process comprising reacting a compound of formula (II):

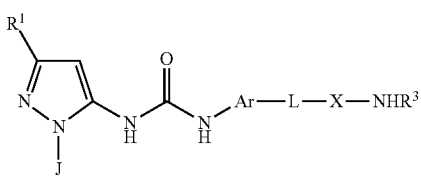

(II)

wherein J, L X, $R^1$, $R^3$ and Q are as defined above for compounds of formula (I) with a compound of formula (IIIa):

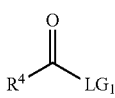

(IIIa)

where $LG_1$ is a leaving group for example halogen, such as chloro.

When $NR^3C(O)R^4$ is $NR^3C(O)NHR^*$ (wherein $R^*$ is the remainder of the fragment $R^6$) compounds of formula (I) can be prepared by reacting compounds of formula (II) with a compound of formula (IIIb):

*R—N=C=O          (IIIb)

The reaction is suitably carried out in the presence of an organic base such as DIPEA or triethylamine and in an aprotic solvent or solvent mixture such as a mixture of DCM and DMF Alternatively compounds of formula (I), in which $NR^3C(O)R^4$ is $NR^3C(O)NHR^*$, may be prepared by process in which a compound of formula (II) is reacted with a compound of formula (IVa):

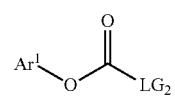

(IVa)

wherein $LG_2$ is a leaving group such as chloro and $Ar^1O$ is a leaving group, such as phenoxide, to provide a compound of formula (IIa)

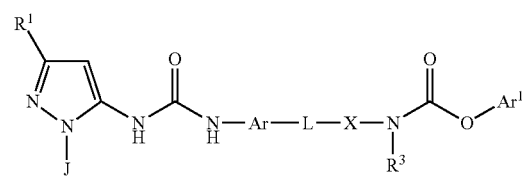

(IIa)

wherein $R^1$, J, Ar, L, X and $R^3$ are as defined above and $OAr^1$ is a leaving group, followed by reaction with an amine $R^*NH_2$, to provide the compound of formula (I)

Alternatively compounds of formula (I) can be prepared by reacting a compound of formula (V):

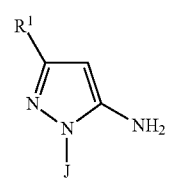

(V)

where $R^1$, J and are as defined above for compounds of formula (I), with a compound of formula (IVb):

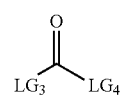

(IVb)

wherein $LG_3$ and $LG_4$ each independently represent leaving groups, to generate a compound of formula (VIa), for example when $LG_3$ and $LG_4$ both represent imidazolyl; or a compound of formula (VIb), for example when the groups $LG_3$ and $LG_4$ represent halogen, such chloro or trihalomethyl such as trichloromethyl)

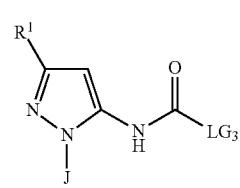

(VIa)

-continued

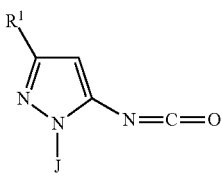
(VIb)

wherein $R^1$ and J are as defined above, followed by reaction with a compound of formula (VII):

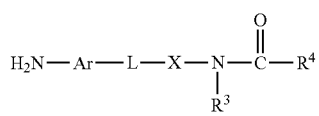
(VII)

wherein $R^3$, $R^4$, L, X, and Ar are as defined above for compounds of formula (I).

The reaction is suitably carried out in an aprotic solvent such as dichloromethane in the presence of a sterically hindered base, for example DIPEA.

It will be understood by persons skilled in the art that compounds represented by formulae (VIa) and (VIb) are generally reactive intermediates, and may be formed in situ and reacted directly, without isolation, with a compound of formula (VII) to provide a compound of formula (I). Furthermore it will be understood by those skilled in the art that the use of appropriate protective groups may be required during the processes described above, for any of the groups $R^1$, $R^{2a}$ $R^{2b}$ and $R^4$ that comprise of chemically sensitive functional groups, for example that contain a OH group or an $NH_2$ function.

Compounds of formula (II) can be prepared by reacting a compound of formula (VIII) wherein $R^3$, Ar, L and X are as defined above for compounds of formula (I):

$H_2N$—Ar-L-X—$NHR^3$ (VIII)

with a compound of formula (VIa) or a compound of formula (VIb), generated as described above from a compound of formula (V), in an aprotic solvent such as dichloromethane and a suitable base, for example DIPEA and, employing appropriate protective groups for chemically sensitive functionality.

Compounds of formula (VII) may be prepared by reacting a compound of formula (IX):

$O_2N$—Ar-L-X—$NHR^3$ (IX)

wherein $R^3$, Ar, L and X are as defined above for compounds of formula (I), with a compound of formula (IIIa) or (IIIb). The reaction is suitably carried out in the presence of an organic base such as DIPEA or triethylamine in an aprotic solvent or solvent mixture, such as. DCM and DMF. Alternatively, the compounds of formula (IX) may be reacted with a compound of formula (IVa) followed by reaction with an amine of formula R*$NH_2$.

From the intermediates so generated compounds of formula (VII) are then revealed by reduction of the nitro arene to the corresponding amine, for example by hydrogenation in the presence of a suitable catalyst, such as palladium on carbon. In certain cases it may be advantageous to conduct the reduction step chemically, for example under dissolving metal conditions, such as with iron in glacial acetic acid.

Compounds of formula (V) can be derived from the condensation of a phenylhydrazine of formula (X) or (Xa):

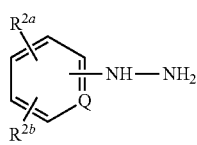
(X)

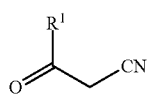
J—NH—$NH_2$ (Xa)

wherein J, $R^{2a}$, $R^{2b}$ and Q are as are defined above for compounds of formula (I), with a compound of formula (XI):

(XI)

wherein $R^1$ is as defined above for compounds of formula (I).

The reaction may be effected in an alcoholic solvent such as ethanol and in the presence of a mineral acid, such as HCl followed by treatment with a base, such as lithium hydroxide, in a solvent such as THF, to liberate the product, as a free base.

Compounds of formula (I) wherein any of the substituents $R^1$, or $R^{2a}$ or $R^{2b}$ contains a sensitive functional group may be prepared from a compound of formula (V), by the processes described above, in which the said functionality is suitably protected during the synthetic transformations, followed by an appropriate deprotection step. For example, a compound of formula (V) in which $R^1$, or $R^{2a}$ or $R^{2b}$ comprises a hydroxyalkyl, may be converted into a compound of formula (I) by the methods described above, by protecting the hydroxyl functionality, for example as a silyl ether. The hydroxyl group can be revealed at the end of the synthetic sequence by cleavage of the protective group: for example a silyl protective group may be removed with, for example, tetrabutylammonium fluoride.

Compounds of formula (V) wherein any of the substituents $R^1$, or $R^{2a}$ or $R^{2b}$ consists of a hydroxyalkyl such as, for example, —$(CH_2)_n CH_2 OH$ may be prepared by the reduction of compounds of formula (V) in which one or more of the substituents $R^1$, or $R^{2a}$ or $R^{2b}$ comprises the corresponding acid such as, for example —$(CH_2)_x CO_2 H$, wherein x is as appropriate for compounds of formula (I), employing a reagent such as borane in a suitable solvent, for example THF. The hydroxyl may then be optionally protected, for example as a silyl ether, and this intermediate converted into a compound of formula (I) in which $R^1$, or $R^{2a}$ or $R^{2b}$ is a protected hydroxyalkyl group, by one of the methods described above.

Compounds of formula (VIII) may be prepared by the reduction of a compound of formula (IX) to the corresponding amine, for example using hydrogenation in the presence of a suitable catalyst such as palladium on carbon.

Certain compounds of formula (IX) wherein the group L comprises of a fragment represented by —$O(CH_2)_{1-5}$— may be obtained by the reaction of a compound of formula (XIIa), wherein X and $R^5$ are as defined for compounds of formula (I)

HO—$(CH_2)_{1-5}$—X—$NHR^3$ (XIIa)

and a compound of formula (XIII):

$O_2N$—Ar—OH (XIII)

wherein Ar is as defined above for compounds of formula (I), for example under Mitsunobu coupling conditions, typically in the presence of a triarylphosphine such as triphenylphosphine and a dialkyl azodicarboxylate such as diisopropylazodicarboxylate. The reaction is suitably carried out in a polar aprotic solvent, such as THF.

Alternatively, certain compounds of formula (IX) wherein the group L comprises of a fragment represented by —O(CH$_2$)$_{1-5}$— may be obtained by a nucleophilic aromatic substitution (S$_N$Ar) reaction of a compound of formula (XIIa) with a compound of (XIV)

  (XIV)

wherein Ar is as defined above for compounds of formula (I) and Z is a halogen atom, most preferably fluorine. The reaction is conveniently conducted in the presence of a strong base such as sodium hydride and in an aprotic solvent such as THF.

Certain compounds of formula (IX) wherein the group L is O, that is an oxa linker, may be obtained by the reaction of a compound of formula (XIIb), wherein X and R$^5$ are as defined for compounds of formula (I)

  (XIIb)

and a compound of formula (XIV). The reaction may be conducted in the presence of an organic base such DBU in a polar aprotic solvent such as acetonitrile.

Certain compounds of formula (IX) wherein the group L is O, that is an oxa linker, may be obtained by the reaction of a compound of formula (XIIc), wherein X and R$^3$ are as defined for compounds of formula (I) and Y' is a halogen atom preferably chlorine

  (XIII)

and a compound of formula (XIII). The reaction may be effected in a polar aprotic solvent, such as NMP, in the presence of a strong mineral acid, such conc. hydrochloric acid and at an elevated temperature for example at 170° C. or 190° C.

Certain compounds of formula (VII) wherein the group L is O, that is an oxa linker, may be obtained via the reaction of a compound of formula (XIId),

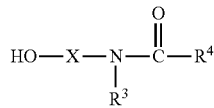  (XIId)

wherein X, R$^3$ and R$^4$ are as defined for compounds of formula (I) with a compound of formula (XIV) providing compounds of formula (XV).

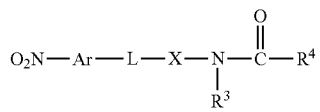  (XV)

Compounds of formula (VII) are revealed from compounds of formula (XV) by the reduction of the nitroarene to the corresponding amine. This transformation may be conducted by catalytic hydrogenation in a suitable solvent mixture such as a mixture of DCM, MeOH and acetic acid, over an appropriate metal catalyst, for example platinum supported on graphite, at RT. Alternatively it may be advantageous to conduct the reduction step by chemical means, for example using a metal such as iron powder, in an acid, such as glacial acetic acid at an elevated temperature, such as 60° C.

Certain compounds of formula (II) wherein X, R$^1$, R$^{2a}$, R$^{2b}$ and R$^3$ are as defined above for compounds of formula (I) and the group L is CH$_2$, that is a methylene linker; or is C(O), that is a keto group; or is S, that is a thio ether linker; may be prepared from a compound of formula (VIII) wherein R$^3$ and X are as defined above and L is either is CH$_2$, or is C(O) or is S; by reaction with a compound of formula (VIa) or a compound of formula (VIb) as described above.

A compound of formula (VIII) wherein R$^3$ and X are as defined above and L is either CH$_2$, or is C(O) may be obtained by the deprotection of the corresponding protected derivatives (VIIIa) or (VIIIb), respectively, wherein P$^1$ and P$^2$ represent suitable amine protective groups. For example, where P$^1$ and P$^2$ both represent Boc protective groups the desired compounds of formula (VIII) are revealed from compounds (VIIIa) or (VIIIb) by treatment with acid such as TFA, in an inert solvent such as DCM, conveniently at 0° C. to RT.

  (VIIIa)

  (VIIIb)

A compound of formula (VIIIa) may be obtained from a carbinol compound of formula (XVI) by a reductive process for the removal of the hydroxyl group. For example the compound of formula (XVI) can be converted into a sulfonate ester by treatment with a sulfonyl chloride, for example into the mesylate (XVIa) by treatment with methanesulfonyl chloride, in an aprotic solvent such as DCM at 0° C. to RT in the presence of a base such as triethylamine:

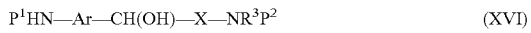  (XVI)

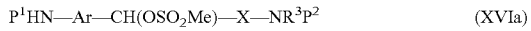  (XVIa)

The compound of formula (XVIa) may then be transformed into the compound of formula (VIIIa) by reaction with a reducing agent, such as sodium borohydride, in a polar protic solvent such as methanol, typically at 0° C. to RT.

A compound of formula (VIIIb) may also be obtained from the carbinol compound of formula (XVI) by an oxidative process to convert the secondary alcohol into a keto group. For example the compound of formula (XVI) may be converted into the compound of formula (VIIIb) by treatment with an oxidising agent such as manganese dioxide in a suitable solvent such as DCM, at an appropriate temperature such as 0° C. to RT.

Compounds of formula (XVI) may be prepared by the treatment of an aromatic bromide of formula (XVII), wherein Ar and P$^1$ are as defined above, with an alkyllithium, for example n-butyllithium, in an inert, aprotic solvent such at THF, at suitable temperature, for example at −78° C., if necessary with adjustment of the temperature to, for example, 0, followed by reaction with a carboxaldehyde of formula (XVIII), wherein X, R$^3$, and P$^2$ are as defined above:

  (XVII)

  (XVIII)

Compounds of formula (VIII) wherein R$^3$, Ar and X are as defined above and L is S, that is L is a thioether linker, may be prepared from a compound of formula (VIIIc) wherein the group Ar$^1$ is a electron rich aromatic nucleus, thereby making the radical —CH$_2$—Ar$^1$ susceptible to cleavage by acidolysis. A suitable aromatic group for this purpose is, for example 2,4-dimethoxybenzene or the like. The desired compound of formula (VIII), as defined above, may be obtained from the compound of formula (VIIIc)

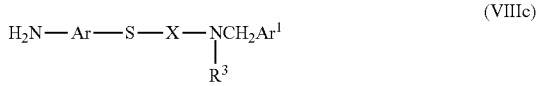

wherein Ar, X, $R^3$ and $Ar^1$ are defined above, by acid mediated cleavage, for example with hydrochloric acid in an alcoholic solvent such methanol, at an elevated temperature such as at reflux.

Compounds of formula (VIIIc) are obtainable from the reaction of a compound of formula (XIX) wherein Ar and X are as defined above and Y' is a halogen atom, preferably chlorine, with a compound of (XX), wherein $R^3$ and $Ar^1$ are as defined above. The reaction may be carried out by heating the compound of formula (XX) as a solution in the neat amine of formula (XX) at a suitable temperature, such as 120° C.:

Compounds of formula (XIX) may be prepared by reduction of compounds of formula (XXI):

wherein Ar, X and Y' are defined above, for example by catalytic reduction using hydrogen and a suitable metal catalyst.

The reduction step is conveniently carried out in a mixture of solvents such as EtOAc, MeOH and AcOH, over platinum on carbon, at an elevated temperature such as 50° C.

Compounds of formula (XXI) may be prepared by the reaction of compounds of formula (XIV), as defined above, with a compound of formula (XXII) wherein X is as defined above, Z is a halogen atom, preferably fluorine and Y' is a halogen atom, preferably chlorine together with a suitable sulfur nucleophile:

For example the reaction can be carried using sodium hydrogensulfide as the sulfur source in a polar aprotic solvent such as DMF and in the presence of a organic base, for example DIPEA, at ambient temperature.

Certain compounds of formula (I) wherein, $R^3$ is H and L is $SO_2$, that is L is a sulfonyl linker, may be prepared from a compound of formula (IIc) by one or more of the processes described above

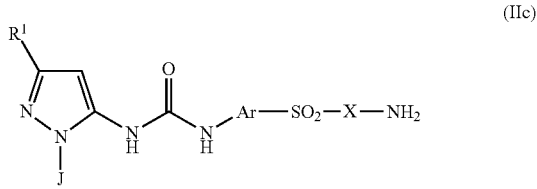

wherein $R^1$, J, Ar and X are as previously defined.

Compounds of formula (IIc) can be derived from a compound of formula (XXIII),

wherein Ar, X and $P^1$ are as previously defined, by conversion, in situ, into an isocyanate of formula (XXIIIa) followed by, without isolation, reaction with a compound of formula (V). The transformation may be effected by exposing the compound of formula (XXIII) to a compound of formula (IVb); wherein, for example, the group $LG_3$ is halogen such as chlorine and the group $LG_4$ is trihalomethoxy such as trichloromethoxy, such that the compound of formula (IVb) is diphosgene, and subsequently of admixing the compound of formula (V). The reaction is conveniently conducted in an inert aprotic solvent such as DCM and may be cooled, for example to 0° C. The desired compounds of formula (IIc) are then revealed from the products so obtained by a deprotection step. For example, where $P^1$ represents a Boc group the compounds of formula (IIc) are obtained following removal of the protective group with an acid such as TFA, in an inert solvent such as DCM, conveniently at 0° C. to RT.

Compounds of formula (XXIII) may be obtained by the reduction of compounds of formula (XXIV).

The reduction may be carried out, for example, by hydrogenation over a suitable catalyst, such as palladium on carbon, in an appropriate solvent system such as a mixture of EtOAc, MeOH and AcOH, and if necessary with warming, for example at 30° C.

Compounds of formula (XXIV) are accessible from compounds of formula (XXIa)

wherein Ar and X are as previously defined above and Y' is a halogen atom, preferably chlorine, by an amidation reaction employing a compound of formula (XXV). A suitable compound of formula (XXV) for this transformation is that in which R represents tert-butyl such that the said compound (XXV) is $H_2NBoc$. Suitable conditions for this conversion are, for example, the reaction of a compound of formula (XXIa) with a compound of formula (XXV) in the presence of a catalytic system, such as that generated from $Pd_2(dba)_3$ in the presence of the phosphine ligand such as XantPhos. The reaction is conveniently conducted in a polar aprotic solvent such as THF and in the presence of a base, for example, an inorganic base such as cesium carbonate.

Compounds of formula (XXIa) wherein Ar is as previously defined and X is pyridine may be derived from a compound of formula (XXVI):

by oxidation to a compound of formula (XXVII) followed by treatment with a chlorinating agent. A suitable chlorinating reagent for the conversion of a compound of formula (XXVI) into a compound of formula (XXVII) is, for example, m-CPBA. The reaction may be effected in a halogenated solvent such as DCM and typically below RT, for example at 0° C. The subsequent chlorination step may be carried out using a reagent such a phosphorus oxychloride at an elevated temperature, for example at 100° C.

Compounds of formula (XXVI) may be obtained from the reaction of a compound of formula (XIV) as defined previously, with a compound of formula (XXVIII):

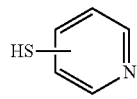

(XXVIII)

The reaction is conveniently conducted in a polar aprotic solvent such as DMF and typically in the presence of a base, for example an inorganic base such as potassium carbonate, and if necessary with cooling, for example, to 0° C.

Methods analogous to those described above may also be employed to prepare compounds of formula (I) wherein J is thienyl.

Compounds of formulae (IIIa), (IIIb) (IVa), (IVb) (V), (X), (Xa), (XI), (XIIa), (XIIb), (XIIc), (XIII) (XIV), (XVII), (XVIII), (XX), (XXII) and certain other compounds illustrated in the schemes are either commercially available, or were obtained using the cited procedures, or can be readily prepared by conventional methods by those skilled in the art. See for example Regan, J. et al.; *J. Med. Chem.*, 2003, 46:4676-4686, WO 2000/043384, WO 2007/087448 and WO 2007/089512.

Protecting groups may be required to protect chemically sensitive groups during one or more of the reactions described above, to ensure that the process is efficient. Thus if desired or necessary, intermediate compounds may be protected by the use of conventional protecting groups. Protecting groups and means for their removal are described in "Protective Groups in Organic Synthesis", by Theodora W. Greene and Peter G. M. Wuts, published by John Wiley & Sons Inc; $4^{th}$ Rev Ed., 2006, ISBN-10: 0471697540.

Novel intermediates are claimed as an aspect of the invention.

In one aspect the compounds are useful in treatment, for example COPD and/or asthma.

The p38MAPK inhibitory compounds developed to date have typically been intended for oral administration. This method of dosing involves optimization to achieve an adequate duration of action by selecting compounds that have an appropriate pharmacokinetic profile. This strategy ensures that a therapeutically effective drug concentration is established and maintained after and between doses to provide the desired clinical benefit. The inevitable consequence of this regimen is that all body tissues, especially liver and gut, are likely to be exposed chronically to therapeutically active concentrations of the drug, whether or not they are adversely affected in the diseased state.

An alternative strategy is to design treatment approaches in which the drug is dosed directly to the inflamed organ (topical therapy). While this approach is not suitable for treating all chronic inflammatory diseases, it has been extensively exploited in lung diseases (asthma, COPD), skin diseases (atopic dermatitis and psoriasis), nasal diseases (allergic rhinitis) and gastrointestinal diseases (ulcerative colitis).

In topical therapy, efficacy can be achieved either by ensuring that the drug has a sustained duration of action and is retained in the relevant organ to minimize the risk of systemic toxicity; or by producing a formulation which generates a "reservoir" of the active drug which is available to sustain the drug's desired effects. The first approach is exemplified by the anticholinergic drug tiotropium (Spiriva). This compound is administered topically to the lung as a treatment for COPD, and has an exceptionally high affinity for its target receptor resulting in a very slow off rate and a consequent sustained duration of action.

There is provided according to one aspect of the present disclosure use of a compound of formula (I) as a p38 MAP kinase inhibitor, in particular as an alpha and/or gamma p38MAPK inhibitor, for example administered topically to the lung.

In one aspect of the disclosure the compounds herein are particularly suitable for topical delivery, such as topical delivery to the lungs, in particular for the treatment of COPD.

Thus is one aspect there is provided use of compounds of formula (I) for the treatment of COPD and/or asthma, in particular COPD or severe asthma, by inhalation i.e. topical administration to the lung. Advantageously, administration to the lung allows the beneficial effects of the compounds to be realised whilst minimising the side-effects for patients.

In one aspect the compounds have a longer duration of actions than BIRB 796.

In one embodiment the compounds are suitable for sensitizing patients to treatment with a corticosteroid.

The compounds herein may also be useful for the treatment of rheumatoid arthritis.

Further, the present invention provides a pharmaceutical composition comprising a compound according to the disclosure optionally in combination with one or more pharmaceutically acceptable diluents or carriers.

Diluents and carriers may include those suitable for parenteral, oral, topical, mucosal and rectal administration.

As mentioned above, such compositions may be prepared e.g. for parenteral, subcutaneous, intramuscular, intravenous, intra-articular or peri-articular administration, particularly in the form of liquid solutions or suspensions; for oral administration, particularly in the form of tablets or capsules; for topical e.g. pulmonary or intranasal administration, particularly in the form of powders, nasal drops or aerosols and transdermal administration; for mucosal administration e.g. to buccal, sublingual or vaginal mucosa, and for rectal administration e.g. in the form of a suppository.

The compositions may conveniently be administered in unit dosage form and may be prepared by any of the methods well-known in the pharmaceutical art, for example as described in Remington's Pharmaceutical Sciences, 17th ed., Mack Publishing Company, Easton, Pa., (1985). Formulations for parenteral administration may contain as excipients sterile water or saline, alkylene glycols such as propylene glycol, polyalkylene glycols such as polyethylene glycol, oils of vegetable origin, hydrogenated naphthalenes and the like. Formulations for nasal administration may be solid and may contain excipients, for example, lactose or dextran, or may be aqueous or oily solutions for use in the form of nasal drops or metered spray. For buccal administration typical excipients include sugars, calcium stearate, magnesium stearate, pregelatinated starch, and the like.

Compositions suitable for oral administration may comprise one or more physiologically compatible carriers and/or excipients and may be in solid or liquid form. Tablets and capsules may be prepared with binding agents, for example, syrup, acacia, gelatin, sorbitol, tragacanth, or poly-vinylpyrollidone; fillers, such as lactose, sucrose, corn starch, calcium phosphate, sorbitol, or glycine; lubricants, such as magnesium stearate, talc, polyethylene glycol, or silica; and surfactants, such as sodium lauryl sulfate. Liquid compositions may contain conventional additives such as suspending agents, for example sorbitol syrup, methyl cellulose, sugar syrup, gelatin, carboxymethyl-cellulose, or edible fats; emulsifying agents such as lecithin, or acacia; vegetable oils such as almond oil, coconut oil, cod liver oil, or peanut oil; preservatives such as butylated hydroxyanisole (BHA) and butylated hydroxytoluene (BHT). Liquid compositions may be encapsulated in, for example, gelatin to provide a unit dosage form.

Solid oral dosage forms include tablets, two-piece hard shell capsules and soft elastic gelatin (SEG) capsules.

A dry shell formulation typically comprises of about 40% to 60% concentration of gelatin, about a 20% to 30% concentration of plasticizer (such as glycerin, sorbitol or propylene glycol) and about a 30% to 40% concentration of water. Other materials such as preservatives, dyes, opacifiers and flavours also may be present. The liquid fill material comprises a solid drug that has been dissolved, solubilized or dispersed (with suspending agents such as beeswax, hydrogenated castor oil or polyethylene glycol 4000) or a liquid drug in vehicles or combinations of vehicles such as mineral oil, vegetable oils, triglycerides, glycols, polyols and surface-active agents.

Suitably the compound of formula (I) is administered topically to the lung. Hence we provide according to the invention a pharmaceutical composition comprising a compound of the disclosure optionally in combination with one or more topically acceptable diluents or carriers. Topical administration to the lung may be achieved by use of an aerosol formulation. Aerosol formulations typically comprise the active ingredient suspended or dissolved in a suitable aerosol propellant, such as a chlorofluorocarbon (CFC) or a hydrofluorocarbon (HFC). Suitable CFC propellants include trichloromonofluoromethane (propellant 11), dichlorotetrafluoromethane (propellant 114), and dichlorodifluoromethane (propellant 12). Suitable HFC propellants include tetrafluoroethane (HFC-134a) and heptafluoropropane (HFC-227). The propellant typically comprises 40% to 99.5% e.g. 40% to 90% by weight of the total inhalation composition. The formulation may comprise excipients including co-solvents (e.g. ethanol) and surfactants (e.g. lecithin, sorbitan trioleate and the like). Aerosol formulations are packaged in canisters and a suitable dose is delivered by means of a metering valve (e.g. as supplied by Bespak, Valois or 3M).

Topical administration to the lung may also be achieved by use of a non-pressurised formulation such as an aqueous solution or suspension. This may be administered by means of a nebuliser. Topical administration to the lung may also be achieved by use of a dry-powder formulation. A dry powder formulation will contain the compound of the disclosure in finely divided form, typically with a mass mean diameter (MMAD) of 1-10 μm. The formulation will typically contain a topically acceptable diluent such as lactose, usually of large particle size e.g. a mass mean diameter (MMAD) of 100 μm or more. Example dry powder delivery systems include SPINHALER, DISKHALER, TURBOHALER, DISKUS and CLICKHALER.

Compounds according to the disclosure are intended to have therapeutic activity. In a further aspect, the present invention provides a compound of the disclosure for use as a medicament.

Compounds according to the disclosure may also be useful in the treatment of respiratory disorders including COPD (including chronic bronchitis and emphysema), asthma, paediatric asthma, cystic fibrosis, sarcoidosis, idiopathic pulmonary fibrosis, allergic rhinitis, rhinitis, sinusitis, especially asthma, chronic bronchitis and COPD.

Compounds of the disclosure may also re-sensitise the patient's condition to treatment with a corticosteroid, when the patient's condition has become refractory to the same.

In one embodiment a compound of formula (I) is provide for use in preventing a patient becoming refractory to treatment with a corticosteroid.

Compounds according to the disclosure are also expected to be useful in the treatment of certain conditions which may be treated by topical or local therapy including allergic conjunctivitis, conjunctivitis, allergic dermatitis, contact dermatitis, psoriasis, ulcerative colitis, inflamed joints secondary to rheumatoid arthritis or osteoarthritis.

Compounds of the disclosure are also expected to be useful in the treatment of certain other conditions including rheumatoid arthritis, pancreatitis, cachexia, inhibition of the growth and metastasis of tumours including non-small cell lung carcinoma, breast carcinoma, gastric carcinoma, colorectal carcinomas and malignant melanoma.

One or more compounds of the disclosure are believed to be useful as anti-viral agents, for example in the treatment of conditions including influenza. In particular the compounds of the present disclosure may be suitable for the use in the treatment or prevention of said viral infection and in particular may be capable of reducing viral load and/or ameliorating symptoms after infection.

Thus, in a further aspect, the present invention provides a compound as described herein for use in the treatment of the above mentioned conditions.

In a further aspect, the present invention provides use of a compound as described herein for the manufacture of a medicament for the treatment of the above mentioned conditions.

In a further aspect, the present invention provides a method of treatment of the above mentioned conditions which comprises administering to a subject an effective amount of a compound of the disclosure or a pharmaceutical composition thereof.

The word "treatment" is intended to embrace prophylaxis as well as therapeutic treatment.

A compound of the disclosure may also be administered in combination with one or more other active ingredients e.g. active ingredients suitable for treating the above mentioned conditions. For example possible combinations for treatment of respiratory disorders include combinations with steroids (e.g. budesonide, beclomethasone dipropionate, fluticasone propionate, mometasone furoate, fluticasone furoate), beta agonists (e.g. terbutaline, salbutamol, salmeterol, formoterol) and/or xanthines (e.g. theophylline).

Throughout the specification and the claims which follow, unless the context requires otherwise, the word 'comprise', and variations such as 'comprises' and 'comprising', will be understood to imply the inclusion of a stated integer, step, group of integers or group of steps but not to the exclusion of any other integer, step, group of integers or group of steps.

All patents and patent applications referred to herein are incorporated by reference in their entirety.

The application of which this description and claims forms part may be used as a basis for priority in respect of any subsequent application. The claims of such subsequent application may be directed to any feature or combination of features described herein. They may take the form of product, composition, process, or use claims and may include, by way of example and without limitation, the claims.

Where embodiments comprising certain elements are disclosed herein, the invention also extends to alternative embodiments consisting of or consisting essentially of said elements.

EXPERIMENTAL SECTION

Abbreviations used herein are defined below (Table 1). Any abbreviations not defined are intended to convey their generally accepted meaning.

TABLE 1

| | Abbreviations |
|---|---|
| AcOH | glacial acetic acid |
| aq | Aqueous |
| Ac | Acetyl |
| ATP | adenosine-5'-triphosphate |
| BALF | bronchoalveolae lavage fluid |
| Boc | tert-butoxycarbonyl |
| br | Broad |
| BSA | bovine serum albumin |
| CatCart ® | catalytic cartridge |
| CDI | 1,1-carbonyl-diimidazole |
| COPD | chronic obstructive pulmonary disease |
| d | Doublet |
| DCM | Dichloromethane |
| DIAD | Diisopropylazadicarboxylate |
| DIBAL-H | diisobutylaluminium hydride |
| DIPEA | N,N-diisopropylethylamine |
| DMF | N,N-dimethylformamide |
| DMSO | dimethyl sulfoxide |
| EDC•HCl | 1-ethyl-3-(3-dimethylaminopropyl)carbodiimide. Hydrochloride |
| (ES+) | electrospray ionization, positive mode |
| Et | Ethyl |
| EtOAc | ethyl acetate |
| FCS | foetal calf serum |
| HOBt | 1-hydroxybenzotriazole |
| hr | hour(s) |
| HRP | horseradish peroxidise |
| JNK | c-Jun N-terminal kinase |
| (M + H)+ | protonated molecular ion |
| MAPK | mitogen protein activated protein kinase |
| Me | Methyl |
| MeCN | Acetonitrile |
| MeOH | Methanol |
| MHz | Megahertz |
| min | minute(s) |
| MTT | 3-(4,5-dimethylthiazol-2-yl)-2,5-diphenyltetrazolium bromide |
| m/z: | mass-to-charge ratio |
| NMM | N-methylmorpholine; (4-methylmorpholine) |
| NMP | 1-methylpyrrolidin-2-one (N-methyl-2-pyrrolidone) |
| NMR | nuclear magnetic resonance (spectroscopy) |
| Ph | Phenyl |
| PBS | phosphate buffered saline |
| PPh$_3$ | Triphenylphosphine |
| q | Quartet |
| RT | room temperature |
| RP HPLC | reverse phase high performance liquid chromatography |
| s | Singlet |
| SCX | solid supported cation exchange (resin) |
| SDS | sodium dodecyl sulphate |
| S$_N$Ar | nucleophilic aromatic substitution |
| t | Triplet |
| TBAF | tetrabutylammonium fluoride |
| TBDMS-Cl | tert-butyldimethylchlorosilane |
| TFA | trifluoroacetic acid |
| THF | Tetrahydrofuran |
| TIPS-Cl | Chlorotriisopropylsilane |
| TMB | 3,3',5,5'-tetramethylbenzidine |
| TNFα | tumor necrosis factor alpha |
| XantPhos | 4,5-bis(diphenylphosphino)-9,9-dimethylxanthene |

General Procedures

All starting materials and solvents were either obtained from commercial sources or prepared according to the literature citation. Unless otherwise stated all reactions were stirred. Organic solutions were routinely dried over anhydrous magnesium sulfate. Hydrogenations were preformed on a Thales H-cube flow reactor under the conditions stated.

Column chromatography was performed on pre-packed silica (230-400 mesh, 40-63 µm) cartridges using the amount indicated. SCX was purchased from Supelco and treated with 1M hydrochloric acid prior to use. Unless stated otherwise the reaction mixture to be purified was first diluted with MeOH and made acidic with a few drops of AcOH. This solution was loaded directly onto the SCX and washed with MeOH. The desired material was then eluted by washing with 1% NH$_3$ in MeOH.

Preparative Reverse Phase High Performance Liquid Chromatography:

Agilent Scalar column C18, 5 µm (21.2×50 mm), flow rate 28 mL min$^{-1}$ eluting with a H$_2$O-MeCN gradient containing 0.1% v/v formic acid over 10 min using UV detection at 215 and 254 nm. Gradient information: 0.0-0.5 min; 95% H$_2$O-5% MeCN; 0.5-7.0 min; ramped from 95% H$_2$O-5% MeCN to 5% H$_2$O-95% MeCN; 7.0-7.9 min; held at 5% H$_2$O-95% MeCN; 7.9-8.0 min; returned to 95% H$_2$O-5% MeCN; 8.0-10.0 min; held at 95% H$_2$O-5% MeCN.

Analytical Methods

Reverse Phase High Performance Liquid Chromatography:

Method 1: Agilent Scalar column C18, 5 µm (4.6×50 mm) or Waters XBridge C18, 5 µm (4.6×50 mm) flow rate 2.5 mL min$^{-1}$ eluting with a H$_2$O-MeCN gradient containing either 0.1% v/v formic acid (Method 1 acidic) or NH$_3$ (Method 1 basic) over 7 min employing UV detection at 215 and 254 nm. Gradient information: 0.0-0.1 min, 95% H$_2$O-5% MeCN; 0.1-5.0 min, ramped from 95% H$_2$O-5% MeCN to 5% H$_2$O-95% MeCN; 5.0-5.5 min, held at 5% H$_2$O-95% MeCN; 5.5-5.6 min, held at 5% H$_2$O-95% MeCN, flow rate increased to 3.5 mL min$^{-1}$; 5.6-6.6 min, held at 5% H$_2$O-95% MeCN, flow rate 3.5 mL min$^{-1}$; 6.6-6.75 min, returned to 95% H$_2$O-5% MeCN, flow rate 3.5 mL min$^{-1}$; 6.75-6.9 min, held at 95% H$_2$O-5% MeCN, flow rate 3.5 mL·min$^{-1}$; 6.9-7.0 min, held at 95% H$_2$O-5% MeCN, flow rate reduced to 2.5 mL min$^{-1}$.

Method 2: Agilent Extend C18 column, 1.8 µm (4.6×30 mm) at 40° C.; flow rate 2.5-4.5 mL min$^{-1}$ eluting with a H$_2$O-MeCN gradient containing 0.1% v/v formic acid over 4 min employing UV detection at 254 nm. Gradient information: 0-3.00 min, ramped from 95% H$_2$O-5% MeCN to 5% H$_2$O-95% MeCN; 3.00-3.01 min, held at 5% H$_2$O-95% MeCN, flow rate increased to 4.5 mL min$^{-1}$; 3.01 3.50 min, held at 5% H$_2$O-95% MeCN; 3.50-3.60 min, returned to 95% H$_2$O-5% MeCN, flow rate reduced to 3.50 mL min$^{-1}$; 3.60-3.90 min, held at 95% H$_2$O-5% MeCN; 3.90-4.00 min, held at 95% H$_2$O-5% MeCN, flow rate reduced to 2.5 mL min$^{-1}$.

$^1$H NMR Spectroscopy:

$^1$H NMR spectra were acquired on a Bruker Avance III spectrometer at 400 MHz using residual undeuterated solvent as reference Compound Examples The following Intermediates used to prepare compound examples of the disclosure have been previously described or are available from commercial sources and therefore were either purchased or prepared using the procedures in the references cited below (Table 2).

TABLE 2

Commercially Available and Previously Described Intermediates.

| Intermediate | Structure | Name, LCMS Data and Reference |
|---|---|---|
| A1 | *tBu-pyrazole-NH2, N1-(4-methylphenyl)* | 3-tert-butyl-1-p-tolyl-1H-pyrazol-5-amine.<br>R$^t$ 2.46 min (Method 1 basic); m/z 230 (M + H)$^+$, (ES$^+$).<br>Cirillo, P. F. et al., WO 2000/43384, 27 Jul. 2000. |
| A2 | *tBu-pyrazole-NH2, N1-(4-CO2Me-phenyl)* | methyl 4-(5-amino-3-tert-butyl-1H-pyrazol-1-yl)benzoate.<br>R$^t$ 4.25 min (Method 1 basic); m/z 274 (M + H)$^+$, (ES$^+$).<br>Smith, R. et al., WO 2007/064872, 07 Jun. 2007. |
| A3 | *tBu-pyrazole-NH2, N1-(4-nitrophenyl)* | 3-tert-butyl-1-(4-nitrophenyl)-1H-pyrazol-5-amine.<br>R$^t$ 2.21 min (Method 2); m/z 261 (M + H)$^+$, (ES$^+$).<br>Lee, W., et al., WO 2005/110994, 24 Nov. 2005. |
| A4 | *tBu-pyrazole-NH2, N1-(3-OTBDMS-phenyl)* | 3-tert-butyl-1-(3-(tert-butyldimethylsilyloxy)phenyl)-1H-pyrazol-5-amine.<br>R$^t$ 3.89 min (Method 2); m/z 346 (M + H)$^+$, (ES$^+$).<br>Devadas, B. et al., WO 2007/091176, 16 Aug. 2007. |
| A5 | *tBu-pyrazole-NH2, N1-(3-methoxyphenyl)* | 3-tert-butyl-1-(3-methoxyphenyl)-1H-pyrazol-5-amine.<br>R$^t$ 1.51 min (Method 2); m/z 246 (M + H)$^+$, (ES$^+$).<br>Flynn, D. L. et al., WO 2006/071940, 06 Jul. 2006. |

TABLE 2-continued

Commercially Available and Previously Described Intermediates.

| Intermediate | Structure | Name, LCMS Data and Reference |
|---|---|---|
| A6 | tBu-pyrazole-NH2 with 4-OMe-phenyl | 3-tert-butyl-1-(4-methoxyphenyl)-1H-pyrazol-5-amine.<br>$R^t$ 1.32 min (Method 2); m/z 246 $(M + H)^+$, $(ES^+)$.<br>Mathias, J. P. et al., US 2006/0035922, 10 Aug. 2005. |
| A7 | tBu-pyrazole-NH2 with 4-OTBDMS-phenyl | 3-tert-butyl-1-(4-(tert-butyldimethylsilyloxy)phenyl)-1H-pyrazol-5-amine.<br>$R^t$ 2.80 min (Method 2); m/z 346 $(M + H)^+$, $(ES^+)$.<br>Mathias, J. P. et al., US 2006/0035922, 10 Aug. 2005. |
| A8 | tBu-pyrazole-NH2 with 4-SMe-phenyl | 3-tert-butyl-1-(4-(methylthio)phenyl)-1H-pyrazol-5-amine.<br>$R^t$ 1.70 min (Method 2); m/z 262 $(M + H)^+$, $(ES^+)$.<br>Mathias, J. P. et al., US 2006/0035922, 10 Aug. 2005. |
| A9 | tBu-pyrazole-NH2 with 4-SO2Me-phenyl | 3-tert-butyl-1-(4-(methylsulfonyl)phenyl)-1H-pyrazol-5-amine.<br>$R^t$ 3.65 min (Method 1 basic); m/z 294 $(M + H)^+$, $(ES^+)$.<br>Springer, C. J. et al., WO 2009/077766, 25 Jun. 2009. |
| A10 | tBu-pyrazole-NH2 with 4-Cl-phenyl | 3-tert-butyl-1-(4-chlorophenyl)-1H-pyrazol-5-amine.<br>$R^t$ 1.92 min (Method 2); m/z 250/252 $(M + H)^+$, $(ES^+)$.<br>Abraham, S. et al., WO 2009/117080, 24 Sep. 2009. |

TABLE 2-continued

Commercially Available and Previously Described Intermediates.

| Intermediate | Structure | Name, LCMS Data and Reference |
|---|---|---|
| A11 | 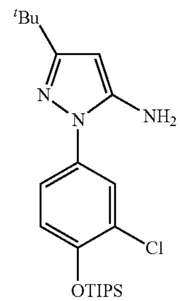 | 3-tert-butyl-1-(3-chloro-4-(triisopropylsilyloxy)phenyl)-1H-pyrazol-5-amine.<br>$R^t$ 5.84 min (Method 1 basic); m/z 422/424 $(M + H)^+$, $(ES^+)$.<br>Butcher, K. J., WO 2009/098612, 13 Aug. 2009. |
| A12 | 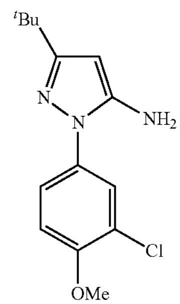 [SMILES: COc1ccc(-n2nc(C(C)(C)C)cc2N)cc1Cl] | 3-tert-butyl-1-(3-chloro-4-methoxyphenyl)-1H-pyrazol-5-amine.<br>$R^t$ 4.09 min (Method 1 basic); m/z 280/282 $(M + H)^+$, $(ES^+)$.<br>Mathias, J. P. et al., US 2006/0035922, 10 Aug. 2005. |
| A13 | 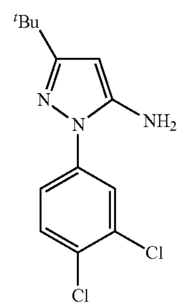 [SMILES: CC(C)(C)c1cc(N)n(-c2ccc(Cl)c(Cl)c2)n1] | 3-tert-butyl-1-(3,4-dichlorophenyl)-1H-pyrazol-5-amine.<br>$R^t$ 2.51 min (Method 2); m/z 284/286 $(M + H)^+$, $(ES^+)$.<br>Li, S. et al., WO 2008/125014, 13 Oct. 2008. |
| A14 | 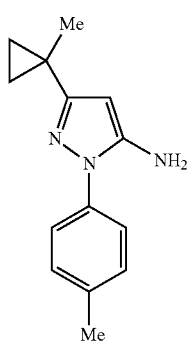 [SMILES: Cc1ccc(-n2nc(C3(C)CC3)cc2N)cc1] | 3-(1-methylcyclopropyl)-1-(p-tolyl)-1H-pyrazol-5-amine.<br>$R^t$ 3.72 min (Method 1 basic); m/z 228 $(M + H)^+$, $(ES^+)$.<br>Bastian, J. A. et al., WO 2007/053394, 10 May 2007. |
| A15 | 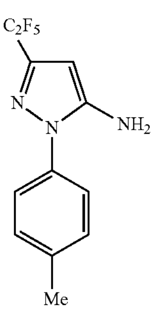 | 3-(perfluoroethyl)-1-(p-tolyl)-1H-pyrazol-5-amine.<br>$R^t$ 2.39 min (Method 2); m/z 292 $(M + H)^+$, $(ES^+)$.<br>Bastian, J. A. et al., WO 2007/053394, 10 May 2007. |

TABLE 2-continued

Commercially Available and Previously Described Intermediates.

| Intermediate | Structure | Name, LCMS Data and Reference |
| --- | --- | --- |
| A16 | 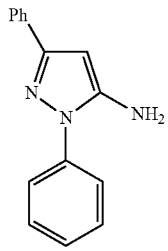 [SMILES: Nc1cc(-c2ccccc2)nn1-c1ccccc1] | 1,3-diphenyl-1H-pyrazol-5-amine. Compound is commercially available. |
| A17 | 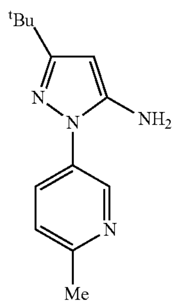 [SMILES: Cc1ccc(-n2nc(C(C)(C)C)cc2N)cn1] | 3-tert-butyl-1-(6-methylpyridin-3-yl)-1H-pyrazol-5-amine. $R^t$ 1.25 min (Method 2); m/z 231 $(M + H)^+$, $(ES^+)$. Regan, J. et al. *J. Med. Chem.*, 2003, 46, 4676-4686. |
| A18 | 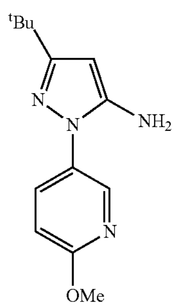 [SMILES: COc1ccc(-n2nc(C(C)(C)C)cc2N)cn1] | 3-tert-butyl-1-(6-methoxypyridin-3-yl)-1H-pyrazol-5-amine. $R^t$ 3.85 min (Method 1 basic); m/z 247 $(M + H)^+$, $(ES^+)$. Betageri, R., et al., WO 2000/55139, 21 Sep. 2000. |
| B1 | 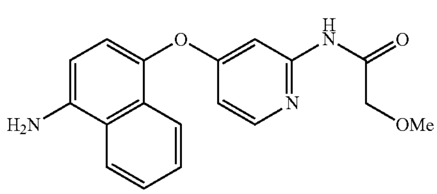 [SMILES: COCC(=O)Nc1cc(Oc2ccc(N)c3ccccc23)ccn1] | N-(4-(4-aminonaphthalen-1-yloxy)pyridin-2-yl)-2-methoxyacetamide. $R^t$ 1.56 min (Method 2); m/z 324 $(M + H)^+$ $(ES^+)$. Ito, K. et al., WO 2010/067130, 17 Jun. 2010. |
| B2 | 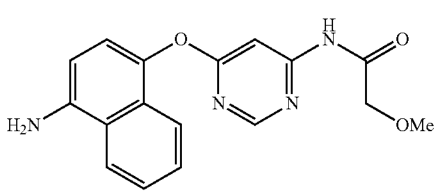 [SMILES: COCC(=O)Nc1cc(Oc2ccc(N)c3ccccc23)ncn1] | N-(6-(4-aminonaphthalen-1-yloxy)pyrimidin-4-yl)-2-methoxyacetamide. $R^t$ 1.53 min (Method 2); m/z 325 $(M + H)^+$ $(ES^+)$. Ito, K. et al., WO 2010/067130, 17 Jun. 2010. |
| C1 | 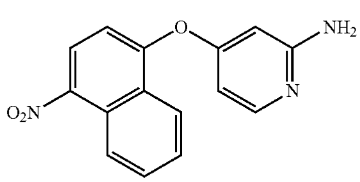 [SMILES: Nc1cc(Oc2ccc([N+](=O)[O-])c3ccccc23)ccn1] | 4-(4-nitronaphthalen-1-yloxy)pyridin-2-amine. $R^t$ 1.40 min (Method 2); m/z 282 $(M + H)^+$ $(ES^+)$. Ito, K. et al., WO 2010/067130, 17 Jun. 2010. |

TABLE 2-continued

Commercially Available and Previously Described Intermediates.

| Intermediate | Structure | Name, LCMS Data and Reference |
|---|---|---|
| D1 | 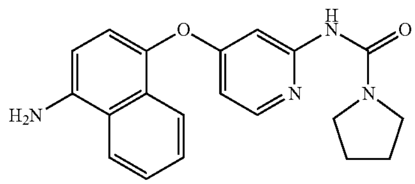 [SMILES: Nc1ccc(Oc2ccnc(NC(=O)N3CCCC3)c2)c2ccccc12] | N-(4-(4-aminonaphthalen-1-yloxypyridin-2-yl)pyrrolidine-1-carboxamide. $R^t$ 1.84 min (Method 2); m/z 379 $(M + H)^+$ $(ES^+)$. Ito, K. et al., WO 2010/067130, 17 Jun. 2010. |
| E1 | 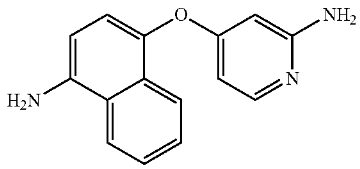 [SMILES: Nc1cc(Oc2ccc(N)c3ccccc23)ccn1] | 4-((4-aminonaphthalen-1-yl)oxy)pyridin-2-amine. $R^t$ 1.07 min (Method 2); m/z 252 $(M + H)^+$, $(ES^+)$. Ito, K. et al., WO 2010/067130, 17 Jun. 2010 |

Intermediate A19: 3-tert-Butyl-1-(3,4-dimethoxyphenyl)-1H-pyrazol-5-amine

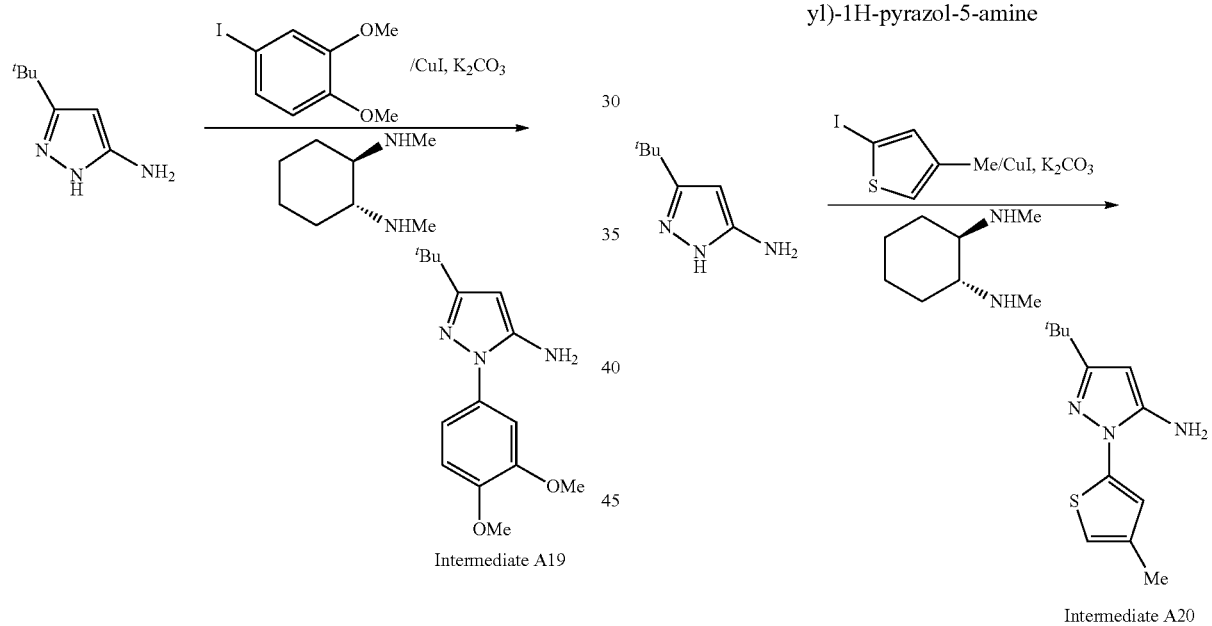

Intermediate 20: 3-tert-Butyl-1-(4-methylthiophen-2-yl)-1H-pyrazol-5-amine

To a solution of 4-iodo-1,2-dimethoxybenzene (1.10 g, 4.17 mmol) in anhydrous toluene (5.0 mL) was added 3-tert-butyl-1H-pyrazol-5-amine (638 mg, 4.58 mmol) followed by (1R,2R)—$N^1,N^2$-dimethylcyclohexane-1,2-diamine (130 µL, 0.83 mmol) and potassium carbonate (1.15 g, 8.3 mmol). The mixture was purged with $N_2$, copper(I) iodide (40 mg, 0.21 mmol) was added and the reaction mixture was heated at reflux under $N_2$ for 16 hr. The resulting mixture was cooled to RT and was partitioned between EtOAc (100 mL) and water (150 mL). The organic layer was separated and was washed with aq. citric acid solution (10% w/v, 50 mL) followed by brine (50 mL) and then dried and evaporated in vacuo. The residue was purified by flash column chromatography (SiO$_2$, 80 g, EtOAc in isohexane, 0-70%, gradient elution). The impure product so obtained was dissolved in ether (1.0 mL), isohexane (10 mL) was added and the resulting precipitate was collected by filtration to afford the title compound, Intermediate A19, as a purple solid (364 mg, 31%); $R^t$ 3.55 min (Method 1); m/z 276 $(M+H)^+$ $(ES^+)$.

To a solution of 2-iodo-4-methylthiophene (WO 2008/121666) (1.00 g, 4.50 mmol) in anhydrous toluene (15.0 mL) was added 3-tert-butyl-1H-pyrazol-5-amine (683 mg, 4.91 mmol) followed by (1R,2R)—$N^1,N^2$-dimethylcyclohexane-1,2-diamine (140 µL, 0.89 mmol) and potassium carbonate (1.30 g, 9.37 mmol). The mixture was purged with $N_2$, copper (I) iodide (42 mg, 0.22 mmol) was added and the reaction mixture was heated at reflux under $N_2$ for 16 hr during which time most of the solvent was lost. The resulting mixture was partitioned between ethyl acetate (150 mL) and water (150 mL) and the organic layer was separated and extracted with aq. citric acid solution (10% w/v, 150 mL) followed by brine (50 mL), and then dried and evaporated in vacuo. The residue was purified by flash column chromatography (SiO$_2$, 120 g, DCM, isocratic elution) to afford the title compound, Intermediate A20, as a brown solid (340 mg, 32%); R$^t$ 1.94 min (Method 2); m/z 236 (M+H)$^+$ (ES$^+$).

Intermediate A21: 3-(4-Methyltetrahydro-2H-pyran-4-yl)-1-(p-tolyl)-1H-pyrazol-5-amine

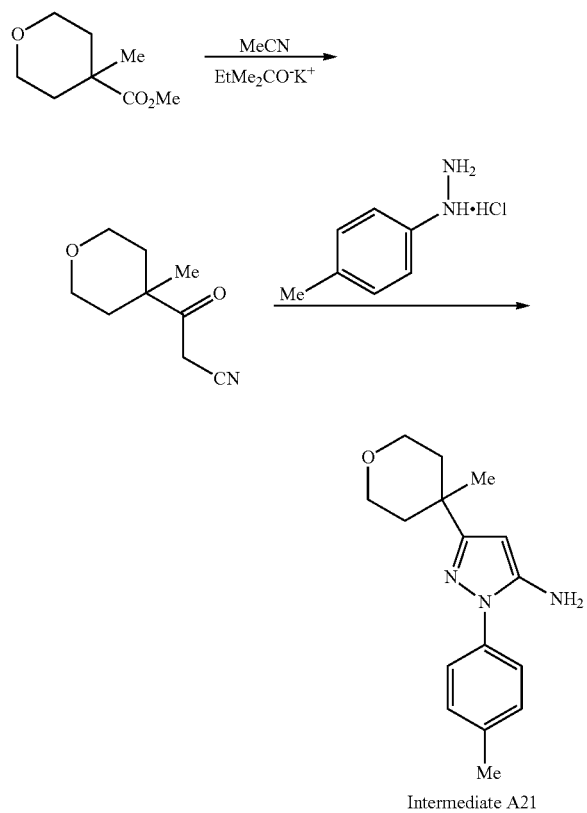

Intermediate A21

To a solution of acetonitrile (300 μL, 5.7 mmol) in THF (20 mL) at RT was added a solution of potassium 2-methylbutan-2-olate in toluene (1.7 M, 10.1 mL, 17.2 mmol) followed by the dropwise addition of methyl 4-methyltetrahydro-2H-pyran-4-carboxylate (1.36 g, 8.62 mmol) and the reaction mixture maintained at RT for 16 hr. The resulting mixture was concentrated in vacuo to a volume of ~10 mL and was then diluted with EtOH (20 mL) and p-tolylhydrazine hydrochloride (911 mg, 5.74 mmol) was added. The reaction was acidified to pH 1 by the addition of conc hydrochloric acid and the resulting heterogeneous mixture was heated to 70° C. for 5 hr, was then cooled to RT and concentrated in vacuo to a volume of ~20 mL. The mixture was diluted with water (30 mL) and adjusted to pH 12 by the addition of 2M aq NaOH and was then extracted with ethyl acetate (2×20 mL). The combined extracts were washed with brine (30 mL) and then dried and evaporated in vacuo. The residue was purified by flash column chromatography (SiO$_2$, EtOAc in isohexane, 0-50%, gradient elution) to afford the title compound, Intermediate 21, as a yellow solid (550 mg, 32%); R$^t$ 1.48 min (Method 2); m/z 272 (M+H)$^+$, (ES$^+$).

Intermediate A22: 3-tert-Butyl-1-(3-chloro-4-((triisopropylsilyloxy)methyl)phenyl)-1H-pyrazol-5-amine

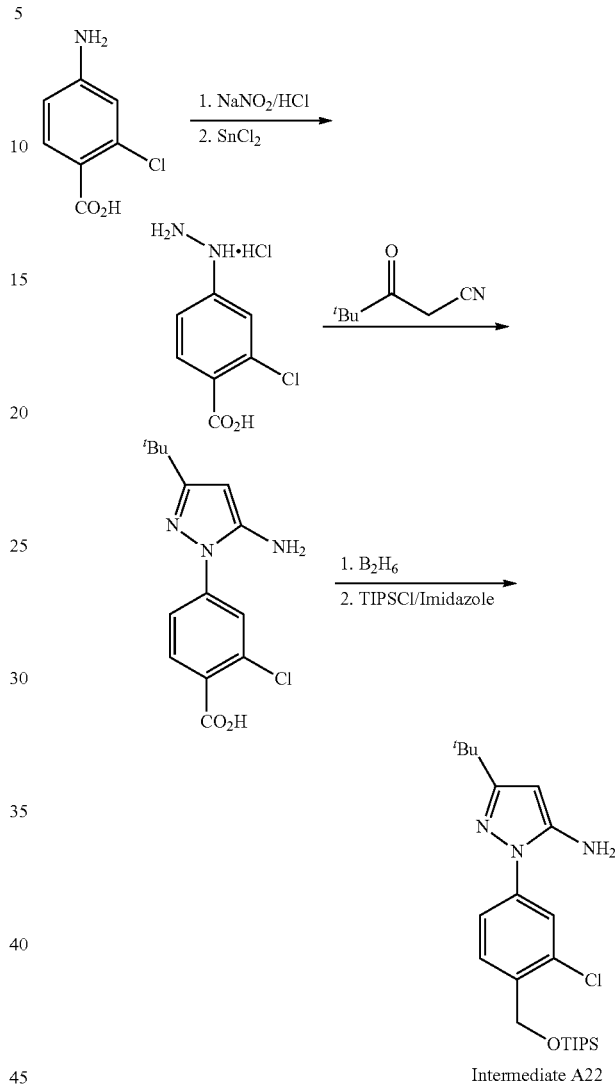

Intermediate A22

To a suspension of 4-amino-2-chlorobenzoic acid (3.00 g, 17.5 mmol) in hydrochloric acid (1.0 M, 30 mL) at 0° C. was added a solution of sodium nitrite (1.24 g, 18.0 mmol) in water (5.0 mL) over 5 min and the reaction mixture maintained at 0° C. for 5 hr. The resulting mixture was treated with tin(II) chloride (9.28 g, 49.0 mmol) in hydrochloric acid (1.0 M, 60 mL) and was warmed to RT for 64 hr. The resulting thick precipitate which formed was isolated by filtration, washed with ethanol (16 mL) and ether (15 mL) and was dried in vacuo to afford 2-chloro-4-hydrazinylbenzoic acid hydrochloride as a beige solid (3.54 g, 90% purity, 82%); R$^t$ 0.22 min (Method 2); m/z 187 (M+H)$^+$, (ES$^+$). This material was used in the subsequent step without further purification.

A suspension of 2-chloro-4-hydrazinylbenzoic acid hydrochloride (2.00 g, 90% purity, 8.10 mmol) and 4,4-dimethyl-3-oxopentanenitrile (1.24 g, 9.91 mmol) in ethanol (40 mL) containing conc hydrochloric acid (12 M, 0.83 mL, 9.0 mmol) was heated at reflux for 24 hr and then cooled to RT. The reaction mixture was basified with aq NaOH (2.0 M, 11.0 mL, 22 mmol) and was kept at RT and treated with two additional aliquots of aq NaOH (2.0 M, 2.0 mL, 4.0 mmol), after 16 hr and 18 hr. After 20 hr the mixture was concentrated in vacuo to half of its original volume, diluted with THF (10 mL) and treated with LiOH (430 mg, 19.0 mmol). The resulting mixture was maintained at RT for 16 hr and was then acidified to pH 6 with conc hydrochloric acid (12 M, 1.5 mL) and extracted with DCM (3×30 mL) The combined organic extracts were washed with brine (10 mL) and then dried and evaporated in vacuo to afford a red solid (700 mg). The remaining reaction mixture was acidified further to pH 5 with conc hydrochloric acid (12 M, 0.5 mL) and re-extracted with DCM (3×30 mL). The combined organic extracts were washed with brine (10 mL), dried and combined with the previously isolated red solid. The mixture was evaporated in vacuo to afford 4-(5-amino-3-(tert-butyl)-1H-pyrazol-1-yl)-2-chlorobenzoic acid as a yellow brown solid (1.15 g, 75% purity, 35%); $R^t$ 1.47 min (Method 1 basic); m/z 294 (M+H)$^+$, (ES$^+$). This material was used in subsequent steps without further purification To a solution of 4-(5-amino-3-(tert-butyl)-1H-pyrazol-1-yl)-2-chlorobenzoic acid (1.15 g, 75% purity, 2.9 mmol) in THF (6.0 mL) at 0° C. under $N_2$ was added a solution of borane in THF (1.0 M, 11.7 mL, 11.7 mmol) over 5 min and the reaction mixture warmed to RT for 6 hr. An additional aliquot of the borane solution (3.0 mL, 3.0 mmol) was added and the reaction mixture maintained at RT for a further 18 hr, then quenched by the addition of MeOH (30 mL) and after 10 min at RT was evaporated in vacuo. The residue was partitioned between DCM (20 mL) and brine (10 mL). The aq layer was separated and was extracted with DCM (10 mL) and the combined organic layers were dried and evaporated in vacuo to afford 3-(tert-butyl)-1-(3-chloro-4-(hydroxymethyl)phenyl)-1H-pyrazol-5-amine as a dark orange oil (1.15 g, 70% purity, 98%); $R^t$ 3.92 min (Method 1 basic); m/z 280 (M+H)$^+$, (ES$^+$). This material was used in the subsequent step without further purification To a solution of 3-(tert-butyl)-1-(3-chloro-4-(hydroxymethyl)phenyl)-1H-pyrazol-5-amine (1.15 g, 70% purity, 2.9 mmol) in dry THF (10 mL) under $N_2$ was added imidazole (320 mg, 4.7 mmol) and chlorotriisopropylsilane (970 μL, 870 mg 4.5 mmol) and the reaction mixture maintained at RT for 18 hr. The resulting mixture was diluted with DCM (5.0 mL) and was treated with an additional aliquot of chlorotriisopropylsilane (970 μL, 870 mg, 4.5 mmol) and after a further 5 hr with imidazole (320 mg, 4.7 mmol). After 20 hr the reaction mixture was treated for a third time with chlorotriisopropylsilane (200 μL, 180 mg, 0.90 mmol) and imidazole (100 mg, 1.6 mmol) and after 3 days was evaporated in vacuo. The residue was taken up into EtOAc (20 mL) and was washed with water (20 mL) and brine (10 mL) and then dried and evaporated in vacuo. The residue was purified by flash column chromatography (SiO$_2$, EtOAc in isohexane, 0-100%, gradient elution) and then by SCX capture and release to afford a blue oily liquid which comprised of a mixture of starting material and the desired product. This mixture was taken up into THF (1.0 mL) and was treated with imidazole (50 mg, 0.74 mmol) chlorotriisopropylsilane (140 μL, 130 mg, 0.65 mmol) and maintained at RT for 24 hr and then evaporated in vacuo. The residue was taken up EtOAc (10 mL) and was washed with water (10 mL) and brine (10 mL) and then dried and evaporated in vacuo. The residue was purified by flash column chromatography (SiO$_2$, 40 g, EtOAc in isohexane, 0-100%, gradient elution) to afford the title compound, Intermediate A22 as a white solid (300 mg, 24%); $R^t$ 3.42 min (Method 2); m/z 436 (M+H)$^+$, (ES$^+$).

Intermediate A23: 3-tert-Butyl-1-(3-methoxy-4-((triisopropylsilyloxy)methyl)phenyl)-1H-pyrazol-5-amine

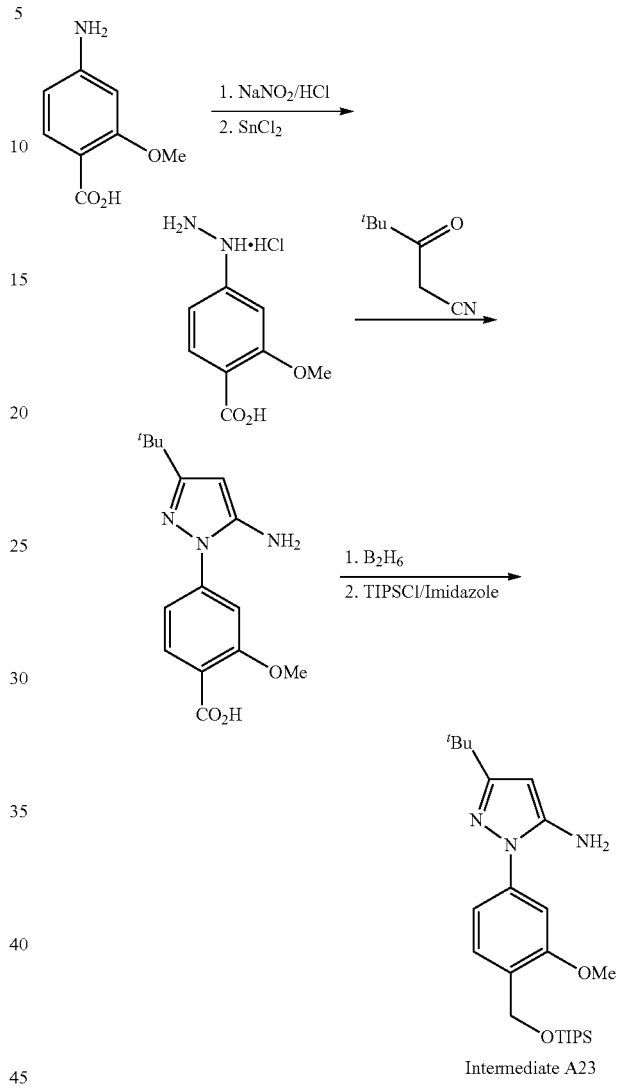

Intermediate A23

To a suspension of 4-amino-2-methoxybenzoic acid (3.00 g, 18.0 mmol) in hydrochoric acid (1.0 M, 30 mL) at 0° C. was added a solution of sodium nitrite (1.28 g, 18.5 mmol) in water (5.0 mL) over 5 min. The reaction mixture was maintained at 0° C. for 5 hr and was then treated with tin(II) chloride (9.53 g, 50.3 mmol) in hydrochloric acid (1M, 60 mL) and warmed to RT for 64 hr. A thick precipitate formed which was isolated by filtration, washed with water (50 mL) and ether (15 mL) and dried in vacuo to afford 2-methoxy-4-hydrazinylbenzoic acid hydrochloride as a beige solid (1.05 g, 90% purity, 24%); $R^t$ 0.17 min (Method 2); m/z 181 (M+H)$^+$, (ES$^+$). This material was used in the subsequent step without further purification.

A suspension of 2-methoxy-4-hydrazinylbenzoic acid hydrochloride (1.05 g, 90% purity, 4.34 mmol) and 4,4-dimethyl-3-oxopentanenitrile (664 mg, 5.31 mmol) in ethanol (20 mL) containing conc hydrochloric acid (12 M, 0.44 mL, 5.0 mmol) was heated at reflux for 28 hr and then cooled to RT. The reaction mixture was treated with aq NaOH (2.0 M, 8.6 mL, 17 mmol) and was maintained at RT for 20 hr and then concentrated to half its original volume in vacuo. Then residue was washed with DCM (2×15 mL) and the aq layer was acidified to pH 5 with conc hydrochloric acid (12 M, 1.0 mL) and re-extracted with DCM (5×30 mL). The combined organic extracts were washed with brine (10 mL) and then dried and evaporated in vacuo to afford 4-(5-amino-3-tert-butyl-1H-pyrazol-1-yl)-2-methoxybenzoic acid as a brown solid (900 mg, 61%); $R^t$ 1.47 min (Method 2); m/z 290 (M+H)$^+$, (ES$^+$).

To a solution of 4-(5-amino-3-(tert-butyl)-1H-pyrazol-1-yl)-2-methoxybenzoic acid (900 mg, 3.11 mmol) in THF (6.0 mL) at 0° C. under $N_2$ was added a solution of borane in THF (1.0 M 8.0 mL, 8.0 mmol) over 5 min and the reaction mixture warmed to RT. Additional aliquots of the borane solution were added after 22 hr (1.0 mL, 1.0 mmol) and 27 hr (1.7 mL, 1.7 mmol) and after 46 hr the reaction was quenched with MeOH (30 mL), kept at RT for 10 min and then evaporated in vacuo. The residue was partitioned between DCM (20 mL) and brine (10 mL) and the aq layer was separated and extracted with DCM (10 mL). The combined organic layers were dried and evaporated in vacuo to afford 3-tert-butyl-1-(3-chloro-4-(hydroxy methyl)phenyl)-1H-pyrazol-5-amine as a dark orange oil (840 mg, 90% purity, 88%); $R^t$ 3.62 min (Method 1 basic); m/z 276 (M+H)$^+$, (ES$^+$). This material was used in the subsequent step without further purification To a solution of 3-tert-butyl-1-(3-chloro-4-(hydroxymethyl)phenyl)-1H-pyrazol-5-amine (840 mg, 90% purity, 2.75 mmol) in dry THF (10 mL) under $N_2$ was added imidazole (240 mg, 3.5 mmol) and chlorotriisopropylsilane (720 µL, 650 mg, 3.40 mmol) and the reaction mixture kept at RT for 18 hr. The resulting mixture was diluted with DCM (5.0 mL) and was treated with a second aliquot of chlorotriisopropylsilane (720 µL, 650 mg, 3.40 mmol) and after a further 5 hr with additional imidazole (240 mg, 3.50 mmol). After 20 hr the reaction mixture was treated for a third time with chlorotriisopropylsilane (360 µL, 330 mg, 1.70 mmol) and imidazole (120 mg, 1.8 mmol) and after 3 days was evaporated in vacuo. The residue was taken up into EtOAc (50 mL) and was washed with water (20 mL) and brine (10 mL) and then dried and evaporated in vacuo. The residue was purified by flash column chromatography (SiO$_2$, 40 g, EtOAc in isohexane, 0-100%, gradient elution) and then by SCX capture and release to afford a brown oil which comprised of a mixture of starting material and the desired product. This mixture was taken up into THF (1.0 mL) and was treated with chlorotriisopropylsilane (200 µL, 200 mg, 0.30 mmol) and imidazole (75 mg, 1.1 mmol) and was maintained at RT for 24 hr and then evaporated in vacuo. The residue was partitioned between EtOAc (10 mL) and water (10 mL) and the organic phase was separated and extracted brine (10 mL) and then dried and evaporated in vacuo. The residue was purified by flash column chromatography (SiO$_2$, 40 g, EtOAc in isohexane, 0-100%, gradient elution) to afford the title compound, Intermediate A23 as a yellow oil (510 mg, 37%); $R^t$ 5.74 min (Method 1 basic); m/z 432 (M+H)$^+$, (ES$^+$).

Intermediate A24: 1-(4-(5-Amino-3-tert-butyl-1H-pyrazol-1-yl)phenyl)-N-methyl methanesulfonamide

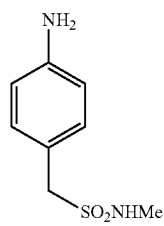

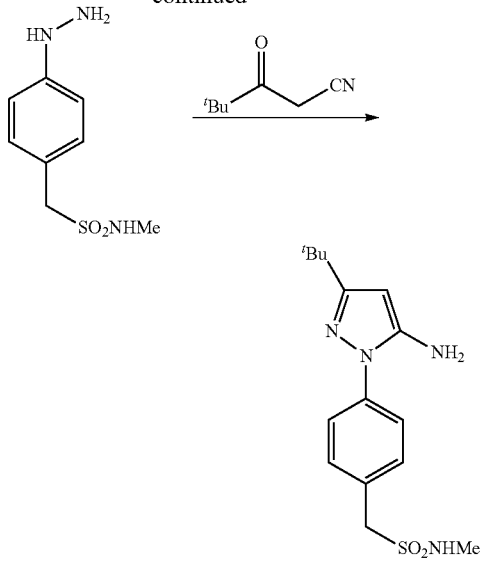

Intermediate A24

To a suspension of 1-(4-aminophenyl)-N-methylmethanesulfonamide (500 mg, 2.50 mmol) in hydrochloric acid (6 M, 10 mL) at 0° C. was added a solution of sodium nitrite (181 mg, 2.62 mmol) in water (3.0 mL) over 5 min. The reaction mixture was maintained at 0° C. for 2.5 hr, was treated with tin(II) chloride (1.33 g, 6.99 mmol) in hydrochloric acid (6M, 15 mL) and was then warmed to RT for 64 hr. The resulting mixture was basified to pH 12 with aq NaOH (6.0 M) and was extracted with EtOAc (2×100 mL). The combined organic extracts were washed with water and then dried and evaporated in vacuo to give a residue that was suspended in ethanol (10 mL) and treated with 4,4-dimethyl-3-oxopentanenitrile (160 mg, 1.3 mmol) and conc hydrochloric acid (12 M, 106 µL, 1.27 mmol). The resulting mixture was heated at reflux for 5 hr and after a further 23 hr at RT was evaporated in vacuo, to remove the ethanol and the resulting aq mixture basified with aq NaOH (2.0 M) and then extracted with DCM (2×30 mL). The combined organic extracts were dried and evaporated in vacuo to afford the title compound, Intermediate A24, as an orange solid (146 mg, 85% purity, 15%); $R^t$ 1.34 min (Method 2); m/z 323 (M+H)$^+$, (ES$^+$). This material was used in subsequent steps without further purification Intermediate A25: 3-tert-Butyl-1-(3,5-dimethoxyphenyl)-1H-pyrazol-5-amine

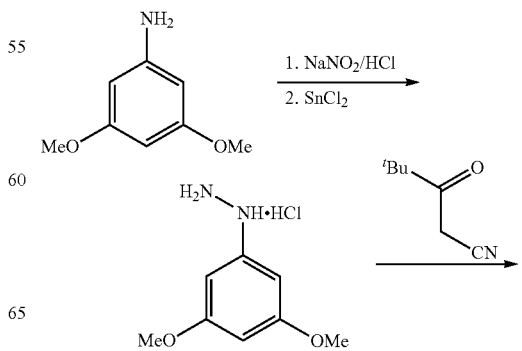

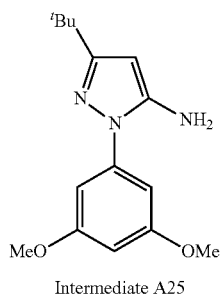

Intermediate A25

To a suspension of 3,5-dimethoxyaniline (2.0 g, 13 mmol) in hydrochloric acid (6 M, 20 mL) at 0° C. was added a solution of sodium nitrite (928 mg, 13.5 mmol) in water (5.0 mL) over 20 min and the reaction mixture maintained at 0° C. for 1 hr. The mixture was treated with tin(II) chloride (6.93 g, 36.6 mmol) in hydrochloric acid (6M, 40 mL) and was then warmed to RT during which time a solid slowly precipitated. After 64 hr the solid was isolated by filtration and washed with water (5.0 mL) and then dissolved in MeOH (2.0 mL). The solution was dried and evaporated in vacuo to afford 3,5-dimethoxyphenylydrazine hydrochloride as a beige solid (1.12 g, 80% purity, 34%); $R^t$ 0.45 min (Method 2); m/z 169 (M+H)$^+$, (ES$^+$).

To a solution of 4,4-dimethyl-3-oxopentanenitrile (754 mg, 6.02 mmol) and conc hydrochloric acid (12 M, 500 µL, 6.0 mmol) in EtOH (25 mL) was added 3,5-dimethoxyphenylhydrazine hydrochloride (1.12 g, 5.47 mmol) and the reaction mixture heated at reflux for 1 hr and then cooled to RT. After 23 hr the reaction mixture was diluted with saturated aq. NaHCO$_3$ (50 mL) then extracted with DCM (4×50 mL). The combined organic extracts were dried and evaporated in vacuo and the residue was purified by flash column chromatography (SiO$_2$, 40 g, EtOAc in isohexane, 0-100%, gradient elution) and then by SCX capture and release to afford the title compound, Intermediate A25, as a dark orange solid (400 mg, 26%); $R^t$ 1.70 min (Method 2); m/z 276 (M+H)$^+$, (ES$^+$).

Intermediate A26: 3-tert-Butyl-1-thiophen-2-yl)-1H-pyrazol-5-amine

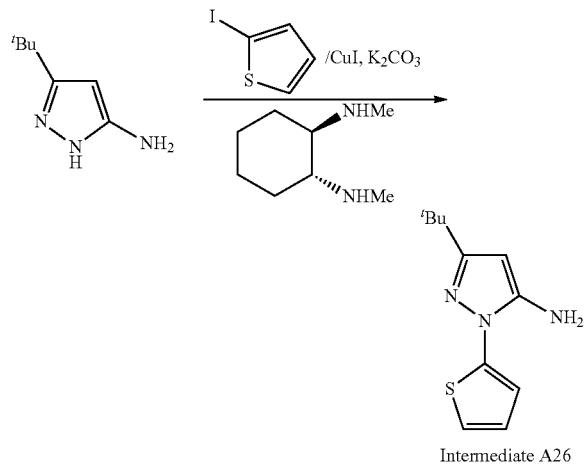

Intermediate A26

To a solution of 2-iodothiophene (1.46 mL, 3.00 g, 14.3 mmol) in anhydrous toluene (15.0 mL) was added 3-tert-butyl-1H-pyrazol-5-amine (2.19 g, 15.7 mmol) followed by (1R,2R)—N$^1$,N$^2$-dimethylcyclohexane-1,2-diamine (450 µL, 2.86 mmol) and potassium carbonate (4.15 g, 30.0 mmol). The mixture was purged with N$_2$, copper(I) iodide (136 mg, 0.714 mmol) was added and the reaction mixture was heated at reflux under N$_2$ for 16 hr during which time most of the solvent was lost. The resulting mixture was cooled to RT and was partitioned between ethyl acetate (150 mL) and water (150 mL). The organic layer was separated and extracted with aq. citric acid solution (10% w/v, 150 mL) followed by brine (50 mL) and was then dried and evaporated in vacuo. The residue was purified by flash column chromatography (SiO$_2$, 120 g, DCM, isocratic elution) to afford the title compound, Intermediate A26, as a brown solid (1.17 g, 36%); $R^t$ 1.67 min (Method 2); m/z 222 (M+H)$^+$ (ES$^+$).

Intermediate A27: 3-tert-Butyl-1-(4-(trifluoromethoxy)phenyl)-1H-pyrazol-5-amine

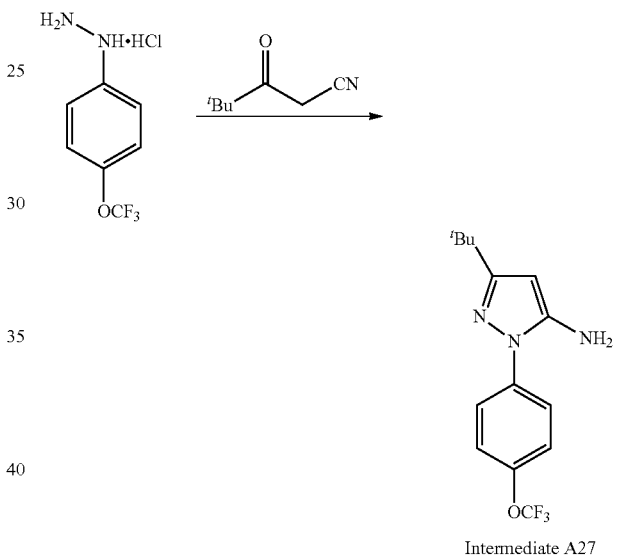

Intermediate A27

A solution of (4-(trifluoromethoxy)phenyl)hydrazine hydrochloride (1.83 g, 8.01 mmol) and 4,4-dimethyl-3-oxopentanenitrile (1.10 g, 8.81 mmol) in a mixture of conc hydrochloric acid (12 M, 2.0 mL) and EtOH (20 mL) was heated at reflux for 18 hr. The mixture was cooled to RT and was partitioned between aq. NaOH (2.0 M, 50 mL) and ether (100 mL). The organic layer was separated and was washed with brine (100 mL) and then dried and evaporated in vacuo to afford the title compound, Intermediate A27, as a yellow solid (2.22 g, 91%); $R^t$ 2.29 min (Method 2); m/z 300 (M+H)$^+$, (ES$^+$).

Intermediate A28: 3-Cyclopropyl-1-p-tolyl-1H-pyrazol-5-amine

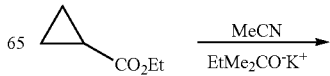

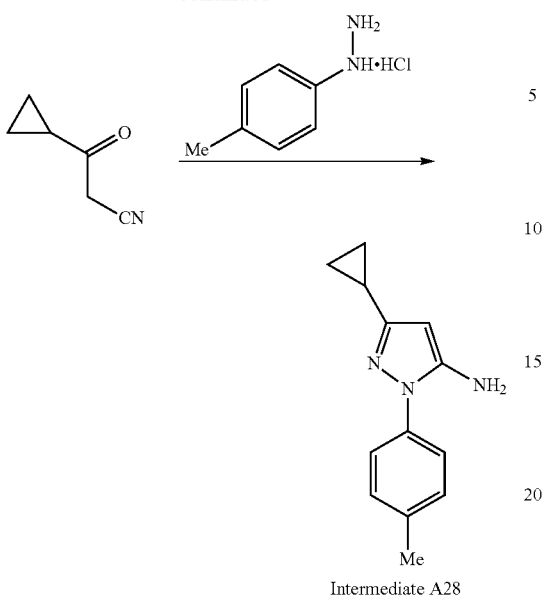

Intermediate A28

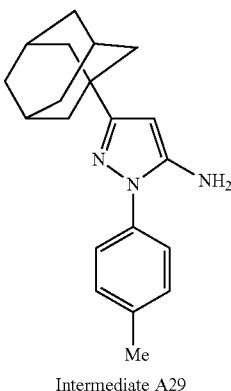

Intermediate A29

To a solution of acetonitrile (500 μL, 390 mg, 9.6 mmol) in THF (30 mL) at RT was added a solution of potassium 2-methylbutan-2-olate in toluene (1.7 M, 17.0 mL, 29.0 mmol) followed by the dropwise addition of ethyl cyclopropanecarboxylate (4.56 mL, 4.37 g, 38.0 mmol) and the reaction mixture maintained at RT for 16 hr. The resulting mixture was concentrated in vacuo to a volume of ~15 mL and was then diluted with EtOH (20 mL) and p-tolylhydrazine hydrochloride (1.52 g, 9.57 mmol) was added. The mixture was acidified to pH 1 by the addition of conc hydrochloric acid and the resulting heterogeneous mixture was heated to 70° C. for 2 hr, then cooled to RT and concentrated in vacuo to a volume of ~20 mL. The mixture was diluted with water (30 mL) and was adjusted to pH 12 by the addition of 2M aq NaOH and extracted with diethyl ether (2×20 mL). The combined organic extracts were washed with brine (30 mL) and then dried and evaporated in vacuo. The residue was triturated with isohexane (20 mL) to afford the title compound, Intermediate A28, as a beige solid (1.60 g, 77%); $R^t$ 3.35 min (Method 1 basic); m/z 214 (M+H)$^+$, (ES$^+$).

Intermediate A29: 3-(Adamantan-1-yl)-1-p-tolyl-1H-pyrazol-5-amine

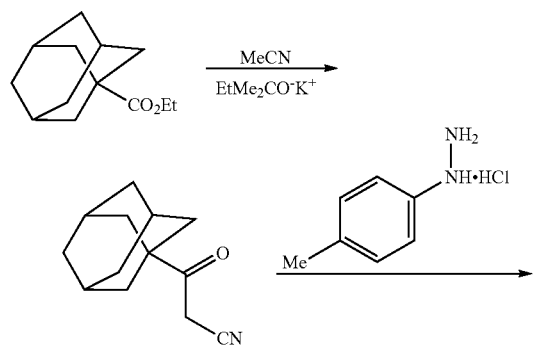

To a solution of acetonitrile (200 μL, 160 mg, 1.60 mmol) in THF (10 mL) at RT was added a solution of potassium 2-methylbutan-2-olate in toluene (1.7 M, 6.7 mL, 11 mmol) followed by the dropwise addition of ethyl adamantane-1-carboxylate (798 mg, 3.8 mmol) and the reaction mixture maintained at RT for 16 hr. The resulting mixture was concentrated in vacuo to a volume of ~10 mL and was then diluted with EtOH (10 mL), treated with p-tolylhydrazine hydrochloride (607 mg, 3.83 mmol) and was acidified to pH 1 by the addition of conc hydrochloric acid. The resulting heterogeneous mixture was heated to 70° C. for 2 hr, was cooled to RT and concentrated in vacuo to a volume of ~10 mL. The mixture was diluted with water (30 mL) and was adjusted to pH 12 by the addition of 2M aq NaOH and was then extracted with EtOAc (2×20 mL). The combined organic extracts were washed with brine (30 mL), dried, and then evaporated in vacuo. The residue was purified by flash column chromatography (SiO$_2$, EtOAc in isohexane, 0-50%, gradient elution) and the impure product so obtained was triturated with isohexane (20 mL) to afford the title compound, Intermediate A29, as an impure beige solid (730 mg, 65% purity, 40%) containing approximately 35% w/w 3-(adamantan-1-yl)-3-oxopropanenitrile; $R^t$ 4.92 min (Method 1 basic); m/z 308 (M+H)$^+$, (ES$^+$). This material was used in subsequent steps without further purification.

Intermediate A30:
1-p-Tolyl-3-(trifluoromethyl)-1H-pyrazol-5-amine

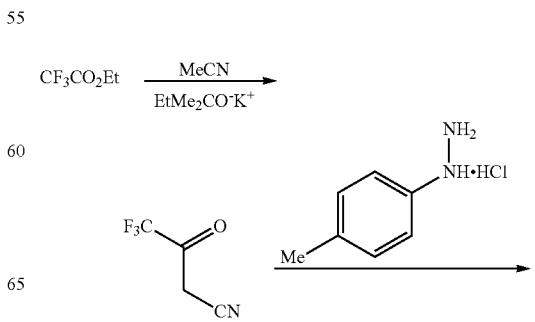

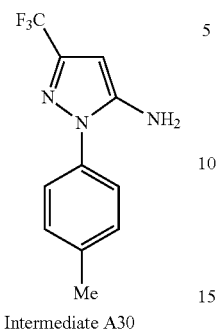

Intermediate A30

To a mixture of acetonitrile (500 µL, 0.39 g, 9.6 mmol) in THF (30 mL) at RT was added a solution of potassium 2-methylbutan-2-olate in toluene (1.7 M, 17 mL, 29 mmol) followed by the dropwise addition of ethyl 1,1,1-trifluoroacetate (5.44 g, 38.3 mmol) and the reaction mixture maintained at RT for 16 hr. The resulting mixture was concentrated in vacuo to a volume of ~10 mL and was then diluted with EtOH (20 mL), treated with p-tolylhydrazine hydrochloride (1.52 g, 9.57 mmol) and was acidified to pH 1 by the addition of conc hydrochloric acid. The resulting heterogeneous mixture was heated to 70° C. for 3 hr, was then cooled to RT and concentrated in vacuo to a volume of ~20 mL. The mixture was diluted with water (30 mL), adjusted to pH 12 by the addition of 2M aq NaOH and was then extracted with EtOAc (2×20 mL). The combined organic extracts were washed with brine (30 mL) and then dried and evaporated in vacuo. The residue was purified by flash column chromatography (SiO$_2$, EtOAc in isohexane, 0-50%, gradient elution) to afford the title compound, Intermediate A30, as a beige solid (580 mg, 25%); R$^t$ 2.11 min (Method 2); m/z 228 (M+H)$^+$, (ES$^+$).

Intermediate A31: 3-(Tetrahydro-2H-pyran-4-yl)-1-p-tolyl-1H-pyrazol-5-amine

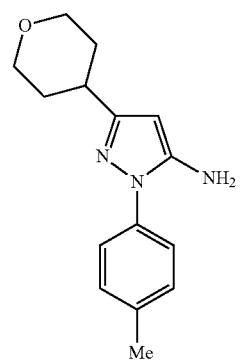

Intermediate A31

To a mixture of acetonitrile (500 µL, 390 mg, 9.60 mmol) in THF (30 mL) at RT was added a solution of potassium 2-methylbutan-2-olate in toluene (1.7 M, 17.0 mL, 29.0 mmol) followed by the dropwise addition of methyl tetrahydro-2H-pyran-4-carboxylate (5.1 mL, 5.5 g, 38 mmol) and the reaction mixture maintained at RT for 16 hr. The resulting mixture was concentrated in vacuo to a volume of ~20 mL, was diluted with EtOH (20 mL) and treated with p-tolylhydrazine hydrochloride (1.52 g, 9.57 mmol) and was acidified to pH 1 by the addition of conc hydrochloric acid. The resulting heterogeneous mixture was heated to 70° C. for 2 hr, then cooled to RT and concentrated in vacuo to a volume of ~20 mL. The residue was diluted with water (30 mL), adjusted to pH 12 by the addition of 2M aq NaOH and the mixture extracted with EtOAc (2×20 mL). The combined extracts were washed with brine (30 mL) and then dried and evaporated in vacuo. The residue was triturated with isohexane to afford the title compound, Intermediate A31, as a pale brown solid (1.94 g, 78%); R$^t$ 1.28 min (Method 2); m/z 258 (M+H)$^+$, (ES$^+$).

Intermediate A32: 3-(1-Methylcyclohexyl)-1-p-tolyl-1H-pyrazol-5-amine

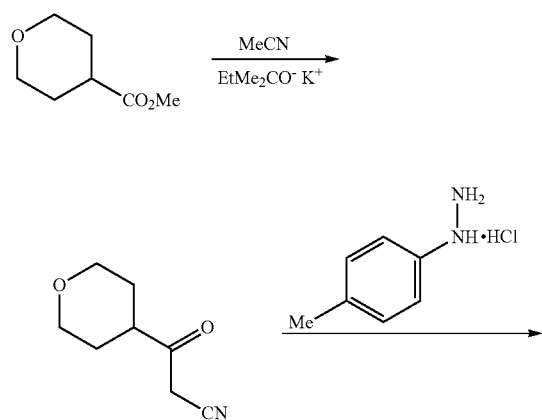

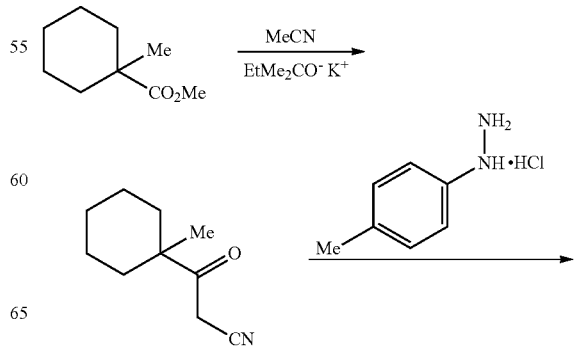

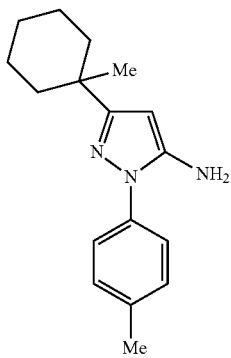

Intermediate A32

To a mixture of acetonitrile (500 µL, 10.0 mmol) in THF (30 mL) at RT was added a solution of potassium 2-methylbutan-2-olate in THF (1.7 M, 16.9 mL, 28.7 mmol), followed by methyl 1-methylcyclohexanecarboxylate (2.24 g, 14.4 mmol) and the reaction mixture maintained at RT for 17 hr and then concentrated to ~20 mL in vacuo. The residue was diluted with EtOH (20 mL), treated with p-tolylhydrazine hydrochloride (1.52 g, 9.57 mmol) and the resulting mixture acidified to pH1 by the addition of conc hydrochloric acid and then heated to 70° C. for 5 hr. The mixture was cooled to RT for 16 hr and concentrated to ~20 mL in vacuo, diluted with water (30 mL) and was then basified to pH 12 by the addition of 2M aq NaOH. The resulting solution was extracted with EtOAc (2×20 mL) and the combined organic extracts were washed with brine (30 mL) and then dried and evaporated in vacuo. The residue was purified by flash column chromatography ($SiO_2$, EtOAc in isohexane, 0-20%, gradient elution) to afford the title compound, Intermediate A33, as a yellow oil, (~50% purity, containing 3-(1-methylcyclohexyl)-3-oxopropanenitrile) (1.30 g, 25%); $R^t$ 1.97 min (Method 2); m/z 270 $(M+H)^+$ $(ES^+)$. The material was used in subsequent reactions without further purification.

Intermediate B3: N-(4-((4-Amino-2,3-dimethylphenoxy)methyl)pyridin-2-yl)-2-methoxyacetamide

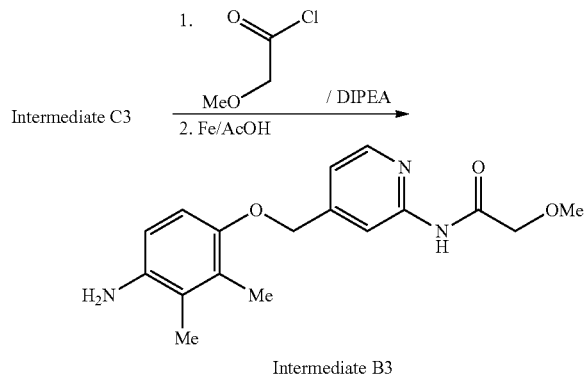

Intermediate B3

To a stirred suspension of Intermediate C3 (540 mg, 1.98 mmol) and DIPEA (690 µL, 510 mg, 4.00 mmol) in dry THF (15 mL) at 0° C. was added, dropwise, 2-methoxyacetyl chloride (270 µL, 320 mg, 3.00 mmol) and the resulting mixture then warmed to RT for 1 hr. The reaction was treated with a solution of $NH_3$ in MeOH (1.0 M, 5.0 mL) and after 1 hr at RT the mixture was partitioned between DCM (50 mL) and brine (25 mL) The organic extract was separated and washed with brine (25 mL) and then dried and evaporated in vacuo. The residue was purified by flash column chromatography ($SiO_2$, 40 g, MeOH in DCM, 0-5%, gradient elution and then $SiO_2$, 40 g, EtOAc in DCM, 0-100%, gradient elution) to afford N-(4-((2,3-dimethyl-4-nitrophenoxy)methyl)pyridin-2-yl)-2-methoxyacetamide as a pale green solid (460 mg, 66%); Rt 4.62 min (Method 1 basic); m/z 346 (M+H)+ (ES+).

A suspension of the nitroarene obtained above (460 mg, 1.30 mmol) and iron powder (446 mg, 7.99 mmol) in AcOH (5.0 mL) was heated to 60° C. for 35 min, cooled to RT for 16 hr and then re-heated to 60° C. for a further 40 min. The resulting mixture was cooled to RT and filtered through a pad of celite. The pad was washed sequentially with DCM (10 mL) and with MeOH (10 mL) and the filtrate and washings were combined and evaporated in vacuo. The residue was co-evaporated with toluene (2×50 mL) and then purified by flash column chromatography ($SiO_2$, 40 g, MeOH in DCM, 0-4%, gradient elution) to provide the title compound, Intermediate B3 as a yellow solid (250 mg, 50%); Rt 1.11 min (Method 2); m/z 316 (M+H)+(ES+).

Intermediate C2:
4-(2,3-Dimethyl-4-nitrophenoxy)pyridin-2-amine

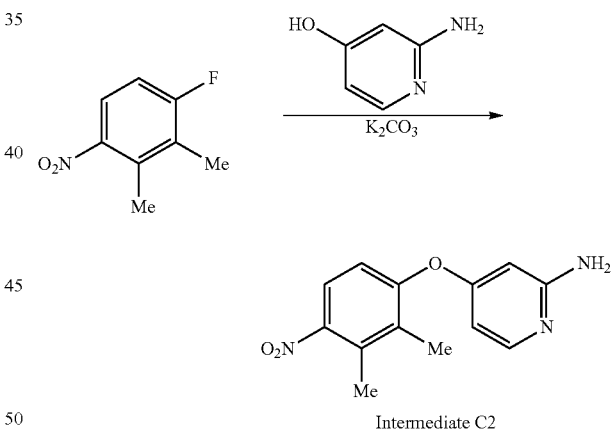

Intermediate C2

To a stirred solution of 2-aminopyridin-4-ol (600 mg, 5.5 mmol) and 1-fluoro-2,3-dimethyl-4-nitrobenzene (570 mg, 3.37 mmol) in DMSO (4.0 mL) was added $K_2CO_3$ (1.00 g, 7.20 mmol) and the reaction mixture heated to 75° C. for 3 days. The resulting mixture was cooled to RT and was partitioned between water (50 mL) and EtOAc (75 mL). The aq layer was separated and extracted with EtOAc (75 mL) and the combined organic extracts were washed with water (3×50 mL) and brine (50 mL) and then dried and evaporated in vacuo. The residue was recrystallized from DCM to afford the title compound, Intermediate C2, as a tan solid (25 mg, 28%): $R^t$ 1.40 min (Method 2); m/z 260 $(M+H)^+$ $(ES^+)$.

Intermediate C3: 4-((2,3-Dimethyl-4-nitrophenoxy)methyl)pyridin-2-amine

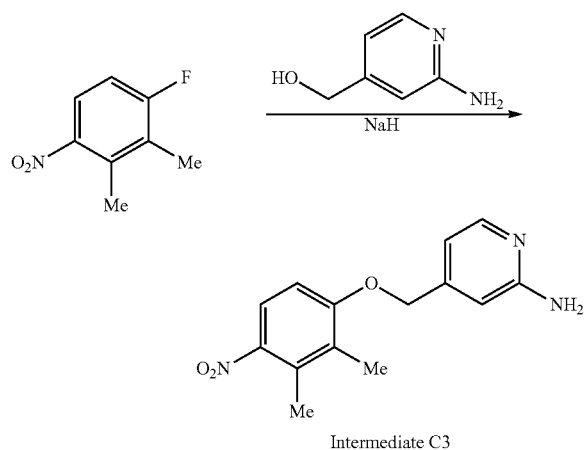

Intermediate C3

To a stirred solution of (2-aminopyridin-4-yl)methanol (1.33 g, 10.8 mmol) in DMF (10 mL) at 0° C. was added sodium hydride (60% dispersion in mineral oil, 537 mg, 13.4 mmol) and the reaction mixture maintained at 0° C. for 5 min and then warmed to RT for 1 hr. The mixture was re-cooled to 0° C., treated with a solution of 1-fluoro-2,3-dimethyl-4-nitrobenzene (2.00 g, 12.0 mmol) in DMF (5.0 mL) and after 2 min was warmed to RT. After 20 hr the reaction mixture was diluted with saturated aq. NH$_4$Cl (50 mL) and extracted with EtOAc (2×100 mL) and then ether (100 mL). The combined organic extracts were dried and evaporated in vacuo to afford a red oil. The residue was diluted with acetonitrile (50 mL), upon which a brown precipitate formed. The precipitate was removed by filtration and the filtrate was evaporated in vacuo. This residue was purified by flash column chromatography (SiO$_2$, 80 g, MeOH in DCM, 0-5%, gradient elution) to afford the title compound, Intermediate C3, as a yellow solid (1.19 g, 39%); R$^t$ 1.35 (Method 2); m/z 274 (M+H)$^+$ (ES$^+$).

Intermediate D2: 1-(4-((4-Aminonaphthalen-1-yl)oxy)pyridin-2-yl)-3-methyl urea

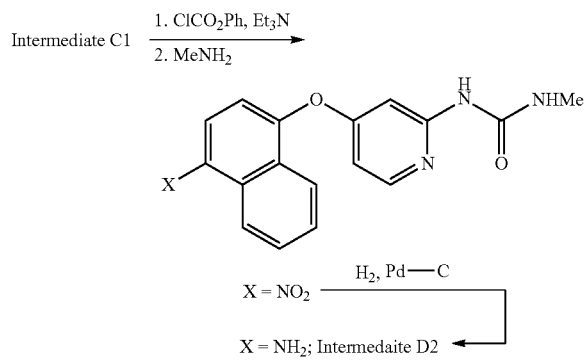

To a solution of Intermediate C1 (3.00 g, 11.0 mmol) and Et$_3$N (4.50 mL, 3.20 g, 32.0 mmol) in DCM (3.0 mL) was added phenyl carbonochloridate (3.40 mL, 4.20 g, 27.0 mmol) and the reaction mixture maintained at RT for 72 hr and then treated with additional aliquots of Et$_3$N (4.50 mL, 3.20 g, 32.0 mmol) and phenyl carbonochloridate (3.40 mL, 4.20 g, 27.0 mmol). After 1 hr at RT a solution of methylamine in THF (2 M, 27 mL, 54 mmol) was added and after a further 1 hr the reaction was quenched by addition of NH$_3$ (1% w/v in MeOH, 20 mL), kept at RT for 10 min and the volatiles evaporated in vacuo. The residue was partitioned between EtOAc (100 mL) and water (100 mL) and the aq. layer was separated and extracted with EtOAc (50 mL). The combined organic extracts were washed with brine (50 mL) and then dried and evaporated in vacuo. The residue was purified by flash column chromatography (SiO$_2$, 120 g, EtOAc in isohexane, 0-100%, gradient elution). The crude product so obtained was taken up into DCM (60 mL), diluted with ether (200 mL) and the resulting precipitate was collected by filtration. The retained aq layer (from the reaction work-up) was kept at RT for 7 days during with time a yellow solid was produced. This material was isolated by filtration and taken up into a mixture of DCM and MeOH (2:3 v/v, 50 mL) and then diluted with ether (100 mL). The resulting precipitate was collected by filtration and combined with the previously isolated material to afford 1-methyl-3-(4-(4-nitronaphthalen-1-yloxy)pyridin-2-yl)urea as a yellow solid (1.22 g, 33%); R$^t$ 1.90 min (Method 2); m/z 339 (M+H)$^+$ (ES$^+$).

A solution of 1-methyl-3-(4-(4-nitronaphthalen-1-yloxy)pyridin-2-Aurea (1.20 g, 3.60 mmol) in a mixture of MeOH (70 mL), DCM (20 mL), THF (200 mL) and AcOH (20 mL) was subjected to hydrogenation by passage through a Thales H-cube (1.0 mL min$^{-1}$, 50° C., 55 mm, 10% Pt—C Cat-Cart, full hydrogen mode). The reaction mixture was evaporated in vacuo and the residue was co-evaporated with toluene (mL) to afford the title compound, Intermediate D2, as a purple solid (1.02 g, 85% purity, 79%); R$^t$ 4.18 min (Method 1 basic); m/z 309 (M+H)$^+$ (ES$^+$). This material was used in subsequent reactions without further purification.

Intermediate D3: 1-(4-((4-Aminonaphthalen-1-yl)oxy)pyridin-2-yl)-3-cyclopropylurea

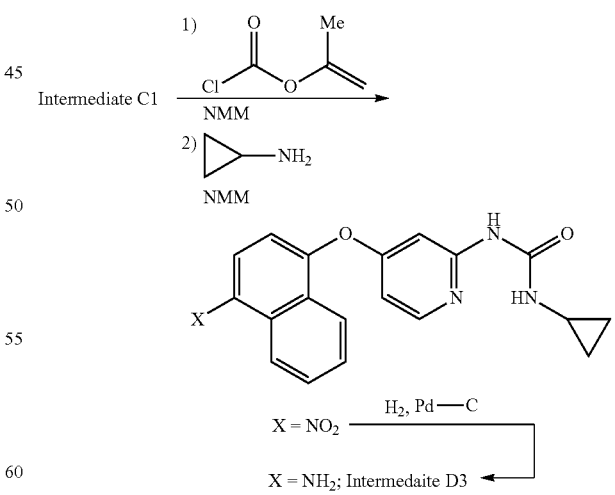

To a suspension of Intermediate C1 (250 mg, 0.89 mmol) and NMM (145 µL, 1.33 mmol) in THF (8.0 mL) under N$_2$ at −78° C. was added dropwise a solution of prop-1-en-2-yl carbonochloridate (145 µL, 1.33 mmol) in THF (3.0 mL). The mixture was warmed to RT for 15 hr and the reaction was then quenched by the addition of MeOH (2.0 mL). After a further 1 hr the resulting mixture was evaporated in vacuo and the residue was partitioned between EtOAc (10 mL) and water (10 mL). The organic layer was separated and was washed with brine (10 mL) and then dried and evaporated in vacuo. The yellow solid residue so obtained was found to comprise of a mixture of the anticipated product: prop-1-en-2-yl 4-(4-nitronaphthalen-1-yloxy)pyridin-2-ylcarbamate (Component 1) and the corresponding bis acylated amine: N,N-di(prop-1-en-2-yloxycarbonyl)-4-((4-nitronaphthalen-1-yl)oxy)pyridin-2-amine (Component 2) (0.39 g,); Component 1: $R^t$ 2.56 min (7%) (Method 2); m/z 366 (M+H)$^+$ (ES$^+$); Component 2: $R^t$ 2.67 min (89%) (Method 2); m/z 450 (M+H)$^+$ (ES$^+$). This mixture was used directly in the next reaction without further purification.

To a solution of the mixture described above (195 mg) and NMM (6 µL, 0.06 mmol) in dry THF (1.5 mL) was added cyclopropanamine (185 µL, 2.67 mmol) and the reaction mixture maintained at RT for 15 min and then heated to 55° C. for 16 hr. The mixture was cooled to RT and was evaporated in vacuo to provide a residue that was triturated with EtOAc (2.0 mL) to afford 1-cyclopropyl-3-(4-((4-nitronaphthalen-1-yl)oxy)pyridin-2-yl)urea as a yellow solid (118 mg, 71%, over two steps); $R^t$ 2.17 min (Method 2); m/z 365 (M+H)$^+$ (ES$^+$).

A solution of 1-cyclopropyl-3-(4-((4-nitronaphthalen-1-yl)oxy)pyridin-2-yl)urea (118 mg, 0.324 mmol) in a mixture of MeOH (20 mL) and AcOH (0.5 mL) was subjected to hydrogenation by passage through a Thales H-cube (1.0 mL min$^{-1}$, 25° C., 70 mm, 10% Pt—C Cat-Cart, full hydrogen mode). The reaction mixture was evaporated in vacuo and the residue was partitioned between DCM (20 mL) and saturated aq. NaHCO$_3$ (10 mL). The organic phase was separated and was washed with brine (10 mL), and then dried and evaporated in vacuo to afford the title compound, Intermediate D3, as a brown solid (90 mg, 83%); $R^t$ 1.52 min (Method 2); m/z 335 (M+H)$^+$ (ES$^+$).

Intermediate D4: 3-(4-(4-Aminonaphthalen-1-yloxy)pyridin-2-yl)-1,1-dimethylurea

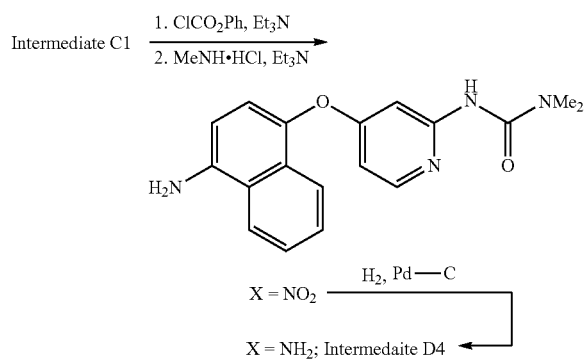

To a solution of phenyl carbonochloridate (3.7 mL, 29 mmol) and Et$_3$N (5.0 mL, 36 mmol) in DCM (45 mL) was added Intermediate C1, (4.00 g, 14.0 mmol) and the mixture maintained at RT for 2 hr. An additional aliquot of phenyl carbonochloridate (500 µL, 4.0 mmol) was added and after 1 hr the reaction mixture was diluted with DCM (30 mL) and treated with Et$_3$N (12.0 ml, 85.0 mmol) and dimethylamine hydrochloride (5.80 g, 71.0 mmol). The resulting mixture was maintained at RT for 2 hr, warmed to 30° C. for 1 hr and then returned to RT for a further 16 hr. The reaction was quenched by the addition of MeOH (30 mL) and after 30 min was evaporated in vacuo to provide a residue that was partitioned between DCM (400 mL) and 1M aq HCl (100 mL). The organic layer was separated and was washed with sat. aq. NaHCO$_3$ (100 mL), water (100 mL), and brine (100 mL) and then dried and evaporated in vacuo. The residue was triturated with a mixture of Et$_2$O/MeOH (9:1 v/v, 30 mL) to afford 1,1-dimethyl-3-(4-(4-nitronaphthalen-1-yloxy)pyridin-2-yl)urea as a bright yellow solid (3.8 g, 74%); $R^t$ 1.77 min (Method 2); m/z 353 (M+H)$^+$ (ES$^+$).

A suspension of the nitroarene obtained above (1.50 g, 4.30 mmol) and palladium on carbon (10% w/w Pd, 150 mg, 0.14 mmol) in DMF (15.0 mL) was stirred vigorously under an atmosphere of hydrogen. After 20 hr the reaction vessel was purged with N$_2$ and the reaction mixture was filtered through celite. The celite pad was washed with DCM (30 mL) and the combined filtrate and washings were evaporated in vacuo. The residue was triturated with ether (10 mL) to provide the title compound, Intermediate D4, as a dark yellow solid (950 mg, 66%); $R^t$ 1.31 min (Method 2); m/z 323 (M+H)$^+$ (ES$^+$).

Intermediate D5: N-(4-(4-aminonaphthalen-1-yloxy)pyridin-2-yl)morpholine-4-carboxamide

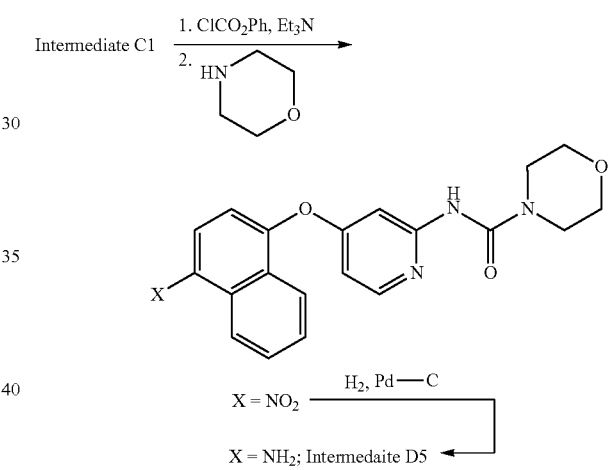

To a solution of Intermediate C1 (3.0 g, 11 mmol) and Et$_3$N (3.0 mL, 21 mmol) was added phenyl carbonochloridate (1.5 mL, 12 mmol) and the mixture maintained at RT for 2 hr. An additional aliquot of phenyl carbonochloridate (0.75 mL, 6.0 mmol) was added and after a further 1 hr, morpholine (2.8 mL, 32 mmol) was added and the reaction mixture kept at RT for 16 hr. The mixture was diluted with THF (50 mL) and DCM (90 mL) and additional morpholine (2.8 mL, 32 mmol) was added. After a further 64 hr the reaction mixture was filtered and the filtrate was evaporated in vacuo. The residue was partitioned between DCM (10 mL) and saturated aq. NH$_4$Cl and the aq. layer was separated and extracted with DCM (3×10 mL). The combined organic extracts were dried and evaporated in vacuo and the residue was purified by flash column chromatography (SiO$_2$, 120 g, EtOAc in isohexane, 0-100%, gradient elution) to afford N-(4-((4-nitronaphthalen-1-yl)oxy)pyridin-2-yl)morpholine-4-carboxamide as a yellow solid (2.70 g, 63%); $R^t$ 1.91 min (Method 2); m/z 395 (M+H)$^+$ (ES$^+$).

A solution of N-(4-((4-nitronaphthalen-1-yl)oxy)pyridin-2-yl)morpholine-4-carboxamide (900 mg, 2.3 mmol) in a mixture of MeOH (140 mL), DCM (140 mL) and AcOH (4 drops) was subjected to hydrogenation by passage through a Thales H-cube (1.0 mL min$^{-1}$, 25° C., 55 mm, 10% Pt—C Cat-Cart, full hydrogen mode). The reaction mixture was evaporated in vacuo and the residue was partitioned between DCM (50 mL) and saturated aq. NaHCO$_3$ (20 mL). The organic phase was separated and was washed with brine (20 mL), and then dried and evaporated in vacuo to afford the title compound, Intermediate D5, as a brown solid (0.78 g, 90%); R$^r$ 3.65 min (Method 1 basic); m/z 365 (M+H)$^+$ (ES$^+$).

Intermediate D6: N-(4-(4-Aminonaphthalen-1-yloxy)pyridin-2-yl)-4-methylpiperazine-1-carboxamide

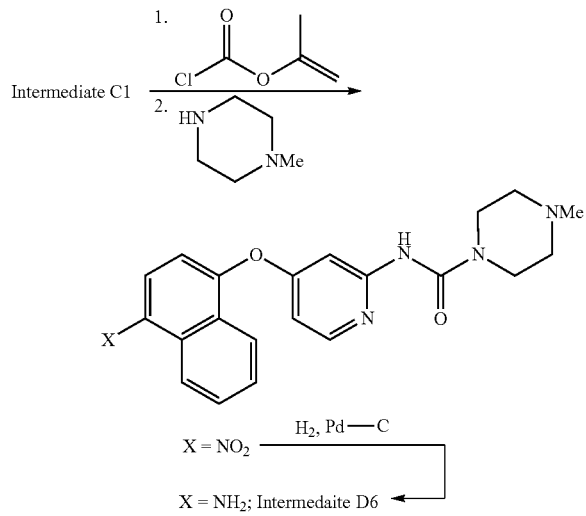

To a suspension of Intermediate C1 (250 mg, 0.89 mmol) and NMM (150 μL, 1.3 mmol) in THF (8.0 mL) at −78° C. under N$_2$ was added dropwise, prop-1-en-2-yl carbonochloridate (150 μL, 1.30 mmol) in THF (3.0 mL) and the reaction mixture then maintained at RT for 16 hr. The reaction was quenched by the addition of MeOH (2.0 mL) and after 1 hr the volatiles were evaporated in vacuo and the residue was partitioned between EtOAc (10 mL) and water (10 mL). The organic layer was separated and washed with brine (10 mL) and then dried and evaporated in vacuo to afford a mixture of prop-1-en-2-yl 4-(4-(nitronaphthalen-1-yloxy)pyridin-2-yl-carbamate and 1-nitro-(4-(2-di(prop-1-ene-2-yloxycarbonyl)aminopyridin-4-yl)oxy)naphthalene as a yellow oil that solidified on standing (390 mg, >100% recovery); R$^r$ 2.67 min (Method 2); m/z 450 (M+H)$^+$ (ES$^+$). This material was used directly in the following step without purification.

To a solution of the mono and bis carbamate product obtained above (195 mg, 0.44 mmol based on Intermediate C1) and 4-methylmorpholine (6.0 μL, 0.05 mmol) in dry THF (1.5 mL) was added 1-methylpiperazine (300 μL, 2.7 mmol) and the resulting yellow reaction mixture warmed to 55° C. for 6 hr and then cooled to RT and evaporated in vacuo. The residue was purified by flash column chromatography (SiO$_2$, MeOH in DCM, 5-10%, gradient elution, then 5% [7M NH$_3$ in MeOH] in DCM, isocratic elution) to afford N-(4-(4-nitronaphthalen-1-yloxy)pyridin-2-yl)-4-methylpiperazine-1-carboxamide as a yellow amorphous solid (130 mg, 71%); R$^r$ 1.56 min (Method 2); m/z 408 (M+H)$^+$ (ES$^+$).

A solution of the urea product, obtained above, (130 mg, 0.32 mmol) in DCM/MeOH (1:1 v/v, 40 mL) was subjected to hydrogenation by passage through a Thales H-cube (1.0 mL min$^{-1}$, 25° C., 70 mm, 10% Pt/C Cat-Cart, full hydrogen mode) and was then evaporated in vacuo. The residue was partitioned between DCM (10 mL) and sat. aq NaHCO$_3$ and the organic layer was separated and washed with brine (10 mL), dried and evaporated in vacuo to afford the title compound, Intermediate D6, as a red solid (87 mg, 69%); R$^r$ 1.05 min (Method 2); m/z 378 (M+H)$^+$ (ES$^+$).

Intermediate D7: 1-(4-(4-Amino-2,3-dimethyl phenoxy)pyridin-2-yl)-3-methyl urea

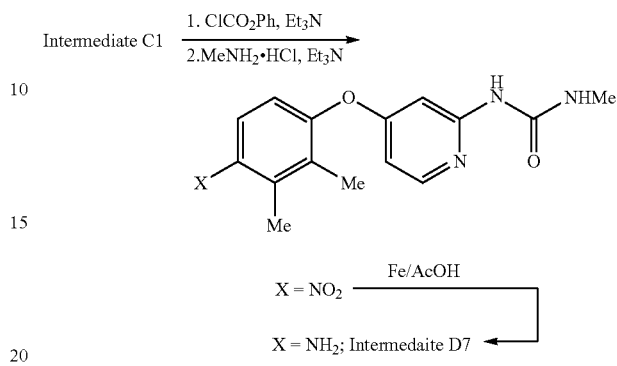

To a suspension of Intermediate C2 (160 mg, 0.62 mmol) in DCM (3.0 mL) containing DIPEA (330 μL, 230 mg, 1.9 mmol) was added phenyl carbonochloridate (160 μL, 190 mg, 1.20 mmol) and the resulting mixture maintained at RT for 1 hr and then treated with a solution of methylamine (2M in THF, 1.20 mL, 2.40 mmol). After 1 hr an additional aliquot of methylamine solution (800 μL, 1.60 mmol) was added and after a further 16 hr the mixture was partitioned between DCM (40 mL) and water (20 mL). The organic layer was separated and was washed with sat. aq NaHCO$_3$ (20 mL) and water (20 mL) and then dried and evaporated in vacuo to afford 1-(4-(2,3-dimethyl-4-nitrophenoxy)pyridin-2-yl)-3-methylurea as a pale orange solid (200 mg, 98%); R$^r$ 1.73 min (Method 2); m/z 317 (M+H)$^+$ (ES$^+$).

A suspension of the nitroarene obtained above (195 mg, 0.616 mmol) and iron powder (172 mg, 3.08 mmol) in AcOH (3.0 mL) was heated to 50° C. for 2 hr and was then cooled to RT and poured on to solid NaHCO$_3$. The resulting mixture was extracted with EtOAc (2×30 mL) and the combined organic extracts were washed with saturated aq. NaHCO$_3$ (15 mL), water (15 mL) and brine (15 mL) and then dried and evaporated in vacuo to provide the title compound, Intermediate D7, (152 mg, 85%); R$^r$ 1.03 min (Method 2); m/z 287 (M+H)$^+$ (ES$^+$).

Intermediate D8: 1-(4-((4-Amino-2,3-dimethylphenoxy)methyl)pyridin-2-yl)-3-methylurea

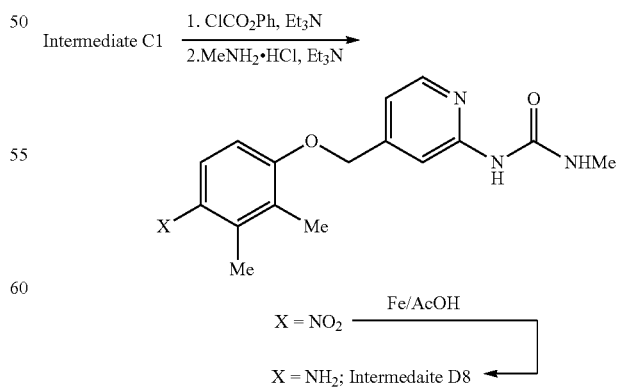

To a suspension of Intermediate C3 (650 mg, 2.40 mmol) in DCM (6.5 mL) containing triethylamine (990 μL, 720 mg, 7.1 mmol) at 0° C. was added phenyl carbonochloridate (630 µL, 780 mg, 5.00 mmol) and the resulting mixture maintained at RT for 1.5 hr. The reaction mixture was re-cooled to 0° C. and was treated with a solution of methylamine (2M in THF, 3.6 mL, 7.2 mmol) and then warmed to RT and treated with further aliquots of the methylamine solution after 2.5 hr (7.2 mL, 14.4 mmol) and 3.5 hr (3.6 mL, 7.2 mmol). After a further 16 hr the reaction was quenched by addition of methanolic NH$_3$ (1% w/v, 10 mL) and the resulting mixture kept at RT for 15 min and then evaporated in vacuo. The residue was partitioned between DCM (200 mL) and water (50 mL). The aq layer was separated and extracted with DCM (2×100 mL) and the combined organic extracts were washed with brine (50 mL) and then dried and evaporated in vacuo. The residue was purified by flash column chromatography (SiO$_2$, 40 g, EtOAc in isohexane, 0-100%, gradient elution) to afford 1-(4-((2,3-dimethyl-4-nitrophenoxy)methyl)pyridin-2-yl)-3-methylurea as a yellow solid (230 mg, 27%); R$^t$ 1.88 min (Method 2); m/z 331 (M+H)$^+$ (ES$^+$).

A suspension of the nitroarene obtained above (230 mg, 0.700 mmol) and iron powder (233 mg, 4.18 mmol) in AcOH (5.0 mL) was heated to 60° C. for 2 hr and then cooled to RT for 16 hr. The resulting mixture was filtered to remove the solids and the filtrate was evaporated in vacuo. The residue was co-evaporated with toluene and was then partitioned between EtOAc (50 mL) and saturated aq. NaHCO$_3$ (50 mL). The aq phase was separated and extracted with EtOAc (30 mL) and the combined organic extracts were washed sequentially with saturated aq. NaHCO$_3$ (50 mL), water (50 mL) and brine (50 mL) and then dried and evaporated in vacuo to provide the title compound, Intermediate D8, as a yellow solid (170 mg, 85% purity, 69%); R$^t$ 4.00 min (Method 1 basic, 85% pure); m/z 301 (M+H)$^+$ (ES$^+$). This material was used in subsequent reactions without further purification.

Intermediate E2:
4-(4-Aminonaphthalen-1-ylthio)pyridin-2-amine

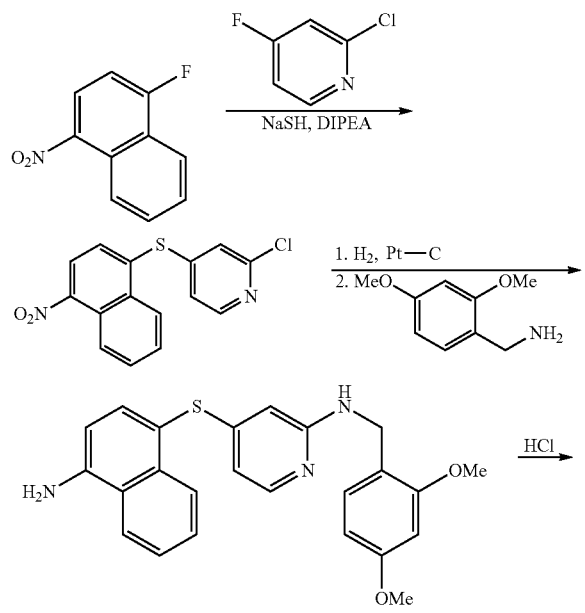

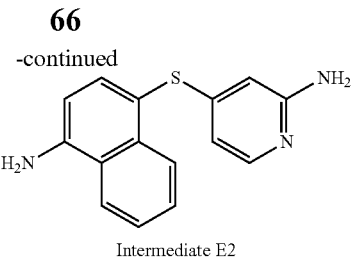

Intermediate E2

A suspension of sodium hydrogensulfide (1.53 g, 18.6 mmol) in NMP (8.0 mL) was purged with N$_2$, and was added dropwise to a similarly purged solution of 2-chloro-4-fluoropyridine (1.74 g, 13.3 mmol) in NMP (6.0 mL) over 1 hr. The reaction mixture was kept at RT for 1 hr and then treated dropwise with a solution of 1-fluoro-4-nitronaphthalene (3.80 g, 19.9 mmol) and DIPEA (4.6 mL, 27 mmol) in NMP (10 mL) over 5 min. After a further 1 hr at RT MeOH (5.0 mL) was added and the reaction mixture kept at RT for 48 hr. The resulting mixture was diluted with EtOAc (250 mL) and was washed sequentially with 2M aq. NaOH (2×150 mL), saturated aq. NaHCO$_3$ (150 mL), water (150 mL) and brine (2×150 mL) The organic layer was dried and evaporated in vacuo and the residue was purified by flash column chromatography (SiO$_2$, 120 g, EtOAc in isohexane, 10-30%, gradient elution) to afford 2-chloro-4-(4-nitronaphthalen-1-ylthio)pyridine as a yellow oil (1.95 g, 5.66 mmol, 43%); R$^t$ 5.02 min (Method 1 basic); m/z 317 (M+H)$^+$ (ES$^+$).

A solution of 2-chloro-4-(4-nitronaphthalen-1-ylthio)pyridine (1.68 g, 5.30 mmol) in a mixture of MeOH (30 mL), EtOAc (100 mL) and AcOH (10 mL) was subjected to hydrogenation by two passages through a Thales H-cube (1.0 mL min$^{-1}$, 50° C., 70 mm, 10% Pt—C Cat-Cart, full hydrogen mode) and was then evaporated in vacuo to afford 4-(2-chloropyridin-4-ylthio) naphthalen-1-amine as a brown oil (1.40 g, 90% purity (LCMS), 83%); R$^t$ 4.50 min (Method 1 basic); m/z 287 (M+H)$^+$ (ES$^+$). The material so obtained was used in the next step without further purification.

A mixture of 4-(2-chloropyridin-4-ylthio)naphthalen-1-amine (1.40 g, 90% purity, 4.40 mmol) and (2,4-dimethoxyphenyl)methanamine (3.7 mL, 24 mmol) was heated together at 120° C. for 24 hr. The reaction mixture was loaded directly onto silica and purified by flash column chromatography (SiO$_2$, 80 g, EtOAc in isohexane, 30-70%, gradient elution) to afford 4-(4-aminonaphthalen-1-ylthio)-N-(2,4-dimethoxybenzyl)pyridin-2-amine as a dark red oil (710 mg, 37%); R$^t$ 1.74 min (Method 2); m/z 418 (M+H)$^+$ (ES$^+$).

To a solution of 4-(4-aminonaphthalen-1-ylthio)-N-(2,4-dimethoxybenzyl)pyridin-2-amine (710 mg, 1.70 mmol) in MeOH (20 mL) at 50° C. was added 6 M aq. HCl (11.5 mL, 69.0 mmol) and the reaction mixture was heated to 70° C. for 3 hr. The mixture was cooled to RT and evaporated in vacuo and the residue was partitioned between saturated aq. NaHCO$_3$ (150 mL) and EtOAc (150 mL). The aq layer was separated and extracted with EtOAc (150 mL) and the combined organic extracts were washed sequentially with saturated aq. NaHCO$_3$ (150 mL) and brine (100 mL), and then dried and evaporated in vacuo. The residue was purified by flash column chromatography (SiO$_2$, 40 g, MeOH in DCM, 0-3%, gradient elution) to afford Intermediate E2 as a yellow oil (200 mg, 41%); R$^t$ 1.52 min (Method 2); m/z 268 (M+H)$^+$ (ES$^+$).

Intermediate F1: (4-(tert-Butoxycarbonyl)aminon-aphthalen-1-yl)(2-(tert-butoxy carbonyl)aminopyridin-4-yl)methanol

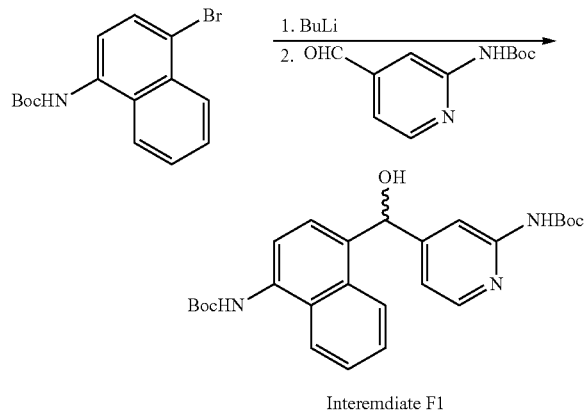

Interemdiate F1

To a stirred solution of tert-butyl (4-bromonaphthalen-1-yl)carbamate (WO 2006/010082) (2.09 g, 6.48 mmol) in dry THF (50 mL) under N₂ at −78° C. was added n-butyllithium (2.5 M in hexanes, 5.5 mL, 13.8 mmol) over 15 mins. The resulting mixture was maintained at −78° C. for 1.5 hr and then treated with a solution of tert-butyl (4-formylpyridin-2-yl)carbamate (WO 2004/000831) (960 mg, 4.30 mmol) in dry THF (10 mL) in one portion. The reaction mixture was stirred at −78° C. for a further 1 hr and then warmed to RT for 18 hr. The mixture was cooled to 0° C. and the reaction was quenched by the addition of MeOH (5.0 mL), then warmed to RT and partitioned between EtOAc and water. The aq layer was separated and was extracted twice with EtOAc and the combined organic extracts were washed with brine and then dried and evaporated in vacuo. The residue was purified by flash column chromatography (SiO₂, 80 g, EtOAc in isohexane, 0-60%, gradient elution) to afford the title compound, Intermediate F1, as a pale yellow solid (1.13 g, 88% purity (LCMS), 49%); Rt 2.22 min (Method 2); m/z 466 (M+H)⁺ (ES⁺). The material so obtained was used in the next step without further purification.

Intermediate G1: (4-Aminonaphthalen-1-yl)(2-aminopyridin-4-yl)methanone

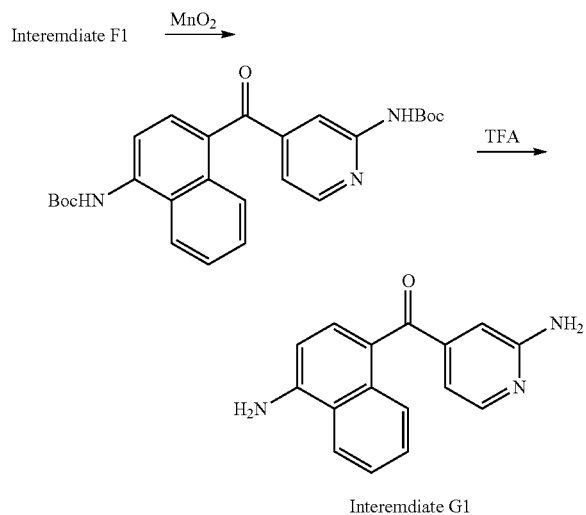

Interemdiate G1

To a solution of Intermediate F1 (534 mg, 88% purity, 1.15 mmol) in dry DCM (25 mL) at 0° C. under N₂ was added manganese dioxide (1.50 g, 17 mmol). The reaction mixture was warmed to RT for 19 hr and was then diluted with ether and filtered through a pad of celite. The celite pad was washed through with ether and the combined filtrate and washings were evaporated in vacuo. The residue was purified, by flash column chromatography (SiO₂, 80 g, EtOAc in isohexane, 0-35%, gradient elution) to afford (4-(tert-butoxycarbonyl)amino naphthalen-1-yl)(2-(tert-butoxycarbonyl)aminopyridin-4-yl)methanone as a yellow powder (0.384 g, 72%); Rt 2.86 min (Method 2); m/z 464 (M+H)⁺ (ES⁺).

To a solution of (4-(tert-butoxycarbonyl)aminonaphthalen-1-yl)(2-(tert-butoxycarbonyl)amino pyridin-4-yl)methanone (378 mg, 0.815 mmol) in DCM (20 mL) under N₂ at 0° C. was added TFA (4.0 mL, 50 mmol). After 30 min at 0° C. the reaction mixture was warmed to RT for 4.5 hr and was then evaporated in vacuo. The residue was subjected to purification by SCX capture and release to afford the title compound, Intermediate G1, as a yellow solid (200 mg, 93%); Rt 1.01 min (Method 2); m/z 264 (M+H)⁺ (ES⁺).

Intermediate H1: 4-((4-aminonaphthalen-1-yl)methyl)pyridin-2-amine

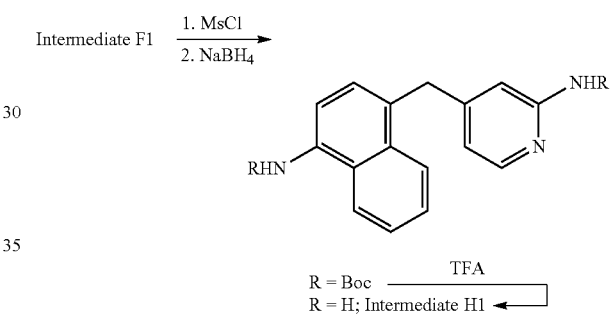

To a solution of Intermediate F1 (450 mg, 0.967 mmol) and DIPEA (670 µL, 3.90 mmol) in dry DCM (25 mL) under N₂ at 0° C. was added methanesulfonyl chloride (220 µL, 2.90 mmol) and after 30 min at 0° C. the mixture warmed to RT for 4 hr. The reaction was quenched by addition of saturated aq. NaHCO₃ and the mixture partitioned between water and DCM. The aq. layer was extracted with DCM and the combined organic extracts were washed with brine and then dried and evaporated in vacuo. The residue was taken up into MeOH (25 mL) and was cooled to 0° C. under N₂ and treated with sodium borohydride (55 mg, 1.5 mmol) and after 20 min at 0° C. was warmed to RT for 1.5 hr. A second portion of sodium borohydride (55 mg, 1.5 mmol) was added and the reaction mixture was kept at RT for 1 hr and was then partitioned between DCM and water. The aq. layer was extracted with DCM and the combined organic extracts were washed with brine and then dried and evaporated in vacuo. The residue was purified by flash column chromatography (SiO₂, 80 g, EtOAc in isohexane, 0-40%, gradient elution) to afford (4-(tert-butoxycarbonyl)aminonaphthalen-1-yl)(2-(tert-butoxycarbonyl)aminopyridin-4-yl)methane as a white solid (234 mg, 54%); Rᵗ 2.54 min (Method 2); m/z 450 (M+H)⁺ (ES⁺).

To a solution of (4-(tert-butoxycarbonyl)aminonaphthalen-1-yl)(2-(tert-butoxycarbonyl)amino pyridin-4-yl)methane (270 mg, 0.60 mmol) in dry DCM (6.0 mL) under N₂ at 0° C. was added TFA (2.0 mL, 25 mmol). The reaction was maintained at 0° C. for a further 20 min and was then warmed to RT for 4 hr. The mixture was evaporated in vacuo and the residue was subjected to SCX capture and release to afford the title compound, Intermediate H1, (150 mg, 100%); R$^t$ 0.79 min (Method 2); m/z 250 (M+H)$^+$ (ES$^+$).

Example 1

N-(4-(4-(3-(1-(4-Aminophenyl)-3-tert-butyl-1H-pyrazol-5-yl)ureido) naphthalen-1-yloxy)pyridin-2-yl)-2-methoxyacetamide

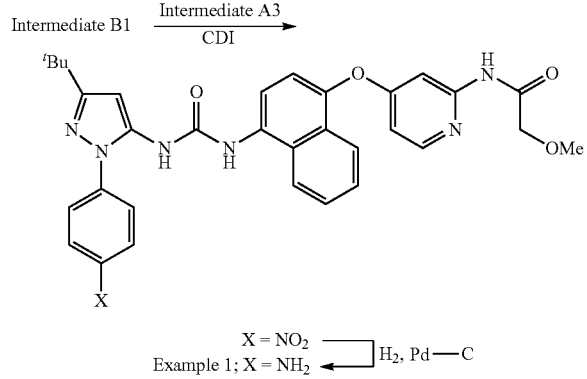

To a suspension of CDI (301 mg, 1.86 mmol) in DCM (4.0 mL) was added Intermediate A3 (483 mg, 1.86 mmol) and the reaction mixture maintained at RT for 16 hr. A solution of Intermediate B1 (260 mg, 0.80 mmol) in DCM (2.6 mL) was added and after a further 24 hr at RT the reaction mixture was partitioned between DCM (20 mL) and water (20 mL). The organic layer was separated and was washed with brine (20 mL) and then dried and evaporated in vacuo. The residue was purified by flash column chromatography (SiO$_2$, EtOAc in isohexane, 30-100%, gradient elution) to afford N-(4-(4-(3-(3-tert-butyl-1-(4-nitrophenyl)-1H-pyrazol-5-yl)ureido) naphthalen-1-yloxy)pyridin-2-yl)-2-methoxyacetamide as a pale brown solid (290 mg, 50%); R$^t$ 5.12 min (Method 1 basic); m/z 610 (M+H)$^+$ (ES$^+$).

A solution of N-(4-(4-(3-(3-tert-butyl-1-(4-nitrophenyl)-1H-pyrazol-5-yl)ureido)naphthalen-1-yloxy)pyridin-2-yl)-2-methoxyacetamide (270 mg, 0.443 mmol) in a mixture of MeOH (20 mL) and AcOH (1.0 mL) was subjected to hydrogenation by passage through a Thales H-cube (1.0 mL min$^{-1}$, 40° C., 55 mm, 10% Pt—C Cat-Cart, full hydrogen mode). The reaction mixture was evaporated in vacuo and the residue was partitioned between EtOAc (15 mL) and saturated aq. NaHCO$_3$ (15 mL). The organic layer was separated and was washed with brine (15 mL) and then dried and evaporated in vacuo. The residue was purified by flash column chromatography (SiO$_2$, EtOAc in isohexane, 20-100%, gradient elution) to afford the title compound, Example 1, as a pale brown solid (115 mg, 43%); R$^t$ 4.87 min (Method 1 basic); m/z 580 (M+H)$^+$ (ES$^+$); $^1$H NMR (400 MHz, DMSO-d$_6$) δ: 1.25 (9H, s), 3.30 (3H, s), 3.98 (2H, s), 5.41 (2H, s), 6.34 (1H, s), 6.68-6.71 (3H, overlapping m), 7.14 (2H, d), 7.33 (1H, d), 7.57 (1H, m), 7.63-7.67 (2H, overlapping m), 7.83 (1H, d), 7.98 (1H, dd), 8.09 (1H, d), 8.18 (1H, d), 8.65 (1H, s), 9.18 (1H, s), 10.04 (1H, s).

Example 2

N-(4-(4-(3-(3-tert-Butyl-1-(4-(methylsulfonamido)phenyl)-1H-pyrazol-5-yl)ureido)naphthalen-1-yloxy)pyridin-2-yl)-2-methoxyacetamide

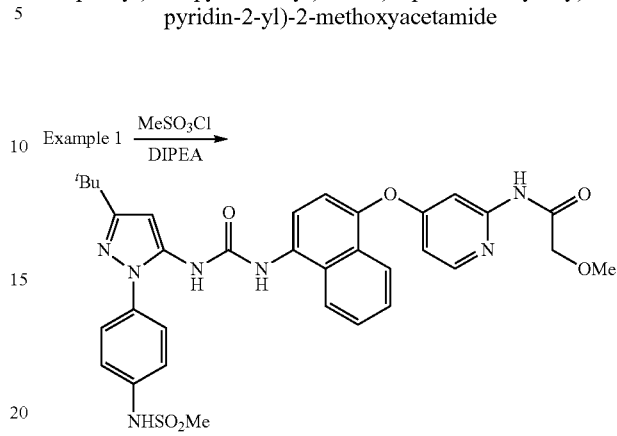

To a solution of Example 1 (42 mg, 0.072 mmol) in DCM (2.0 mL) and DIPEA (26 µL, 0.14 mmol) at 0° C. was added methanesulfonyl chloride (8.0 µL, 0.1 mmol) in DCM (1.0 mL) and the reaction mixture was warmed to RT for 2 hr. Additional aliquots of DIPEA (26 µL, 0.14 mmol) and methanesulfonyl chloride (4.0 µL, 0.05 mmol) were added and after a further 2 hr the reaction mixture was washed with saturated aq NaHCO$_3$ (2.0 mL). The organic layer was separated and evaporated in vacuo and the residue was purified by flash column chromatography (SiO$_2$, EtOAc in isohexane, 20-100%, gradient elution) to afford the title compound, Example 2, as a pale purple solid (24 mg, 48%); Rt 4.00 min (Method 1 basic); m/z 658 (M+H)$^+$ (ES$^+$); $^1$H NMR (400 MHz, DMSO-d$_6$) δ: 1.27 (9H, s), 3.06 (3H, s), 3.29 (3H, s), 3.98 (2H, s), 6.41 (1H, s), 6.70 (1H, dd), 7.34 (1H, d), 7.37 (2H, m), 7.54 (2H, m), 7.58 (1H, d), 7.64-7.67 (2H, overlapping m), 7.83 (1H, d), 7.95 (1H, d), 8.09 (1H, d), 8.18 (1H, d), 8.81 (1H, s), 9.12 (1H, s), 10.01 (1H, s), 10.05 (1H, s)

Example 3

N-(4-((4-(3-(3-(tert-Butyl)-1-(4-methoxyphenyl)-1H-pyrazol-5-yl)ureido) naphthalen-1-yl)oxy)pyridin-2-yl)-2-methoxyacetamide

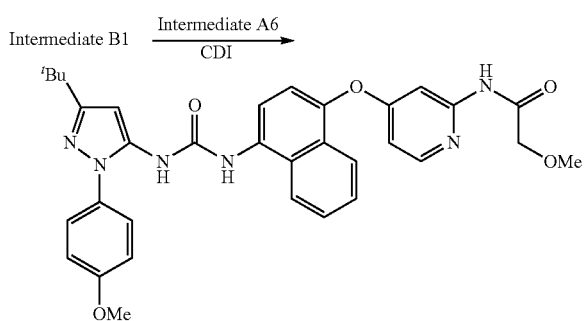

To a suspension of CDI (130 mg, 0.80 mmol) in DCM (1.5 mL) was added Intermediate A6 (197 mg, 0.804 mmol) and the reaction mixture maintained at RT for 2 hr. An aliquot of this solution (500 µL, 0.30 mmol) was added to a solution of Intermediate B1 (65 mg, 0.20 mmol) in DCM (1.5 mL) under N₂ at 0° C. and the reaction mixture was warmed to RT. Further portions of CDI adduct were added after 4 hr (500 µL, 0.30 mmol) and after 21 hr (200 µL, 0.10 mmol) and after a total of 23 hr the reaction mixture was partitioned between DCM (15 mL) and saturated aq. NaHCO₃ (15 mL). The aq layer was separated and extracted with DCM (15 mL) and the combined organic extracts were washed with brine (15 mL) and then dried and evaporated in vacuo. The residue was purified twice by flash column chromatography (SiO₂, 12 g, [5% MeOH in EtOAc] in isohexane, 0-55%, gradient elution then SiO₂, 12 g, MeOH in DCM, 0-8%, gradient elution) to afford the title compound, Example 3, as a pink powder (34 mg, 28%); R$^t$ 2.46 min (Method 2); m/z 595 (M+H)$^+$ (ES$^+$); $^1$H NMR (400 MHz, DMSO-d₆) δ: 1.28 (9H, s), 3.31 (3H, s), 3.84 (3H, s), 3.99 (2H, s), 6.39 (1H, s), 6.70 (1H, dd), 7.09-7.15 (2H, m), 7.34 (1H, d), 7.45-750. (2H, m), 7.57 (1H, ddd), 7.62-7.67 (2H, overlapping m), 7.84 (1H, dd), 7.97 (1H, d), 7.08 (1H, br d), 7.18 (1H, dd), 8.74 (1H, br s), 9.11 (1H, br s), 10.02 (1H, br s).

Example 4

N-(4-(4-(3-(3-tert-Butyl-1-(4-methoxyphenyl)-1H-pyrazol-5-yl)ureido) naphthalen-1-yloxy)pyridin-2-yl)-2-hydroxyacetamide

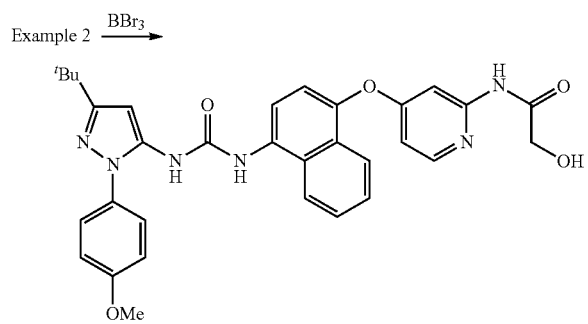

Example 4

To a solution of Example 2 (50 mg, 0.084 mmol) in dry DCM (2.0 mL) at 0° C. was added tribromoborane (1.0 M in DCM, 250 µL, 0.25 mmol) and the reaction mixture maintained at 0° C. for 5 min and then warmed to RT for 3 hr. The resulting mixture was partitioned between DCM (20 mL) and saturated aq. NaHCO₃ (10 mL) and the organic layer was separated, washed with brine (5.0 mL) and then dried and evaporated in vacuo. The residue was purified by flash column chromatography (SiO₂, 12 g, MeOH in DCM, 2-5%, gradient elution) to afford the title compound, Example 4, as a pale brown solid (12 mg, 24%); Rt 4.67 min (Method 1 basic); m/z 581 (M+H)$^+$ (ES$^+$); $^1$H NMR (400 MHz, DMSO-d₆) δ: 1.28 (9H, s), 3.84 (3H, s), 3.96 (2H, d), 5.64 (1H, t), 6.39 (1H, s), 6.72 (1H, dd), 7.12 (2H, m), 7.35 (1H, d), 7.48 (2H, m), 7.57 (1H, t), 7.63-7.66 (2H, overlapping m), 7.84 (1H, d), 7.97 (1H, d), 8.09 (1H, d), 8.19 (1H, d), 8.76 (1H, s), 9.14 (1H, s), 9.74 (1H, s).

Example 5

N-(4-((4-(3-(3-(tert-Butyl)-1-(4-hydroxyphenyl)-1H-pyrazol-5-yl)ureido) naphthalen-1-yl)oxy)pyridin-2-yl)-2-methoxyacetamide

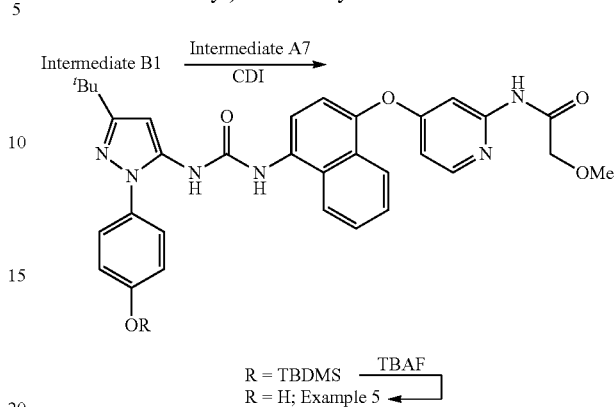

To a suspension of CDI (23 mg, 0.15 mmol) in DCM (1.0 mL) was added Intermediate A7 (50 mg, 0.15 mmol) and the reaction mixture maintained at RT for 16 hr and then treated with solid Intermediate B1 (40 mg, 0.12 mmol). After a further 2 hr the crude reaction mixture was subjected, without prior work-up, to purification by flash column chromatography (SiO₂, 40 g, EtOAc in isohexane, 20-100%, gradient elution) to provide N-(4-(4-(3-(3-tert-butyl-1-(4-(tert-butyldimethylsilyloxy)phenyl)-1H-pyrazol-5-yl)ureido)naphthalen-1-yloxy)pyridin-2-yl)-2-methoxyacetamide as a brown oil (45 mg, 44%); R$^t$ 3.21 min (Method 1 basic); m/z 695 (M+H)$^+$ (ES$^+$).

To a solution of silylether product obtained above (36 mg, 0.052 mmol) in THF (1.0 mL) at RT was added TBAF (1M solution in THF, 57 µL, 0.057 mmol). After 10 min the reaction mixture was partitioned between EtOAc (10.0 mL) and saturated aq. NaHCO₃ (2.0 mL). The organic layer was separated and washed with brine (2.0 mL) and then dried and evaporated in vacuo. The residue was purified by flash column chromatography (SiO₂, 12 g, MeOH in DCM, 0-10%, gradient elution) to afford the title compound, Example 5 as an off white solid (24 mg, 79%); R$^t$ 2.26 min (Method 2); m/z 581 (M+H)$^+$ (ES$^+$); $^1$H NMR (400 MHz, DMSO-d₆) δ: 1.27 (9H, s), 3.30 (3H, s), 3.99 (2H, s), 6.38 (1H, s), 6.70 (1H, dd), 6.91-6.95 (2H, overlapping m) 7.32-7.37 (3H, overlapping m), 7.57 (1H, ddd), 7.63-7.67 (2H, m) 7.83 (1H, dd), 7.98 (1H, d), 8.08 (1H, br d), 8.19 (1H, d), 8.73 (1H, br d), 9.15 (1H, br d), 9.82 (1H, br d), 10.07 (1H, br d).

Example 6

1-(3-(tert-Butyl)-1-(4-methoxyphenyl)-1H-pyrazol-5-yl)-3-(4-(2-(3-cyclo propylureido)pyridin-4-yloxy) naphthalen-1-yl)urea Example 6

To a solution of CDI (150 mg, 0.56 mmol) in dry DCM (1.5 mL) was added Intermediate A6 (136 mg, 0.56 mmol) in three portions over 45 min and the resulting brown solution maintained at RT for 16 hr. An aliquot of this solution (400 µL, 0.15 mmol) was added to a suspension of Intermediate D3 (45 mg, 0.14 mmol) in DCM (1.0 mL) and the reaction mixture was kept at RT for 1 hr. The reaction was quenched by the addition of MeOH (5.0 mL) and after a further 0.5 hr the mixture was evaporated in vacuo. The residue was taken up into EtOAc (20 mL) and was washed with water (20 mL) and brine (20 mL) and then dried and evaporated in vacuo. The residue was purified by flash column chromatography (SiO$_2$, 4 g, MeOH in DCM, 0-100%, gradient elution, and then SiO$_2$, 4 g, EtOAc in DCM, 0-100%, gradient elution) to provide an impure sample of the product that was triturated with DCM/isohexane (1:1 v/v, 2 mL). The solid was collected by filtration and was washed with isohexane (1 mL) and then re-suspended in EtOAc (1.0 mL). The mixture was sonicated briefly and then kept at RT for 16 hr. The solid was collected by filtration and was washed with isohexane to afford the title compound, Example 6, as a white solid (10 mg, 90% purity by LCMS), 11%); R$^t$ 2.44 min (Method 2); m/z 606 (M+H)$^+$ (ES$^+$). 1H NMR (400 MHz, DMSO-d$_6$) δ: 0.37 (2H, m), 0.60 (2H, m), 1.27 (9H, s), 3.72 (1H, s), 3.83 (3H, s), 6.39 (1H, s), 6.56 (1H, dd), 6.96 (1H, s), 7.11 (2H, d), 7.30 (1H, s), 7.47 (2H, d), 7.56 (1H, m), 7.65 (1H, m), 7.81 (1H, d), 7.90 (1H, br s), 7.96 (1H, d), 8.05 (1H, d), 8.07 (1H, d), 8.72 (1H, s), 8.95 (1H, s), 9.10 (1H, s)

Example 7

3-(4-(4-(3-(3-tert-Butyl-1-(4-methoxyphenyl)-1H-pyrazol-5-yl)ureido) naphthalen-1-yloxy)pyridin-2-yl)-1,1-dimethylurea

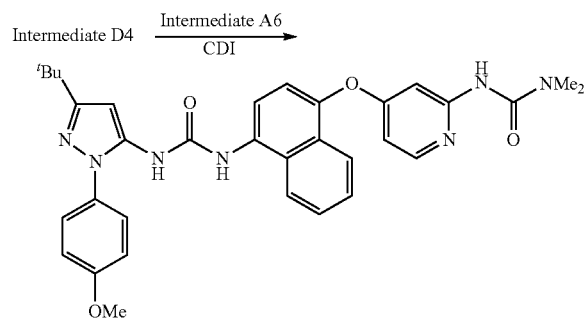

Example 7

To a solution of CDI (113 mg, 0.696 mmol) in DCM (2.0 mL) was added Intermediate A6 (171 mg, 0.698 mmol) and the reaction mixture maintained at RT for 3 hr. A solution of Intermediate D4 (150 mg, 0.465 mmol) in DCM (1.0 mL) was added and the resulting mixture was kept at RT for 16 hr and then partitioned between DCM (20 mL) and water (20 mL). The organic layer was separated and was washed with brine (20 mL) and then dried and evaporated in vacuo. The residue was purified by flash column chromatography (SiO$_2$, 4.0 g, EtOAc in isohexane, 30-100%, gradient elution) and the impure product so obtained was triturated with ether (5.0 mL) to afford the title compound, Example 7, as a beige solid (155 mg, 54%); R$^t$ 4.75 min (Method 1 basic); m/z 594 (M+H)$^+$ (ES$^+$); $^1$H NMR (400 MHz, DMSO-d$_6$) δ: 1.28 (9H, s), 2.85 (6H, s), 3.83 (3H, s), 6.40 (1H, s), 6.60 (1H, dd), 7.10-7.14 (2H, overlapping m), 7.31 (1H, d), 7.38 (1H, d), 7.46-7.50 (2H, overlapping m), 7.57 (1H, ddd), 7.64 (1H, ddd), 7.84 (1H, dd), 7.96 (1H, d), 8.07 (1H, br d), 8.10 (1H, d), 8.75 (1H, br s), 8.88 (1H, br s), 9.11 (1H, br s).

Example 8

N-(4-(4-(3-(3-tert-Butyl-1-(4-methoxyphenyl)-1H-pyrazol-5-yl)ureido) naphthalen-1-yloxy)pyridin-2-yl)pyrrolidine-1-carboxamide

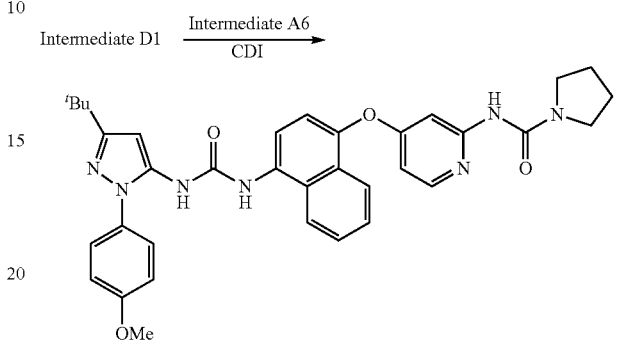

Example 8

To a solution of CDI (93 mg, 0.57 mmol) in DCM (1.0 mL) was added Intermediate A6 (141 mg, 0.57 mmol) and the reaction mixture maintained at RT for 3 hr and then diluted with DCM (2.0 mL) and treat with Intermediate D1 (100 mg, 0.29 mmol). The resulting mixture was kept at RT for a further 16 hr and was partitioned between DCM (10 mL) and water (10 mL). The organic layer was separated and washed with brine (10 mL), and was then dried and evaporated in vacuo. The residue was purified by flash column chromatography (SiO$_2$, EtOAc in isohexane, 20-100%, gradient elution then 5% MeOH in EtOAc, isocratic elution). The crude material so obtained was triturated with ether (3.0 mL) to afford the title compound, Example 8 as a pale pink solid (91 mg, 51%); R$^t$ 5.20 min (Method 1 basic); m/z 620 (M+H)$^+$ (ES$^+$); $^1$H NMR (400 MHz, DMSO-d$_6$) δ: 1.28 (9H, s), 1.78 (4H, br s), 3.33 (4H, br s, partially obscured by HOD peak) 3.83 (3H, s), 6.39 (1H, s), 6.66 (1H, br s), 7.10-7.14 (2H, overlapping m), 7.32 (1H, d), 7.40 (1H, br s), 7.46-7.50 (2H, br s), 7.58 (1H, ddd), 7.65 (1H, ddd), 7.84 (1H, dd), 7.97 (1H, d), 8.09 (1H, d), 8.12 (1H, d), 8.77 (2H, br s), 9.14 (1H, br s).

Example 9

N-(4-((4-(3-(3-tert-Butyl-1-(4-methoxyphenyl)-1H-pyrazol-5-yl)ureido) naphthalen-1-yl)oxy)pyridin-2-yl)morpholine-4-carboxamide

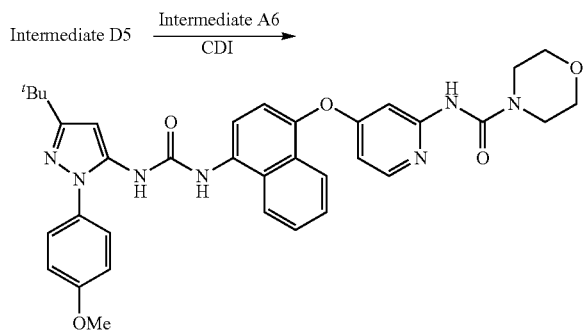

Example 9

To a suspension of CDI (100 mg, 0.61 mmol) in DCM (1.0 mL) was added Intermediate A6 (91 mg, 0.37 mmol) and the reaction mixture maintained at RT for 16 hr. To a suspension of Intermediate D5 (54 mg, 0.15 mmol) in DCM (1.0 mL) was added an aliquot of the preformed aminopyrazole/CDI adduct (0.45 mL, 0.17 mmol) and the resulting mixture kept at RT for 1 hr and then quenched with MeOH (5.0 mL). After a further 30 min the volatiles were evaporated in vacuo and the residue was partitioned between EtOAc and water (20 mL). The organic layer was separated and was washed with brine (20 mL) and then dried and evaporated in vacuo. The residue was purified by flash column chromatography (SiO$_2$, 12 g, [5% MeOH in DCM] in DCM, 0-100%, gradient elution) to afford the title compound, Example 9 as an off white solid (35 mg, 35%); R$^t$ 2.17 min (Method 2); m/z 636 (M+H)$^+$ (ES$^+$); $^1$H NMR (400 MHz, DMSO-d$_6$) δ: 1.28 (9H, s), 3.34-3.39 (4H, overlapping m), 3.50-3.55 (4H, overlapping m), 3.84 (3H, s), 6.39 (1H, s), 6.61 (1H, dd), 7.09-7.14 (2H, m), 7.31 (1H, d), 7.37 (1H, d), 7.45-7.51 (2H, m), 7.57 (1H, ddd), 7.64 (1H, ddd), 7.84 (1H, dd), 7.95 (1H, d), 8.07 (1H, br d), 7.12 (1H, d), 8.73 (1H, br s), 9.10 (1H, br s), 9.23 (1H, br s).

Example 10

N-(4-(4-(3-(3-tert-Butyl-1-(4-methoxyphenyl)-1H-pyrazol-5-yl)ureido) naphthalen-1-yloxy)pyridin-2-yl)-4-methyl piperazine-1-carboxamide

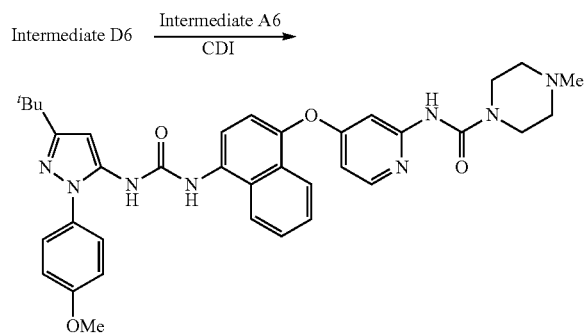

Example 10

To a solution of CDI (150 mg, 0.93 mmol) in DCM (1.5 mL) was added Intermediate A2 (136 mg, 0.56 mmol) and the reaction mixture maintained at RT for 16 hr. An aliquot of the resulting solution (0.35 mL, 0.13 mmol) containing the CDI adduct was added to a solution of Intermediate D6 (54 mg, 0.15 mmol) in DCM (1.0 mL) and the reaction mixture kept at RT. for 1 hr and then quenched by the addition of with MeOH (5.0 mL). After 30 min the volatiles were evaporated in vacuo and the residue was partitioned between EtOAc (20 mL) and water (20 mL). The organic layer was separated and was washed with brine (20 mL), dried and evaporated in vacuo. The residue was purified by flash column chromatography (SiO$_2$, 4.0 g, [5% (7M NH$_3$ in MeOH) in DCM] in DCM, 0-100%, gradient elution). Fractions containing product were evaporated and the residue so obtained was suspended in EtOAc (1.0 mL) and sonicated. The supernatant was decanted and the process was repeated with ether (1.0 mL) and EtOAc (1.0 mL). The resulting solid was isolated by filtration and dried in vacuo to afford Example 10 as a pink solid (8 mg, 10%); R$^t$ 4.75 min (Method 1 basic); m/z 649 (M+H)$^+$ (ES$^+$); $^1$H NMR (400 MHz, DMSO-d$_6$) δ: 1.27 (9H, s), 2.37 (3H, br s), 2.55 (4H, br s, partially obscured by DMSO), 3.46 (4H, br s), 3.83 (3H, s), 6.38 (1H, s), 6.62 (1H, dd), 7.11 (2H, m), 7.30 (1H, d), 7.35 (1H, m), 7.48 (2H, m), 7.56 (1H, ddd), 7.64 (1H, ddd), 7.83 (1H, dd), 7.95 (1H, d), 8.10 (2H, m), 8.79 (1H, br s), 9.15 (1H, br s), 8.29 (1H, br s).

Example 11

N-(4-(4-(3-(3-tert-Butyl-1-(3,4-dimethoxyphenyl)-1H-pyrazol-5-yl)ureido) naphthalen-1-yloxy)pyridin-2-yl)-2-methoxyacetamide

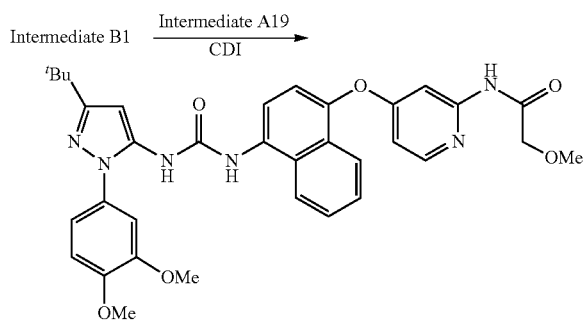

Example 11

To a solution of CDI (75 mg, 0.46 mmol) in DCM (1.0 mL) was added Intermediate A19 (128 mg, 0.465 mmol) and the reaction mixture maintained at RT for 3 hr and then treated with a solution of Intermediate B1 (120 mg, 0.37 mmol) in DCM (0.5 mL). After 16 h at RT the reaction mixture was quenched with MeOH (1.0 mL) and after a further 5 min was evaporated in vacuo. The residue was purified by flash column chromatography (SiO$_2$, 12 g, EtOAc in isohexane, 0-75%, gradient) and the crude product so obtained was recrystallized from EtOAc/isohexane to afford the title compound, Example 11 as a pale purple solid (116 mg, 49%); R$^t$ 4.67 min (Method 1 basic); m/z 625 (M+H)$^+$ (ES$^+$); $^1$H NMR (400 MHz, DMSO-d$_6$) δ: 1.28 (9H, s), 3.30 (3H, s), 3.82 (3H, s), 3.83 (3H, s), 3.98 (2H, s), 6.41 (1H, s), 6.70 (1H, dd), 7.07 (1H, dd), 7.12-7.14 (2H, overlapping m), 7.34 (1H, d), 7.57 (1H, ddd), 7.63-7.66 (2H, m), 7.84 (1H, dd), 7.98 (1H, d), 8.09 (1H, br d), 8.19 (1H, d), 8.75 (1H, br s), 9.15 (1H, br, s). 10.04 (1H, br s).

Example 12

N-(4-((4-(3-(3-(tert-Butyl)-1-(3-chloro-4-hydroxyphenyl)-1H-pyrazol-5-yl)ureido)naphthalen-1-yl)oxy)pyridin-2-yl)morpholine-4-carboxamide

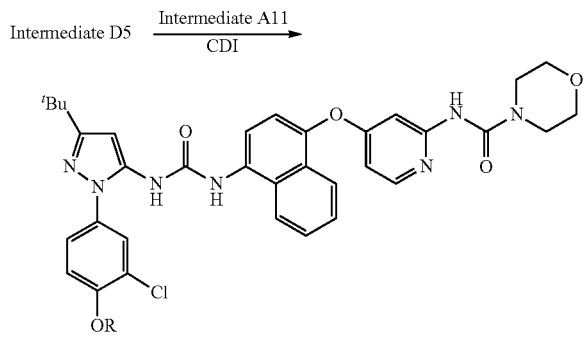

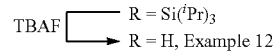

To a solution of CDI (58 mg, 0.36 mmol) in dry DCM (1.0 mL) was added Intermediate A11 (150 mg, 0.36 mmol) in two equal portions over 10 min and the reaction maintained at RT for 5 hr. The mixture was treated with Intermediate D5 (104 mg, 0.284 mmol), diluted with DCM (0.5 mL) and kept at RT for 16 hr. A second batch of the CDI adduct was prepared in an identical manner to the first and an aliquot of this solution (800 μL, 0.30 mmol) was added to the reaction mixture which was then kept at RT for 84 hr. The reaction was quenched by the addition of MeOH (1.0 mL) and after 5 min the volatiles were evaporated in vacuo. The residue was purified by flash column chromatography (SiO$_2$, EtOAc in isohexane, 0-100%, gradient elution) to afford N-(4-(4-(3-(3-tert-butyl-1-(3-chloro-4-(triisopropylsilyloxy)phenyl)-1H-pyrazol-5-yl)ureido)naphthalen-1-yloxy)pyridin-2-yl)morpholine-4-carboxamide as an off white solid (173 mg, 54%); R$^t$ 5.90 min (Method 1 basic); m/z 812 (M+H)$^+$ (ES$^+$).

To a solution of N-(4-(4-(3-(3-tert-butyl-1-(3-chloro-4-(triisopropylsilyloxy)phenyl)-1H-pyrazol-5-yl)ureido)naphthalen-1-yloxy)pyridin-2-yl)morpholine-4-carboxamide (70 mg, 0.078 mmol) in dry THF (2.0 mL) was added TBAF (1.0 M in THF, 116 μL, 0.116 mmol) and the reaction mixture kept at RT for 16 hr. The reaction mixture was diluted with MeOH (1.0 mL) and after 5 min was evaporated in vacuo. The residue was purified by flash column chromatography (SiO$_2$, 4 g, EtOAc in isohexane, 0-100%, gradient elution) to afford the title compound, Example 12, as a pink solid (20 mg, 39%); R$^t$ 3.97 min (Method 1 basic); m/z 655 (M+H)$^+$ (ES$^+$); $^1$H NMR (400 MHz, DMSO-d$_6$) δ: 1.27 (9H, s), 3.36 (4H, m), 3.52 (4H, m), 6.37 (1H, s), 6.61 (1H, dd), 7.12 (1H, d), 7.31 (1H, d), 7.35 (1H, dd), 7.37 (1H, d), 7.54 (1H, d), 7.57 (1H, m), 7.64 (1H, m), 7.84 (1H, d), 7.91 (1H, br s), 8.06 (1H, d), 8.12 (1H, d), 8.74 (1H, s), 9.09 (1H, s), 9.26 (1H, s), 10.62 (1H, br s).

Example 13

N-(4-(4-(3-(3-tert-Butyl-1-(3-chloro-4-(hydroxymethyl)phenyl)-1H-pyrazol-5-yl)ureido)naphthalen-1-yloxy)pyridin-2-yl)-2-methoxyacetamide

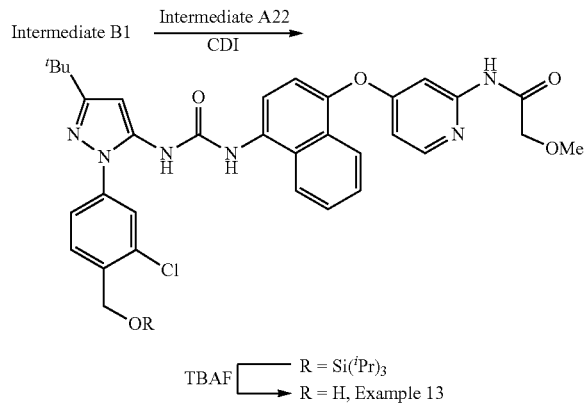

To a solution of CDI (0.112 g, 0.688 mmol) in dry DCM (1.0 mL) was added dropwise a solution of Intermediate A22 (300 mg, 0.688 mmol) in DCM was (1.0 mL) and the reaction mixture maintained at RT for 20 hr. An portion of this solution (1.0 mL, 0.34 mmol) was added to a solution of Intermediate B1 (70 mg, 0.22 mmol) in dry DCM (2.0 mL) under N$_2$ and the reaction mixture was maintained at RT for 18 hr and then quenched by the addition of MeOH (2.0 mL). After a further 30 min at RT the volatiles were evaporated in vacuo and the residue was purified by flash column chromatography (SiO$_2$, 4.0 g, EtOAc in isohexane, 0-100%, gradient elution) to afford N-(4-(4-(3-(3-tert-butyl-1-(3-chloro-4-((triisopropylsilyloxy)methyl)phenyl)-1H-pyrazol-5-yl)ureido)naphthalen-1-yloxy)pyridin-2-yl)-2-methoxyacetamide as a yellow solid (75 mg, 44%); Rt 3.45 min (Method 2); m/z 785 (M+H)$^+$ (ES$^+$).

To a solution the silyl ether obtained above (75 mg, 0.096 mmol) in dry THF (2.0 mL) was added TBAF (1.0 M in THF, 120 μL, 0.12 mmol) and the reaction mixture maintained at RT for 20 hr and then partitioned between DCM (20 mL) and saturated aq. NaHCO$_3$ (5.0 mL). The aq layer was separated and extracted with DCM (20 mL) and the combined organic extracts were washed with brine, dried and evaporated in vacuo. The residue was purified by flash column chromatography (SiO$_2$, 12 g, MeOH in DCM, 0-10%, gradient elution) to afford the title compound, Example 13, as a white solid (47 mg, 77%); Rt 2.28 min (Method 2); m/z 629 (M+H)$^+$ (ES$^+$); $^1$H NMR (400 MHz, DMSO-d$_6$) δ: 1.29 (9H, s), 3.30 (3H, s), 3.99 (2H, s), 4.63 (2H, s), 5.55 (1H, br s), 6.42 (1H, s), 6.70 (1H, dd), 7.34 (1H, d), 7.58 (1H, m), 7.60-7.67 (4H, overlapping m), 7.71 (1H, d), 7.84 (1H, d), 7.90 (1H, d), 8.09 (1H, d), 8.19 (1H, d), 8.85 (1H, s), 9.12 (1H, s), 10.05 (1H, s).

Example 14

N-(4-(4-(3-(3-tert-Butyl-1-(4-(methylthio)phenyl)-1H-pyrazol-5-yl)ureido) naphthalen-1-yloxy)pyridin-2-yl)pyrrolidine-1-carboxamide

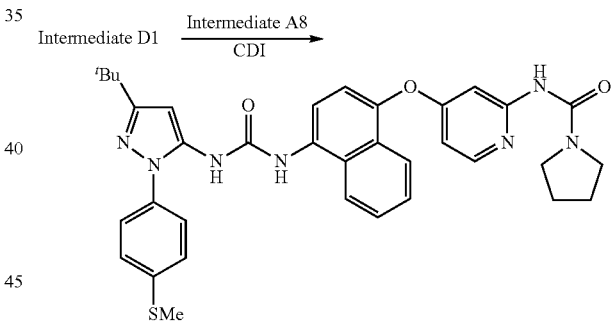

Example 14

To a solution of CD (93 mg, 0.57 mmol) in dry DCM (1.0 mL) was added Intermediate A8 (150 mg, 0.57 mmol) and the resulting solution maintained at RT for 3 hr. The reaction was diluted with DCM (2.0 mL) and Intermediate D1 (100 mg, 0.29 mmol) was added and the mixture kept at RT for 16 hr. The resulting mixture was diluted with DCM (10 mL) and was washed with water (10 ml) and brine (10 mL) and then dried and the volatiles evaporated in vacuo. The residue was purified by flash column chromatography (SiO$_2$, EtOAc in isohexane, 100%, gradient elution) and the product so obtained was further purified by trituration with ether (3 mL) to afford the title compound, Example 14, as a pale pink solid (102 mg, 55%); R$^t$ 5.32 min (Method 1 basic); m/z 636 (M+H)$^+$ (ES$^+$); $^1$H NMR (400 MHz, DMSO-d$_6$) δ: 1.29 (9H, s), 1.79 (4H, m), 2.54 (3H, s), 3.30 (4H, m, partially obscured by HOD peak), 6.41 (1H, s), 6.75 (1H, br s), 7.30 (1H, br s), 7.35 (1H, d), 7.44 (2H, d), 7.53 (2H, d), 7.59 (1H, m), 7.66 (1H, m), 7.83 (1H, d), 7.98 (1H, d), 8.12 (1H, d), 8.15 (1H, d), 8.88 (1H, s), 9.0 (1H, v br s), 9.19 (1H, s).

Example 15

3-(4-(4-(3-(3-tert-Butyl-1-(4-(methylsulfonyl)phenyl)-1H-pyrazol-5-yl)ureido)naphthalen-1-yloxy)pyridin-2-yl)-1,1-dimethylurea

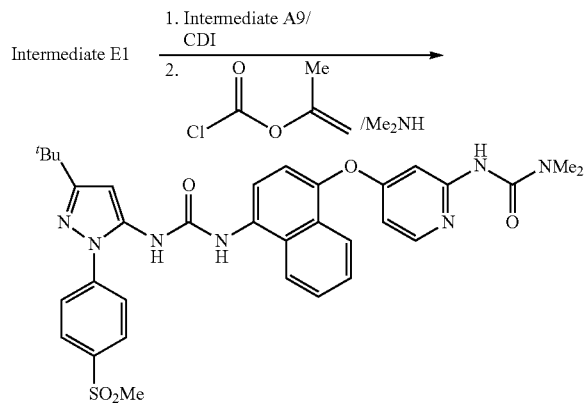

Example 15

To a solution of CDI (1.16 g, 7.16 mmol) in DCM (10.0 mL) was added Intermediate A9 (2.10 g, 7.16 mmol) and the mixture maintained at RT for 2 hr and then treated with a solution of Intermediate E1 (610 mg, 2.40 mmol) in DCM (4.0 mL). The reaction mixture was kept at RT for a further 24 hr, was quenched by the addition of MeOH (10 mL) and after 30 min at RT the volatiles were evaporated in vacuo. The residue was purified twice by flash column chromatography (SiO$_2$, 120 g, MeOH in DCM, 0-15%, gradient elution and then SiO$_2$, 120 g, MeOH in DCM, 0-10%, gradient elution) to afford 1-(4-((2-aminopyridin-4-yl)oxy)naphthalen-1-yl)-3-(3-tert-butyl-1-(4-(methylsulfonyl)phenyl)-1H-pyrazol-5-yl)urea as a brown solid (430 mg, 20%); Rt 1.76 min, (Method 2); m/z 571 (M+H)$^+$ (ES$^+$).

To a suspension of the product obtained above (216 mg, 0.379 mmol) and 4-methyl morpholine (75 µL, 0.68 mmol) in THF (3.5 mL) under nitrogen at −78° C. was added, dropwise, a solution of prop-1-en-2-yl carbonochloridate (74 µL, 0.68 mmol) in THF (1.8 mL). The reaction mixture was warmed to RT for 16 hr and was quenched with MeOH and evaporated in vacuo. The residue was taken up into MeOH (3.0 mL), kept at RT for 1 hr and the volatiles evaporated in vacuo. The residue was partitioned between DCM (5.0 mL) and water (5.0 mL) and the organic layer was separated, washed with brine (5.0 mL) and then dried and evaporated in vacuo to afford 1-(4-((2-di(prop-1-ene-2-yloxycarbonyl)aminopyridin-4-yl)oxy)naphthalen-1-yl)-3-(3-(tert-butyl)-1-(4-(methylsulfonyl)phenyl)-1H-pyrazol-5-yl)urea as a brown solid (250 mg, 74%, 83% purity); Rt 2.64 min, (Method 2); m/z 739 (M+H)$^+$ (ES$^+$). This material was used directly in the next step without further purification.

To a suspension of the bis carbamate intermediate obtained above (40 mg, 83% purity, 45 µmol) and 4-methylmorpholine (7.0 µL, 0.06 mmol) in THF (1.5 mL) was added dimethylamine (100 µL of a 2M solution in THF, 0.2 mmol) and the reaction mixture maintained at 55° C. for 15 hr and the volatiles then evaporated in vacuo. The residue was purified twice by flash column chromatography (SiO$_2$, 4.0 g, [5% MeOH in EtOAc] in isohexane, 20-100%, gradient elution, then SiO$_2$, 4.0 g, [5% MeOH in EtOAc] in isohexane, 0-100%, gradient elution) to afford the title compound, Example 15, as a grey solid (5.6 mg, 19%); Rt 1.92 min (Method 2); m/z 642 (M+H)$^+$ (ES$^+$); $^1$H NMR (400 MHz, DMSO-d$_6$) δ: 1.31 (9H, s), 2.85 (6H, s), 3.28 (3H, s), 6.49 (1H, s), 6.60 (1H, dd), 7.31 (1H, d), 7.38 (1H, d), 7.58 (1H, ddd), 7.66 (1H, ddd), 7.85 (1H, dd), 7.90-7.94 (3H, overlapping m), 8.08-8.12 (4H, overlapping m), 8.86 (1H, br s), 9.10 (1H, br s), 9.12 (1H, br s).

Example 16

N-(4-(4-(3-(3-tert-Butyl-1-(6-methoxypyridin-3-yl)-1H-pyrazol-5-yl)ureido)naphthalen-1-yloxy)pyridin-2-yl)-2-methoxyacetamide

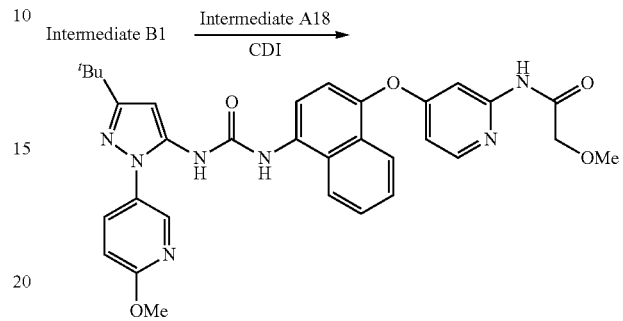

Example 16

To a suspension of CDI (62 mg, 0.38 mmol) in DCM (800 µL) was added Intermediate A18 (94 mg, 0.38 mmol) and the reaction mixture maintained at RT for 19 hr. An aliquot of this solution (650 µL, 0.31 mmol) was added to a solution of Intermediate B1 (60 mg, 0.19 mmol) in DCM (600 µL) and after 1.5 hr at RT a second aliquot of the activated pyrazole solution (50 µL, 0.02 mmol) was added and the mixture kept at RT for 20 hr. The reaction was quenched with MeOH (3.0 mL) and after 1 hr at RT was evaporated in vacuo. The residue was purified by flash column chromatography (SiO$_2$, 12 g, EtOAc in isohexane, 0-100%, gradient elution) to afford the title compound, Example 16, as a brown solid (79 mg, 85%); R$^t$ 4.99 min (Method 1 basic); m/z 596 (M+H)$^+$ (ES$^+$); $^1$H NMR (400 MHz, DMSO-d$_6$) δ: 1.28 (9H, s), 3.30 (3H, s), 3.93 (3H, s), 3.98 (2H, s), 6.42 (1H, s), 6.69 (1H, dd), 7.02 (1H, d), 7.33 (1H, d), 7.57 (1H, m), 7.63-7.66 (2H, overlapping m), 7.84 (1H, d), 7.90 (1H, dd), 7.93 (1H, d), 8.07 (1H, d), 8.18 (1H, d), 8.39 (1H, dd), 8.82 (1H, s), 9.09 (1H, s), 10.03 (1H, s).

Example 17

N-(4-(4-(3-(3-tert-Butyl-1-(6-hydroxypyridin-3-yl)-1H-pyrazol-5-yl)ureido) naphthalen-1-yloxy)pyridin-2-yl)-2-methoxyacetamide

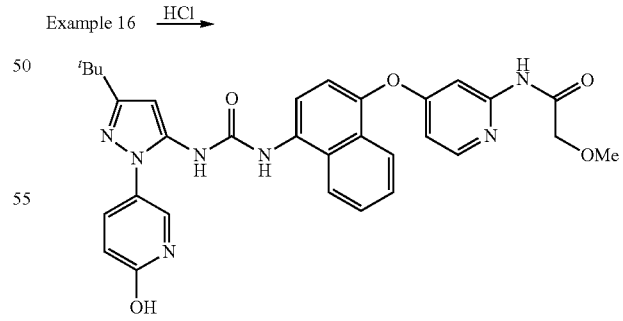

Example 17

To a solution of Example 16 (44 mg, 0.073 mmol) in dioxane (1.0 mL) was added HCl (4M in dioxane. 220 µL, 0.88 mmol) and the reaction mixture heated to 60° C. for 2 hr, during which time a grey solid precipitated and then redissolved. The reaction mixture was cooled to RT and was diluted with MeOH and purified by SCX capture and release.

The crude product so obtained was purified by flash column chromatography (SiO$_2$, 4.0 g, EtOAc, isocratic elution and then 10% MeOH in DCM, isocratic elution) to afford the title compound, Example 17, as a pink solid (29 mg, 66%); Rt 4.30 min (Method 1 basic); m/z 582 (M+H)$^+$ (ES$^+$); $^1$H NMR (400 MHz, DMSO-d$_6$) δ: 1.26 (9H, s), 3.30 (3H, s), 3.99 (2H, s), 6.37 (1H, s), 6.49 (1H, d), 6.72 (1H, dd), 7.35 (1H, d), 7.57-7.60 (2H, overlapping m), 7.65 (1H, d), 7.68 (1H, m), 7.76 (1H, br s), 7.84 (1H, d), 7.96 (1H, d), 8.11 (1H, d), 8.19 (1H, d), 8.82 (1H, s), 9.12 (1H, s), 10.10 (1H, s), 11.99 (1H, s).

Example 18

N-(4-(4-(3-(3-tert-Butyl-1-(4-methylthiophen-2-yl)-1H-pyrazol-5-yl)ureido) naphthalen-1-yloxy)pyridin-2-yl)-2-methoxyacetamide

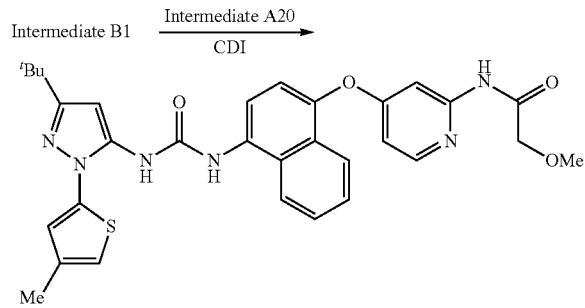

Example 18

To a suspension of CDI (69 mg, 0.43 mmol) in DCM (1.0 mL) was added Intermediate A20 (100 mg, 0.43 mmol) and the reaction mixture maintained at RT for 19 hr and then treated with Intermediate B1 (110 mg, 0.34 mmol). After 1.5 hr at RT MeOH (2.0 mL) was added and the reaction mixture kept at RT for 10 min and then evaporated in vacuo. The residue was purified by flash column chromatography (SiO$_2$, 12 g, MeOH in DCM, 0-5%, gradient elution) to afford the title compound, Example 18, as a pale purple solid (128 mg, 56%); 2.58 min (Method 2); m/z 585 (M+H)$^+$ (ES$^+$); $^1$H NMR (400 MHz, DMSO-d$_6$) δ: 1.26 (9H, s), 2.26 (3H, d), 3.30 (3H, s), 3.98 (2H, s), 6.40 (1H, s), 6.70 (1H, dd), 7.09-7.11 (2H, overlapping m), 7.35 (1H, d), 7.58 (1H, m), 7.64-7.69 (2H, overlapping m), 7.84 (1H, d), 7.96 (1H, dd), 8.15 (1H, d), 8.18 (1H, d), 8.88 (1H, s), 9.25 (1H, s), 10.06 (1H, s).

Example 19

N-(4-((4-(3-(1,3-Diphenyl-1H-pyrazol-5-yl)ureido) naphthalen-1-yl)oxy)pyridin-2-yl)-2-methoxyacetamide

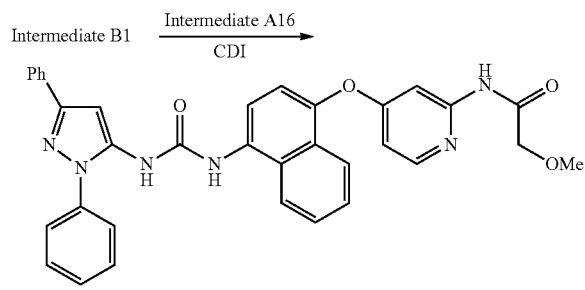

Example 19

To a suspension of CDI (121 mg, 0.746 mmol) in DCM (1 mL) was added 1,3-diphenyl-1H-pyrazol-5-amine, Intermediate A16, (175 mg, 0.744 mmol) and the reaction mixture maintained at RT for 2 hr and then treated with solid Intermediate B1 (150 mg, 0.46 mmol) and diluted with DCM (2.0 mL). After 16 hr at RT the reaction was quenched by the addition of MeOH (2.0 mL) and after a further 10 min the volatiles were evaporated in vacuo. The residue was purified by trituration with a mixture of DCM/MeOH (8/2 v/v) and then water (20 mL) and the solid was isolated by filtration and dried in vacuo to afford the title compound, Example 19, as a pale purple solid (736 mg, 26%); R$^r$ 5.09 min (Method 1, basic); m/z 585 (M+H)$^+$ (ES$^+$); $^1$H NMR (400 MHz, DMSO-d$_6$) δ: 3.30 (3H, s), 3.99 (2H, s), 6.71 (1H, dd), 7.00 (1H, s), 7.33-7.37 (2H, overlapping m), 7.42-7.46 (2H, overlapping m), 7.52 (1H, tt), 7.56-7.72 (7H, overlapping m), 7.84-7.88 (3H, overlapping m), 7.97 (1H, d), 8.10 (1H, d), 8.19 (1H, d), 9.00 (1H, br s), 9.20 (1H, br s), 10.06 (1H, br s).

Example 20

2-Methoxy-N-(4-(4-(3-(3-(4-methyltetrahydro-2H-pyran-4-yl)-1-p-tolyl-1H-pyrazol-5-yl)ureido)naphthalen-1-yloxy)pyridin-2-yl)acetamide

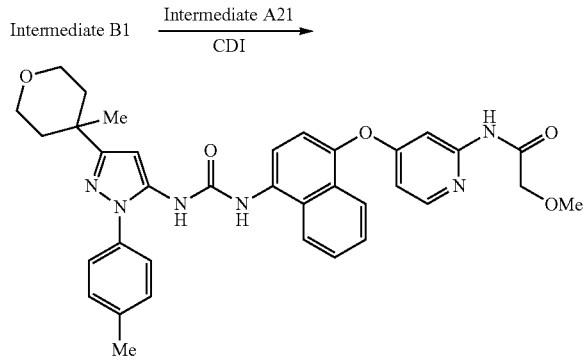

Example 20

To a suspension of CDI (113 mg, 0.696 mmol) in DCM (2.0 mL) was added Intermediate A21 (189 mg, 0.696 mmol) and the reaction mixture maintained at RT for 3 hr. A solution of Intermediate B1 (150 mg, 0.464 mmol) in DCM (2.0 mL) was added and after 72 hr at RT the reaction mixture was partitioned between DCM (15 mL) and water (15 mL). The organic layer was separated and was washed with brine (15 mL) and then dried and evaporated in vacuo. The residue was purified three times by flash column chromatography (SiO$_2$, EtOAc in isohexane, 30-100%, gradient elution; then SiO$_2$, EtOAc in isohexane, 60-100%, gradient elution; then SiO$_2$, MeOH in DCM, 0-5%, gradient elution). The impure product so obtained was purified by preparative HPLC to afford the title compound, Example 20, as an off-white solid (60 mg, 20%); R$^r$ 4.99 min (Method 1 basic); m/z 621 (M+H)$^+$ (ES$^+$); $^1$H NMR (400 MHz, DMSO-d$_6$) δ: 1.26 (3H, s), 1.57 (2H, m), 2.05 (2H, m), 2.40 (3H, s), 3.30 (3H, s), 3.53 (2H, m), 3.66 (2H, m), 3.98 (2H, s), 6.42 (1H, s), 6.70 (1H, dd), 7.34 (1H, d), 7.38 (2H, d), 7.47 (2H, d), 7.57 (1H, m), 7.63-7.66 (2H, overlapping m), 7.83 (1H, d), 7.96 (1H, dd), 8.08 (1H, d), 8.18 (1H, d), 8.84 (1H, s), 9.14 (1H, s), 10.04 (1H, s).

Example 21

N-(4-(4-(3-(3-tert-Butyl-1-p-tolyl-1H-pyrazol-5-yl)ureido)naphthalen-1-yl thio)pyridin-2-yl)-2-methoxyacetamide

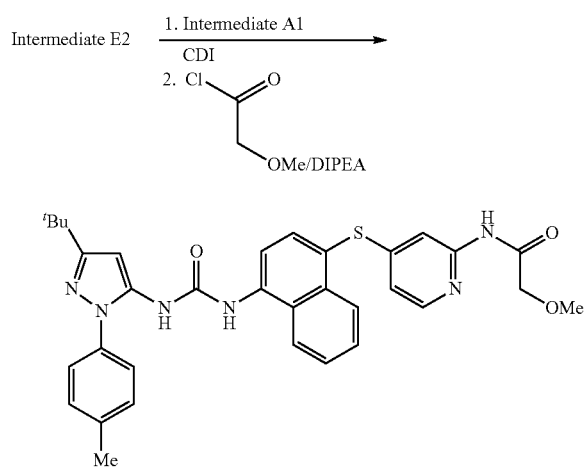

Example 21

Example 22

N-(4-(4-(3-(3-(tert-Butyl)-1-(p-tolyl)-1H-pyrazol-5-yl)ureido)-1-naphthoyl)pyridin-2-yl)-2-(2-methoxyethoxy)acetamide

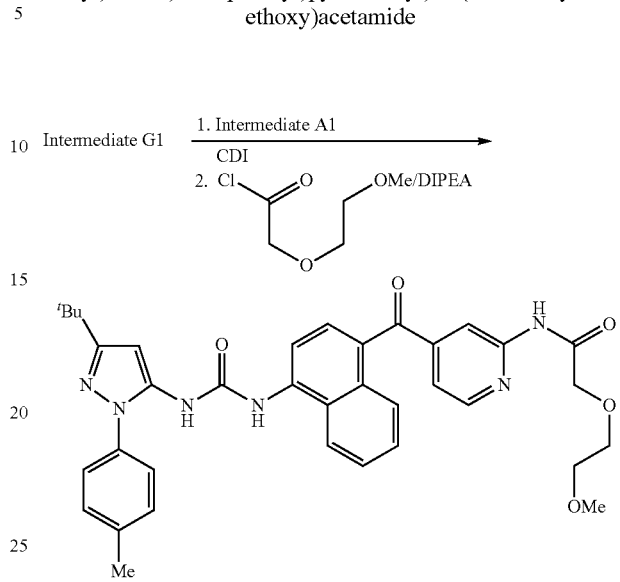

Example 22

To a suspension of CDI (206 mg, 1.27 mmol) in DCM (10 mL) was added Intermediate A1 (292 mg, 1.27 mmol) portion-wise over 30 min and the reaction mixture maintained at RT for 1 hr. An aliquot of this mixture (8.0 mL, 1.0 mmol) was added to a solution of Intermediate E1 (200 mg, 0.75 mmol) in DCM (5.0 mL). On completion of the addition the reaction was quenched with MeOH (5.0 mL) and the mixture was evaporated in vacuo. The residue was purified by flash column chromatography (SiO$_2$, 40 g, MeOH in DCM, 2-5%, gradient elution) to afford 1-(4-(2-aminopyridin-4-ylthio)naphthalen-1-yl)-3-(3-tert-butyl-1-p-tolyl-1H-pyrazol-5-yl) urea as a pale yellow solid (139 mg, 35%); R$^t$ 1.99 min (Method 2); m/z 523 (M+H)$^+$ (ES$^+$).

To a solution of 1-(4-(2-aminopyridin-4-ylthio)naphthalen-1-yl)-3-(3-tert-butyl-1-p-tolyl-1H-pyrazol-5-yl)urea (44 mg, 0.084 mmol) and DIPEA (52 µL, 0.30 mmol) in DCM (2.0 mL) was added a solution of 2-methoxyacetyl chloride (19 µL, 0.21 mmol) in DCM (0.5 mL) over 5 min. The reaction mixture was kept at RT for 30 min and a solution of NH$_3$ (1% in MeOH, 1.0 mL) was added. The mixture was evaporated in vacuo and the residue was purified by flash column chromatography (SiO$_2$, 12 g, EtOAc in isohexane, 30-80%, gradient elution) to afford the title compound, Example 21, as a white solid (36 mg, 70%). R$^t$ 2.76 min (Method 2); m/z 595 (M+H)$^+$ (ES$^+$); $^1$H NMR (400 MHz, DMSO-d$_6$) δ: 1.28 (9H, s), 2.39 (3H, s), 3.28 (3H, s), 3.95 (2H, s), 6.44 (1H, s), 6.56 (1H, dd), 7.37 (2H, d), 7.47 (2H, d), 7.65 (2H, m), 7.75 (1H, s), 7.93 (1H, d), 8.02 (1H, d), 8.17-8.23 (3H, overlapping m), 8.97 (1H, s), 9.37 (1H, s), 9.90 (1H, s).

To a solution of CDI (308 mg, 1.90 mmol) in dry DCM (2.5 mL) under N$_2$ was added Intermediate A1 (435 mg, 1.90 mmol) portion-wise over 45 min. After a further 45 min an aliquot of this solution (500 µL, 0.40 mmol) was added to a suspension of Intermediate G1 (200 mg, 0.760 mmol) in dry THF (6.0 mL) at 0° C. The mixture was maintained at 0° C. for 1.5 hr and was then diluted with dry DMF (3.0 mL) and treated with an additional aliquot of the CDI-adduct solution (500 µL, 0.40 mmol). The reaction mixture was warmed to RT and further aliquots of CDI adduct solution (500 µL, 0.40 mmol) were added after 4 hr and 6 hr.

After 22 hr a second batch of the CDI adduct was prepared in an identical manner to that described above and aliquots of this solution were added to the reaction mixture at 24 hr (500 µL, 0.40 mmol), then at 26 hr (1.0 mL, 0.70 mmol) and finally 29 hr (1.0 mL, 0.70 mmol). After 50 hr the reaction mixture was partitioned between EtOAc and water. The aq. layer was separated and was extracted twice with EtOAc and the combined organic extracts were washed with brine and then dried and evaporated in vacuo. The residue was purified by flash column chromatography (SiO$_2$, 40 g, [5% MeOH in EtOAc] in isohexane, 0-85%, gradient elution) to afford 1-(4-(2-aminoisonicotinoyl)naphthalen-1-yl)-3-(3-(tert-butyl)-1-(p-tolyl)-1H-pyrazol-5-yl)urea as a yellow solid (130 mg, 32%); Rt 1.87 min (Method 2); m/z 519 (M+H)$^+$ (ES$^+$).

To a solution of 1-(4-(2-aminoisonicotinoyl)naphthalen-1-yl)-3-(3-(tert-butyl)-1-(p-tolyl)-1H-pyrazol-5-yl)urea (38.0 mg, 0.073 mmol) and DIPEA (64 µL, 0.37 mmol) in dry THF (4.0 mL) under N$_2$ at 0° C. was added 2-(2-methoxyethoxy)acetyl chloride (45.0 mg, 0.29 mmol). The reaction mixture was maintained at 0° C. for 30 min and was then warmed to RT for 1.5 hr. The reaction was quenched by the addition of a solution of NH$_3$ (1% in MeOH, 3.0 mL) and after a further 45 min at RT was evaporated in vacuo. The residue was purified by SCX capture and release followed by flash column chromatography (SiO$_2$, 12 g, [5% MeOH in EtOAc] in isohexane, 0-60%, gradient elution) to afford the title compound, Example 22, as a yellow solid (21 mg, 44%); Rt 2.67 min (Method 2); m/z 635 (M+H)$^+$ (ES$^+$); $^1$H NMR (400 MHz, DMSO-d$_6$) δ: 1.29 (9H, s), 2.39 (3H, s), 3.29 (3H, s), 3.50 (2H, m), 3.66 (2H, m), 4.14 (2H, s), 6.45 (1H, s), 7.35-7.37 (3H, overlapping m), 7.46 (2H, d), 7.67-7.73 (3H, overlapping m), 8.20 (2H, m), 8.37 (1H, s), 8.49 (1H, m), 8.54 (1H, d), 9.03 (1H, s), 9.47 (1H, s), 10.24 (1H, s).

Example 23

1-(3-(tert-Butyl)-1-(p-tolyl)-1H-pyrazol-5-yl)-3-(4-((2-(3-ethylureido)pyridin-4-yl)methyl)naphthalen-1-yl)urea

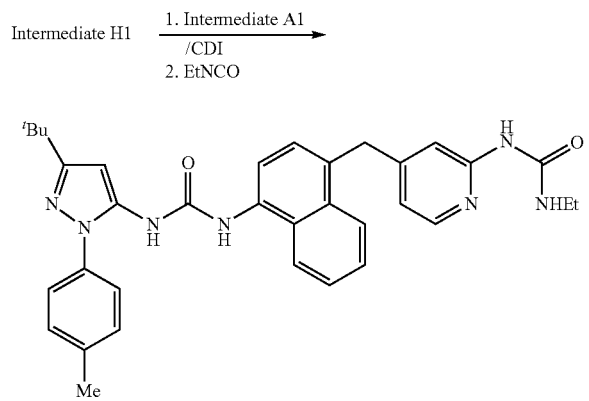

Example 23

To a suspension of CDI (244 mg, 1.50 mmol) in dry DCM (2.5 mL) under N$_2$ was added Intermediate A1 (345 mg, 1.50 mmol) portion-wise over 35 min. After 1.5 hr an aliquot of this mixture (0.5 mL, 0.3 mmol) was added to a solution of Intermediate H1 (150 mg, 0.60 mmol) under N$_2$ at 0° C. and further aliquots of the CDI adduct were added after 1 hr (0.5 mL, 0.3 mmol) and after 1.5 hr (0.3 mL, 0.2 mmol). The reaction mixture was warmed to RT for 18 hr then cooled to 0° C. and a further aliquot of the CDI-adduct (0.25 mL, 0.15 mL) was added. The resulting mixture was warmed to RT for 1 hr and was then partitioned between DCM and water. The aq. layer was extracted with DCM and the combined organic extracts were washed with brine, and then dried and evaporated in vacuo. The residue was purified by flash column chromatography (SiO$_2$, 40 g, [5% MeOH in EtOAc] in isohexane, 20-90%, gradient elution) to afford 1-(4-((2-aminopyridin-4-yl)methyl)naphthalen-1-yl)-3-(3-(tert-butyl)-1-(p-tolyl)-1H-pyrazol-5-yl)urea as a beige powder (166 mg, 49%); R$^t$ 1.74 min (Method 2); m/z 505 (M+H)$^+$ (ES$^+$).

To a solution of 1-(4-((2-aminopyridin-4-yl)methyl)naphthalen-1-yl)-3-(3-(tert-butyl)-1-(p-tolyl)-1H-pyrazol-5-yl)urea (55 mg, 0.11 mmol) in dry DCM (4.0 mL) under N$_2$ at 0° C. was added ethyl isocyanate (22 μL, 0.27 mmol). The reaction mixture was maintained at 0° C. for 20 min, was then warmed to RT for 2 hr and dry DMF (200 μL) was added. Additional aliquots of ethyl isocyanate were added after 3.5 hr (22 μL, 0.27 mmol), after 21 hr (43 μL, 0.54 mmol) and after 28 hr (65 μL, 0.81 mmol). After 43 hr the reaction was quenched by the addition of a solution of NH$_3$ (1% in MeOH, 3.0 mL) and after 45 min the resulting mixture was evaporated in vacuo. The residue was subjected to SCX capture and release and the crude product so obtained was purified by flash column chromatography (SiO$_2$, 12 g, [5% MeOH in EtOAc] in isohexane, 0-80%, gradient elution) to afford the title compound, Example 23, as a white solid (26 mg, 40%); R$^t$ 2.22 min (Method 2); m/z 576 (M+H)$^+$ (ES$^+$); $^1$H NMR (400 MHz, DMSO-d$_6$) δ: 1.04 (3H, t), 1.28 (9H, s), 2.39 (3H, s), 3.14 (2H, m), 4.33 (2H, s), 6.40 (1H, s), 6.76 (1H, dd), 7.16 (1H, s), 7.36 (2H, d), 7.39 (1H, d), 7.45 (2H, d), 7.53 (2H, m), 7.87 (1H, d), 7.92 (1H, d), 8.01-8.04 (2H, overlapping m), 8.15 (1H, br t), 8.78 (1H, s), 9.04 (1H, s), 9.07 (1H, s).

Further compound examples listed below (Table 3) have been prepared from appropriate intermediates disclosed herein, using one or more of the methods described above. Unless otherwise indicated all NMR spectroscopic data reported in the table was acquired at 400 MHz using DMSO-d$_6$ as the solvent.

TABLE 3

Additional Compound Examples of the Invention

| Ex. No. | Structure | Name and Analytical Data |
|---|---|---|
| 24 | 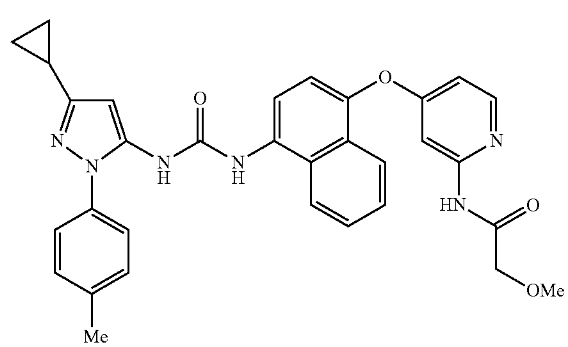 [SMILES: COCC(=O)Nc1cc(Oc2ccc(NC(=O)Nc3cc(C4CC4)nn3-c3ccc(C)cc3)c3ccccc23)ccn1] | N-(4-((4-(3-(3-cyclopropyl-1-p-tolyl-1H-pyrazol-5-yl)ureido)naphthalen-1-yl)oxy)pyridin-2-yl)-2-methoxyacetamide. R$^t$ 4.70 min (Method 1, basic); m/z 564 (M + H)$^+$ (ES$^+$); $^1$H NMR δ: 0.67-0.70 (2H, overlapping m), 0.85-0.90 (2H, overlapping m), 1.87 (1H, m), 2.39 (3H, s), 3.30 (3H, s), 3.98 (2H, s), 6.20 (1H, s), 6.69 (1H, dd), 7.32-7.37 (3H, overlapping m), 7.43-7.45 (2H, overlapping m), 7.55-7.58 (1H, m), 7.62-7.66 (2H, overlapping m), 7.83 (1H, d), 7.95 (1H, d), 8.07 (1H, d), 8.18 (1H, d), 8.78 (1H, s), 9.10 (1H, s), 10.01 (1H, s). |

TABLE 3-continued

Additional Compound Examples of the Invention

| Ex. No. | Structure | Name and Analytical Data |
|---|---|---|
| 25 | 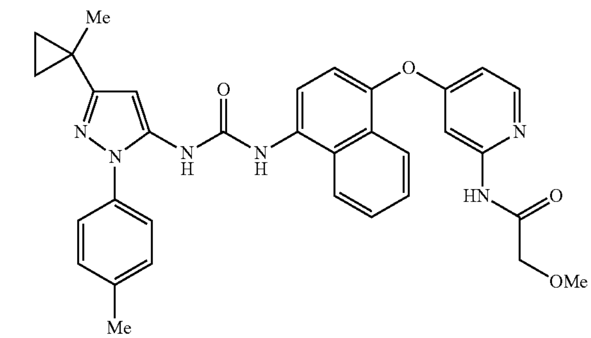 [SMILES: COCC(=O)Nc1cc(Oc2ccc(NC(=O)Nc3cc(C4(C)CC4)nn3-c3ccc(C)cc3)c3ccccc23)ccn1] | 2-methoxy-N-(4-(4-(3-(3-(1-methylcyclopropyl)-1-p-tolyl-1H-pyrazol-5-yl)ureido)naphthalen-1-yloxy)pyridin-2-yl)acetamide. $R^t$ 2.51 min (Method 2); m/z 577 (M + H)$^+$ (ES$^+$); $^1$H NMR δ: 0.72 (2H, q), 0.91 (2H, q), 1.40 (3H, s), 2.39 (3H, s), 3.30 (3H, s), 3.98 (2H, s), 6.27 (1H, s), 6.69 (1H, dd), 7.32-7.37 (3H, overlapping m), 7.43-7.45 (2H, overlapping m), 7.57 (1H, m), 7.62-7.66 (2H, overlapping m), 7.83 (1H, d), 7.95 (1H, d), 8.07 (1H, d), 8.16 (1H, d), 8.77 (1H, s), 9.10 (1H, s), 10.01 (1H, s). |
| 26 | 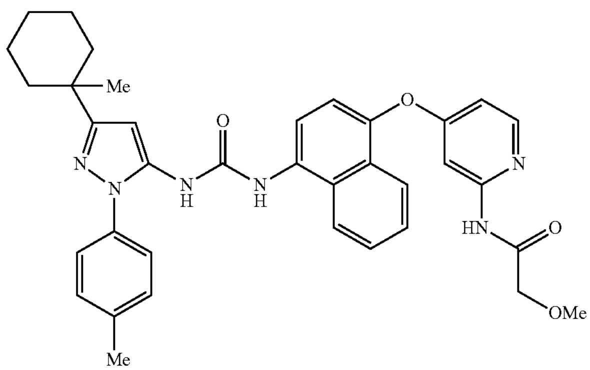 [SMILES: COCC(=O)Nc1cc(Oc2ccc(NC(=O)Nc3cc(C4(C)CCCCC4)nn3-c3ccc(C)cc3)c3ccccc23)ccn1] | 2-methoxy-N-(4-(4-(3-(3-(1-methylcyclohexyl)-1-p-tolyl-1H-pyrazol-5-yl)ureido)naphthalen-1-yloxy)pyridin-2-yl)acetamide. $R^t$ 2.97 min (Method 2); m/z 619 (M + H)$^+$ (ES$^+$); $^1$H NMR δ: 0.81-0.87 (2H, overlapping m), 1.20 (3H, s), 1.44-1.51 (8H, overlapping m), 1.98-2.01 (2H, overlapping m), 2.39 (3H, s), 3.30 (3H, s), 3.98 (2H, s), 6.39 (1H, s), 6.70 (1H, dd), 7.33-7.39 (3H, overlapping m), 7.45-7.48 (2H, overlapping m), 7.58 (1H, m), 7.63-7.66 (2H, overlapping m), 7.84 (1H, d), 7.98 (1H, d), 8.10 (1H, d), 8.19 (1H, d), 8.82 (1H, s), 9.14 (1H, s), 10.05 (1H, s). |
| 27 | 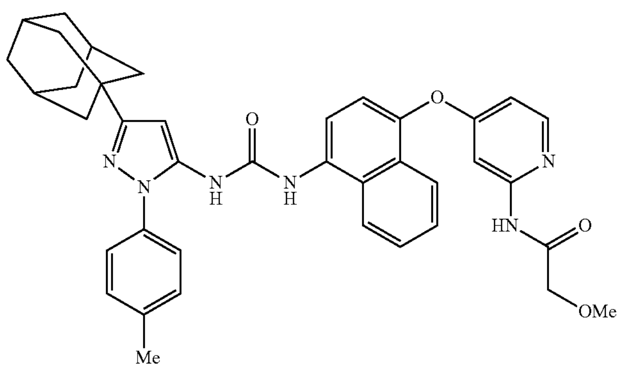 [SMILES: COCC(=O)Nc1cc(Oc2ccc(NC(=O)Nc3cc(C45CC6CC(CC(C6)C4)C5)nn3-c3ccc(C)cc3)c3ccccc23)ccn1] | N-(4-(4-(3-(3-(adamantan-1-yl)-1-p-tolyl-1H-pyrazol-5-yl)ureido)naphthalen-1-yloxy)pyridin-2-yl)-2-methoxyacetamide. $R^t$ 5.52 min (Method 1, basic); m/z 577 (M + H)$^+$ (ES$^+$); $^1$H NMR δ: 1.73 (6H, s), 1.91 (6H, d), 2.02 (3H, s), 2.39 (3H, s), 3.29 (3H, s), 3.98 (2H, s), 6.37 (1H, s), 6.69 (1H, dd), 7.32-7.38 (3H, overlapping m), 7.44-7.46 (2H, overlapping m), 7.57 (1H, m), 7.62-7.66 (2H, overlapping m), 7.83 (1H, d), 7.96 (1H, d), 8.08 (1H, d), 8.16 (1H, d), 8.78 (1H, s), 9.12 (1H, s), 10.04 (1H, s). |
| 28 | 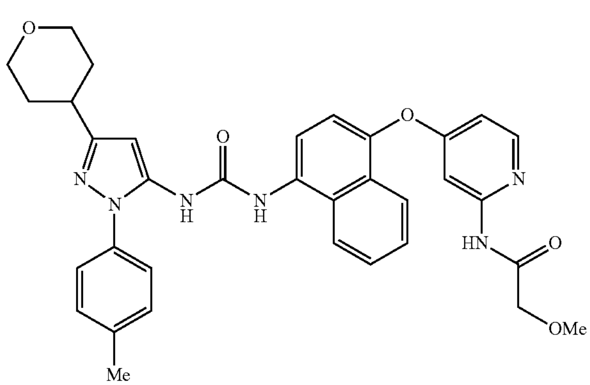 [SMILES: COCC(=O)Nc1cc(Oc2ccc(NC(=O)Nc3cc(C4CCOCC4)nn3-c3ccc(C)cc3)c3ccccc23)ccn1] | 2-methoxy-N-(4-(4-(3-(3-(tetrahydro-2H-pyran-4-yl)-1-p-tolyl-1H-pyrazol-5-yl)ureido)naphthalen-1-yloxy)pyridin-2-yl)acetamide. $R^t$ 4.53 min (Method 1, basic); m/z 606 (M + H)$^+$ (ES$^+$); $^1$H NMR δ: 1.61-1.72 (2H, overlapping m), 1.82-1.85 (2H, overlapping m), 2.32 (3H, s), 2.83 (1H, m), 3.30 (3H, s), 3.41-3.46 (2H, overlapping m), 3.90-3.93 (2H, overlapping m), 3.98 (2H, s), 6.38 (1H, s), 6.69 (1H, dd), 7.33-7.39 (3H, overlapping m), 7.57 (1H, m), 7.63-7.67 (2H, overlapping m), 7.83 (1H, d), 7.96 (1H, d), 8.08 (1H, d), 8.18 (1H, d), 8.82 (1H, s), 9.13 (1H, s), 10.04 (1H, s). |

TABLE 3-continued

Additional Compound Examples of the Invention

| Ex. No. | Structure | Name and Analytical Data |
|---|---|---|
| 29 | 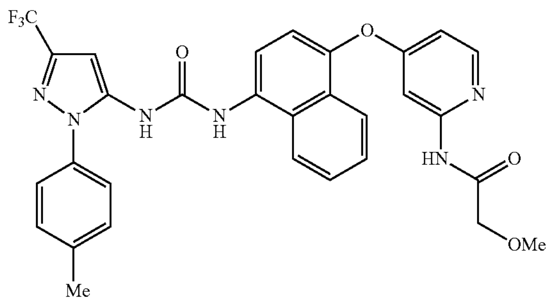 [SMILES: COCC(=O)Nc1cc(Oc2ccc(NC(=O)Nc3cc(C(F)(F)F)nn3-c3ccc(C)cc3)c3ccccc23)ccn1] | 2-methoxy-N-(4-(4-(3-(1-p-tolyl-3-(trifluoromethyl)-1H-pyrazol-5-yl)ureido)naphthalen-1-yloxy)pyridin-2-yl)acetamide. $R^t$ 4.80 min (Method 1, basic); m/z 591 (M + H)$^+$ (ES$^+$); $^1$H NMR δ: 2.43 (3H, s), 3.29 (3H, s), 3.98 (2H, s), 6.70 (1H, dd), 6.90 (1H, s), 7.35 (1H, d), 7.46 (1H, d), 7.54-7.59 (3H, overlapping m), 7.63-7.67 (2H, overlapping m), 7.84 (1H, d), 7.95 (1H, d), 8.06 (1H, d), 8.19 (1H, d), 9.12 (1H, s), 9.24 (1H, s), 10.04 (1H, s). |
| 30 | 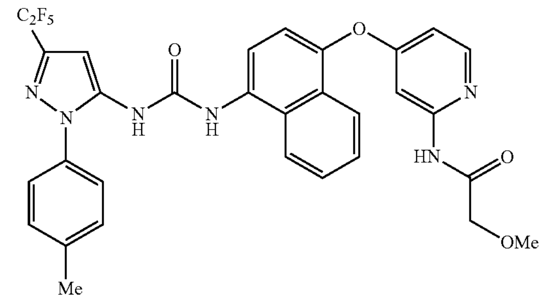 | 2-methoxy-N-(4-(4-(3-(3-(perfluoroethyl)-1-p-tolyl-1H-pyrazol-5-yl)ureido)naphthalen-1-yloxy)pyridin-2-yl)acetamide. $R^t$ 4.99 min (Method 1, basic); m/z 641 (M + H)$^+$ (ES$^+$); $^1$H NMR δ: 2.43 (3H, s), 3.29 (3H, s), 3.98 (2H, s), 6.70 (1H, dd), 6.92 (1H, s), 7.35 (1H, d), 7.45-7.47 (2H, overlapping m), 7.54-7.57 (3H, overlapping m), 7.64-7.67 (2H, overlapping m), 7.84 (1H, d), 7.96 (1H, d), 8.07 (1H, d), 8.17 (1H, d), 9.16 (1H, s), 9.27 (1H, s), 10.07 (1H, s). |
| 31 | 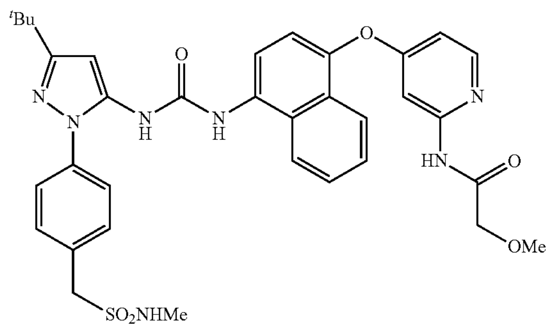 | N-(4-(4-(3-(3-tert-butyl-1-(4-((N-methyl sulfamoyl)methyl)phenyl)-1H-pyrazol-5-yl)ureido)naphthalen-1-yloxy)pyridin-2-yl)-2-methoxyacetamide. $R^t$ 2.19 min (Method 2); m/z 672 (M + H)$^+$ (ES$^+$); $^1$H NMR δ: 1.29 (9H, s), 2.63 (3H, d), 3.30 (3H, s), 3.99 (2H, s), 4.43 (2H, s), 6.43 (1H, s), 6.72 (1H, dd), 7.01 (1H, dd), 7.34 (1H, d), 7.54-7.58 (3H, overlapping m), 7.60-7.69 (4H, overlapping m), 7.84 (1H, d), 7.97 (1H, d), 8.13 (1H, d), 8.19 (1H, d), 8.92 (1H, br s), 9.18 (1H, brs), 10.09 (1H, br s). |
| 32 | 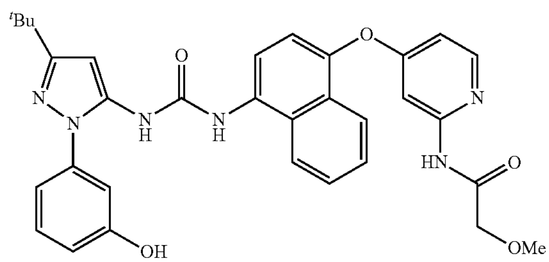 [SMILES: COCC(=O)Nc1cc(Oc2ccc(NC(=O)Nc3cc(C(C)(C)C)nn3-c3cccc(O)c3)c3ccccc23)ccn1] | N-(4-(4-(3-(3-tert-butyl-1-(3-hydroxyphenyl)-1H-pyrazol-5-yl)ureido)naphthalen-1-yloxy)pyridin-2-yl)-2-methoxyacetamide. $R^t$ 4.52 min (Method 1, basic); m/z 581 (M + H)$^+$ (ES$^+$); $^1$H NMR δ: 1.28 (9H, s), 3.30 (3H, s), 3.99 (2H, s), 6.41 (1H, s), 6.70 (1H, dd), 6.83 (1H, m), 6.99-7.03 (2H, overlapping m), 7.34-7.38 (2H, overlapping m), 7.58 (1H, br t), 7.64-7.68 (2H, overlapping m), 7.84 (1H, d), 7.99 (1H, d), 8.12 (1H, d), 8.18 (1H, d), 8.88 (1H, s), 9.18 (1H, s), 9.86 (1H, s), 10.07 (1H, s). |
| 33 | 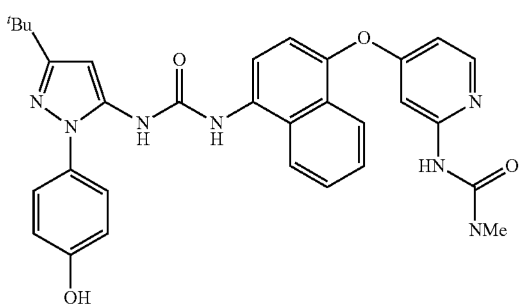 | 1-(3-tert-butyl-1-(4-hydroxyphenyl)-1H-pyrazol-5-yl)-3-(4-(2-(3-methylureido)pyridin-4-yloxy)naphthalen-1-yl)urea. $R^t$ 1.84 min (Method 2); m/z 566 (M + H)$^+$ (ES$^+$); $^1$H NMR δ: 1.27 (9H, s), 2.66 (3H, d), 6.37 (1H, s), 6.56 (1H, dd), 6.87 (1H, d), 6.92-6.94 (2H, overlapping m), 7.30-7.35 (3H, overlapping m), 7.57 (1H, t), 7.64 (1H, t), 7.82 (1H, d), 7.91 (1H, br s), 7.96 (1H, d), 8.05-8.09 (2H, overlapping m), 8.70 (1H, br s), 9.11 (1H, brs), 9.14 (1H, br s), 9.81 (1H, br s). |

TABLE 3-continued

Additional Compound Examples of the Invention

| Ex. No. | Structure | Name and Analytical Data |
|---|---|---|
| 34 | 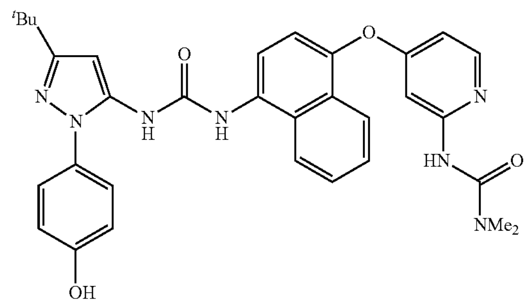 | 3-(4-(4-(3-(3-tert-butyl-1-(4-hydroxyphenyl)-1H-pyrazol-5-yl)ureido)naphthalen-1-yloxy)pyridin-2-yl)-1,1-dimethylurea. $R^t$ 2.31 min (Method 2); m/z 580 (M + H)$^+$ (ES$^+$); $^1$H NMR δ: 1.27 (9H, s), 2.86 (6H, s), 6.37 (1H, s), 6.59 (1H, dd), 6.93 (2H, d), 7.29-7.35 (3H, overlapping m), 7.38 (1H, d), 7.57 (1H, m), 7.65 (1H, m), 7.83 (1H, br d), 7.96 (1H, d), 8.07 (1H, br d), 8.10 (1H, d), 8.70 (1H, s), 8.86 (1H, s), 9.12 (1H, s), 9.80 (1H, s). |
| 35 | 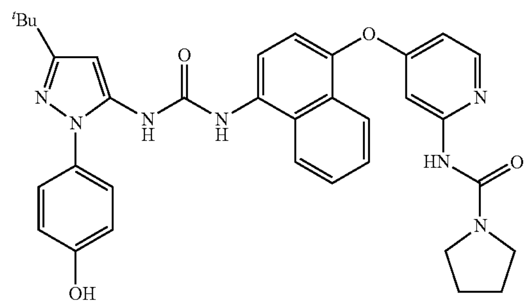 [SMILES: CC(C)(C)c1cc(NC(=O)Nc2ccc(Oc3ccnc(NC(=O)N4CCCC4)c3)c3ccccc23)n(-c2ccc(O)cc2)n1] | N-(4-(4-(3-(3-tert-butyl-1-(4-hydroxyphenyl)-1H-pyrazol-5-yl)ureido)naphthalen-1-yloxy)pyridin-2-yl)pyrrolidine-1-carboxamide. $R^t$ 4.64 min (Method 1, basic); m/z 607 (M + H)$^+$ (ES$^+$); $^1$H NMR δ: 1.26 (9H, s), 1.79 (4H, s), 3.31 (4H, s), 6.38 (1H, s), 6.91-6.94 (3H, overlapping m), 7.32-7.44 (4H, overlapping m), 7.59 (1H, m), 7.66 (1H, m), 7.82 (1H, d), 8.00 (1H, d), 8.12-8.18 (2H, overlapping m), 8.77 (1H, s), 9.22 (1H, s), 9.82 (1H, s). |
| 36 | 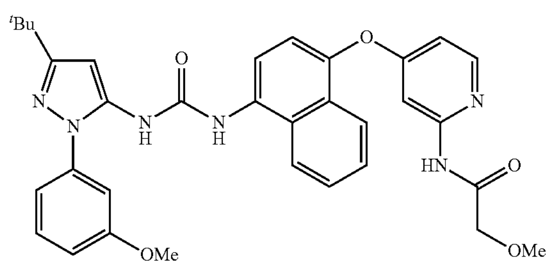 [SMILES: COCC(=O)Nc1cc(Oc2ccc(NC(=O)Nc3cc(C(C)(C)C)nn3-c3cccc(OC)c3)c3ccccc23)ccn1] | N-(4-(4-(3-(3-tert-butyl-1-(3-methoxyphenyl)-1H-pyrazol-5-yl)ureido)naphthalen-1-yloxy)pyridin-2-yl)-2-methoxyacetamide. $R^t$ 2.47 min (Method 2); m/z 595 (M + H)$^+$ (ES$^+$); $^1$H NMR δ: 1.29 (9H, s), 3.30 (3H, s), 3.83 (3H, s), 3.99 (2H, s), 6.43 (1H, s), 6.70 (1H, dd), 7.01-7.03 (1H, m), 7.16-7.18 (2H, overlapping m), 7.34 (1H, d), 7.47 (1H, t), 7.58 (1H, br t), 7.63-7.67 (2H, overlapping m), 7.84 (1H, d), 7.95 (1H, d), 8.10 (1H, d), 8.17 (1H, d), 8.85 (1H, s), 9.16 (1H, s), 10.06 (1H, s). |
| 37 | 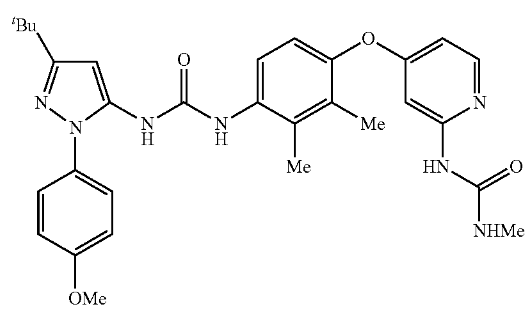 [SMILES: CNC(=O)Nc1cc(Oc2ccc(NC(=O)Nc3cc(C(C)(C)C)nn3-c3ccc(OC)cc3)c(C)c2C)ccn1] | 1-(4-(4-(3-(3-tert-butyl-1-(4-methoxyphenyl)-1H-pyrazol-5-yl)ureido)-2,3-dimethylphenoxy)pyridin-2-yl)-3-methylurea. $R^t$ 1.89 min (Method 2); m/z 558 (M + H)$^+$ (ES$^+$); $^1$H NMR δ: 1.26 (9H, s), 2.01 (3H, s), 2.12 (3H, s), 2.67 (3H, d), 3.82 (3H, s), 6.32 (1H, s), 6.41 (1H, dd), 6.77 (1H, d), 6.90 (1H, d), 7.08-7.10 (2H, overlapping m), 7.42-7.44 (2H, overlapping m), 7.50 (1H, d), 7.96 (1H, br s), 8.02 (1H, d), 8.33 (1H, s), 8.55 (1H, s), 9.12 (1H, s). |
| 38 | 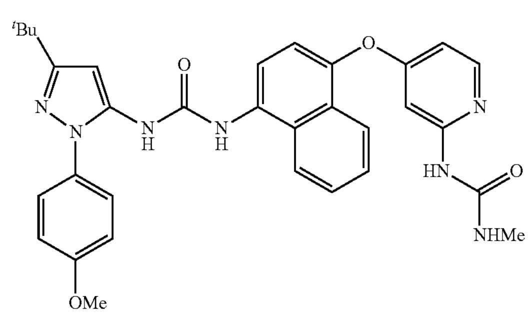 [SMILES: CNC(=O)Nc1cc(Oc2ccc(NC(=O)Nc3cc(C(C)(C)C)nn3-c3ccc(OC)cc3)c3ccccc23)ccn1] | 1-(4-(4-(3-(3-tert-butyl-1-(4-methoxyphenyl)-1H-pyrazol-5-yl)ureido)naphthalen-1-yloxy)pyridin-2-yl)-3-methylurea. $R^t$ 5.15 min (Method 1, basic); m/z 580 (M + H)$^+$ (ES$^+$); $^1$H NMR δ: 1.27 (9H, s), 2.65 (2H, d), 3.83 (3H, s), 6.40 (1H, s), 6.55 (1H, dd), 6.85 (1H, d), 7.12 (2H, m), 7.31 (1H, d), 7.47 (2H, m), 7.58 (1H, m), 7.65 (1H, m), 7.82 (1H, dd), 7.91 (1H, br d), 7.97 (1H, d), 8.04-8.10 (2H, overlapping m), 8.75 (1H, s), 9.10-9.15 (2H, overlapping s). |

TABLE 3-continued

Additional Compound Examples of the Invention

| Ex. No. | Structure | Name and Analytical Data |
|---|---|---|
| 39 | 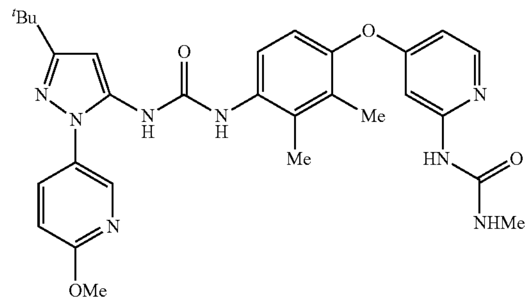 [SMILES: CNC(=O)Nc1cc(Oc2ccc(NC(=O)Nc3cc(C(C)(C)C)nn3-c3ccc(OC)nc3)c(C)c2C)ccn1] | 1-(4-(4-(3-(3-tert-butyl-1-(6-methoxypyridin-3-yl)-1H-pyrazol-5-yl)ureido)-2,3-dimethyl phenoxy)pyridin-2-yl)-3-methylurea. R$^t$ 2.09 min (Method 2); m/z 559 (M + H)$^+$ (ES$^+$); $^1$H NMR δ: 1.27 (9H, s), 2.02 (3H, s), 2.11 (3H, s), 2.67 (3H, d), 3.92 (3H, s), 6.35 (1H, s), 6.41 (1H, dd), 6.78 (1H, d), 6.90 (1H, d), 7.00 (1H, d), 7.47 (1H, d), 7.86 (1H, dd), 7.96 (1H, br s), 8.02 (1H, d), 8.30 (1H, s), 8.33 (1H, d), 8.63 (1H, s), 9.11 (1H, s). |
| 40 | 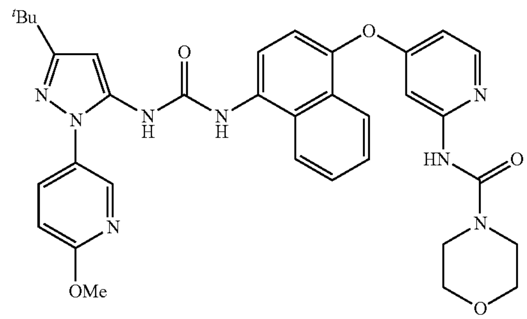 [SMILES: COc1ccc(-n2nc(C(C)(C)C)cc2NC(=O)Nc2ccc(Oc3ccnc(NC(=O)N4CCOCC4)c3)c3ccccc23)cn1] | N-(4-(4-(3-(3-tert-butyl-1-(6-methoxypyridin-3-yl)-1H-pyrazol-5-yl)ureido)naphthalen-1-yloxy)pyridin-2-yl)morpholine-4-carboxamide. R$^t$ 1.82 min (Method 2); m/z 637 (M + H)$^+$ (ES$^+$); $^1$H NMR δ: 1.29 (9H, s), 3.37 (4H, m), 3.53 (4H, m), 3.95 (3H, s), 6.43 (1H, s), 6.62 (1H, dd), 7.03 (1H, d), 7.32 (1H, d), 7.39 (1H, d), 7.58 (1H, m), 7.65 (1H, m), 7.85 (1H, dd), 7.92 (1H, dd), 7.93 (1H, d), 8.07 (1H, d), 8.12 (1H, d), 8.41 (1H, dd), 8.82 (1H, s), 9.09 (1H, s), 9.25 (1H, s). |
| 41 | 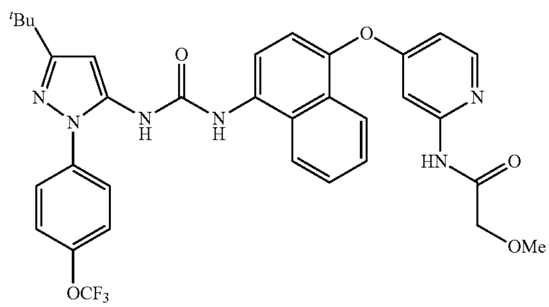 [SMILES: COCC(=O)Nc1cc(Oc2ccc(NC(=O)Nc3cc(C(C)(C)C)nn3-c3ccc(OC(F)(F)F)cc3)c3ccccc23)ccn1] | N-(4-(4-(3-(3-tert-butyl-1-(4-(trifluoromethoxy) phenyl)-1H-pyrazol-5-yl)ureido)naphthalen-1-yloxy)pyridin-2-yl)-2-methoxyacetamide. R$^t$ 2.79 min (Method 2); m/z 649 (M + H)$^+$ (ES$^+$); $^1$H NMR δ: 1.29 (9H, s), 3.30 (3H, s), 3.98 (2H, s), 6.44 (1H, s), 6.70 (1H, dd), 7.34 (1H, d), 7.56-7.60 (3H, overlapping m), 7.64-7.68 (2H, overlapping m), 7.74-7.76 (2H, overlapping m), 7.84 (1H, br d), 7.93 (1H, d), 8.10 (1H, br d), 8.19 (1H, d), 8.90 (1H, s), 9.10 (1H, s), 10.03 (1H, s). |
| 42 | 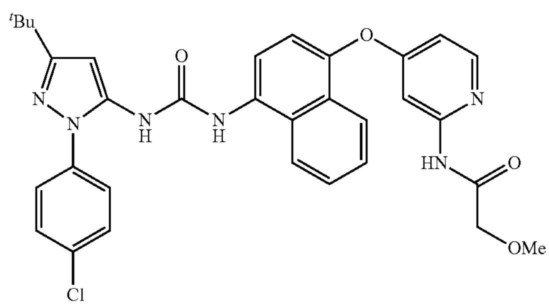 [SMILES: COCC(=O)Nc1cc(Oc2ccc(NC(=O)Nc3cc(C(C)(C)C)nn3-c3ccc(Cl)cc3)c3ccccc23)ccn1] | N-(4-(4-(3-(3-tert-butyl-1-(4-chlorophenyl)-1H-pyrazol-5-yl)ureido)naphthalen-1-yloxy) pyridin-2-yl)-2-methoxyacetamide. R$^t$ 2.64 min (Method 2); m/z 599 (M + H)$^+$ (ES$^+$); $^1$H NMR δ: 1.29 (9H, s), 3.31 (3H, s), 3.99 (2H, s), 6.43 (1H, s), 6.70 (1H, dd), 7.34 (1H, d), 7.58 (1H, m), 7.61-7.68 (6H, overlapping m), 7.84 (1H, d), 7.93 (1H, d), 8.08 (1H, d), 8.19 (1H, d), 8.84 (1H, br s), 9.10 (1H, br s), 10.03 (1H, br s). |
| 43 | 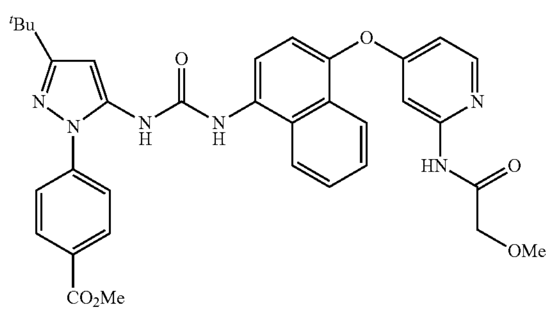 [SMILES: COCC(=O)Nc1cc(Oc2ccc(NC(=O)Nc3cc(C(C)(C)C)nn3-c3ccc(C(=O)OC)cc3)c3ccccc23)ccn1] | methyl 4-(3-tert-butyl-5-(3-(4-((2-(2-methoxy acetamido)pyridin-4-yl)oxy)naphthalen-1-yl) ureido)-1H-pyrazol-1-yl)benzoate. R$^t$ 3.49 min (Method 2); m/z 623 (M + H)$^+$ (ES$^+$); $^1$H NMR δ: 1.25 (9H, s), 3.31 (3H, s), 3.90 (3H, s), 4.00 (2H, s), 6.47 (1H, s), 6.73 (1H, dd), 7.35 (1H, d), 7.56-7.68 (3H, overlapping m), 7.80-7.87 (3H, overlapping m), 7.95 (1H, d), 8.11-8.16 (3H, overlapping m), 8.20 (1H, d), 8.99 (1H, s), 9.15 (1H, s), 10.08 (1H, s). |

TABLE 3-continued

Additional Compound Examples of the Invention

| Ex. No. | Structure | Name and Analytical Data |
|---|---|---|
| 44 | 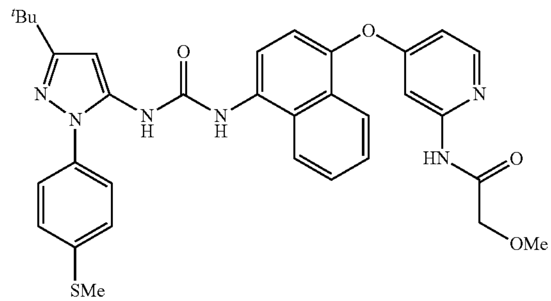 | N-(4-(4-(3-(3-tert-butyl-1-(4-(methylthio)phenyl)-1H-pyrazol-5-yl)ureido)naphthalen-1-yloxy)pyridin-2-yl)-2-methoxyacetamide. $R^t$ 2.55 min (Method 2); m/z 611 (M + H)$^+$ (ES$^+$); $^1$H NMR δ: 1.28 (9H, s), 2.54 (3H, s), 3.30 (3H, s), 3.98 (2H, s), 6.42 (1H, s), 6.70 (1H, dd), 7.34 (1H, d), 7.43-7.46 (2H, overlapping m), 7.52-7.54 (2H, overlapping m), 7.58 (1H, m), 7.64-7.68 (2H, overlapping m), 7.84 (1H, d), 7.97 (1H, d), 8.09 (1H, d), 8.17 (1H, d), 8.83 (1H, s), 9.13 (1H, s), 10.06 (1H, s). |
| 45 | 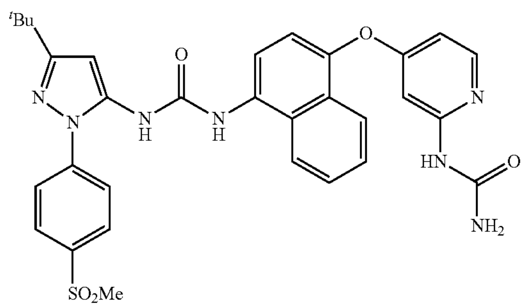 [SMILES: CC(C)(C)c1cc(NC(=O)Nc2ccc(Oc3ccnc(NC(N)=O)c3)c3ccccc23)n(-c2ccc(S(C)(=O)=O)cc2)n1] | 1-(3-tert-butyl-1-(4-(methylsulfonyl)phenyl)-1H-pyrazol-5-yl)-3-(4-((2-ureidopyridin-4-yl)oxy)naphthalen-1-yl)urea. $R^t$ 1.89 min (Method 2); m/z 614 (M + H)$^+$ (ES$^+$); $^1$H NMR δ: 1.31 (9H, s), 3.27 (3H, s), 6.48 (1H, s), 6.58 (1H, br s), 6.85-6.95 (3H, overlapping m), 7.32 (1H, d), 7.58 (1H, m), 7.67 (1H, m), 7.83 (1H, d), 7.89-7.94 (3H, overlapping m), 8.06-8.15 (4H, overlapping m), 9.04 (1H, s), 9.17 (2H, s). |
| 46 | 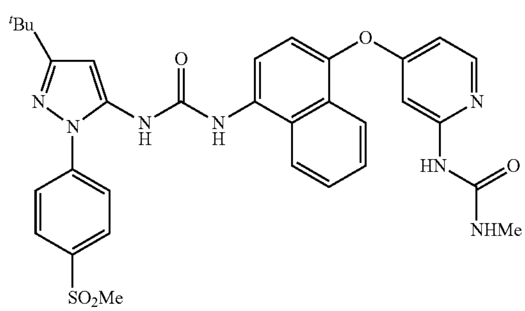 [SMILES: CNC(=O)Nc1cc(Oc2ccc(NC(=O)Nc3cc(C(C)(C)C)nn3-c3ccc(S(C)(=O)=O)cc3)c3ccccc23)ccn1] | 1-(3-tert-butyl-1-(4-(methylsulfonyl)phenyl)-1H-pyrazol-5-yl)-3-(4-((2-(3-methylureido)pyridin-4-yl)oxy)naphthalen-1-yl)urea. $R^t$ 1.98 min (Method 2); m/z 644 (M + H)$^+$ (ES$^+$); $^1$H NMR δ: 1.31 (9H, s), 2.65 (3H, d), 3.27 (3H, s), 6.48 (1H, s), 6.72 (1H, s), 6.87 (1H, s), 7.35 (1H, d), 7.56-7.71 (3H, overlapping m), 7.81 (1H, d), 7.90-7.95 (3H, overlapping m), 8.07-8.13 (3H, overlapping m), 8.17 (1H, d), 9.14 (1H, s), 9.26 (1H, s), 9.54 (1H, br s). |
| 47 | 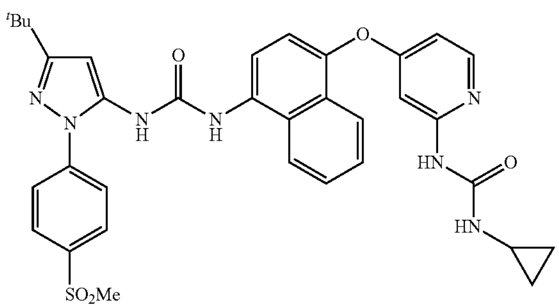 [SMILES: CC(C)(C)c1cc(NC(=O)Nc2ccc(Oc3ccnc(NC(=O)NC4CC4)c3)c3ccccc23)n(-c2ccc(S(C)(=O)=O)cc2)n1] | 1-(3-tert-butyl-1-(4-(methylsulfonyl)phenyl)-1H-pyrazol-5-yl)-3-(4-(2-(3-cyclopropyl ureido)pyridin-4-yloxy)naphthalen-1-yl)urea. $R^t$ 2.35 min (Method 2); m/z 654 (M + H)$^+$ (ES$^+$); $^1$H NMR δ: 0.37 (2H, m), 0.62 (2H, m), 1.30 (9H, s), 2.52 (1H, m), 3.27 (3H, s), 6.48 (1H, s), 6.55-6.58 (1H, dd), 6.98 (1H, s), 7.31 (1H, d), 7.57 (1H, m), 7.67 (1H, m), 7.82 (1H, d), 7.88-7.94 (4H, overlapping m), 8.05 (1H, d), 8.08-8.12 (3H, overlapping m), 8.95 (1H, s), 8.99 (1H, s), 9.12 (1H, s). |

TABLE 3-continued

Additional Compound Examples of the Invention

| Ex. No. | Structure | Name and Analytical Data |
|---|---|---|
| 48 | 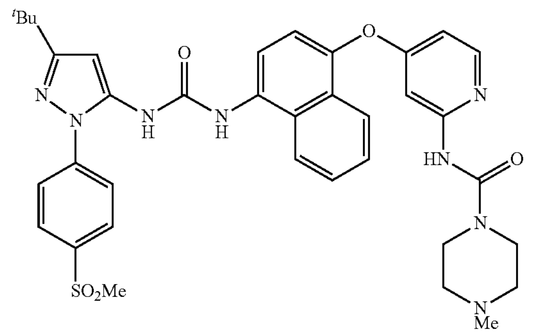 [SMILES: CN1CCN(C(=O)Nc2cc(Oc3ccc(NC(=O)Nc4cc(C(C)(C)C)nn4-c4ccc(S(C)(=O)=O)cc4)c4ccccc34)ccn2)CC1] | N-(4-(4-(3-(3-tert-butyl-1-(4-(methylsulfonyl)phenyl)-1H-pyrazol-5-yl)ureido)naphthalen-1-yloxy)pyridin-2-yl)-4-methylpiperazine-1-carboxamide. $R^t$ 1.87 min (Method 2); m/z 697 (M + H)$^+$ (ES$^+$); $^1$H NMR δ: 1.31 (9H, s), 2.16 (3H, s). 2.24 (4H, m), 3.27 (3H, s), 3.37 (4H, m), 6.48 (1H, s), 6.59 (1H, dd), 7.30 (1H, d), 7.36 (1H, d), 7.57 (1H, m), 7.66 (1H, m), 7.85 (1H, d), 7.90-7.93 (3H, overlapping m), 8.10-8.14 (4H, overlapping m), 9.01 (1H, s), 9.12 (1H, s), 9.18 (1H, s). |
| 49 | 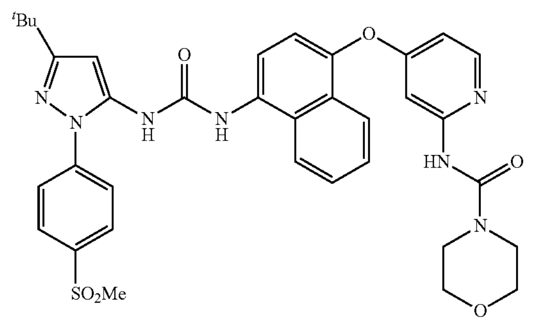 [SMILES: CC(C)(C)c1cc(NC(=O)Nc2ccc(Oc3ccnc(NC(=O)N4CCOCC4)c3)c3ccccc23)n(-c2ccc(S(C)(=O)=O)cc2)n1] | N-(4-(4-(3-(3-tert-butyl-1-(4-(methylsulfonyl)phenyl)-1H-pyrazol-5-yl)ureido)naphthalen-1-yloxy)pyridin-2-yl)morpholine-4-carboxamide. $R^t$ 2.06 min (Method 2); m/z 684 (M + H)$^+$ (ES$^+$); $^1$H NMR δ: 1.31 (9H, s), 3.28 (3H, s), 3.36 (4H, m), 3.50 (4H, m), 6.50 (1H, s), 6.62 (1H, d), 7.30 (1H, d), 7.37 (1H, s), 7.58 (1H, m), 7.67 (1H, m), 7.84 (1H, d), 7.91-7.93 (3H, overlapping m), 8.08-8.12 (4H, overlapping m), 9.00 (1H, s), 9.12 (1H, s), 9.23 (1H, s). |
| 50 | 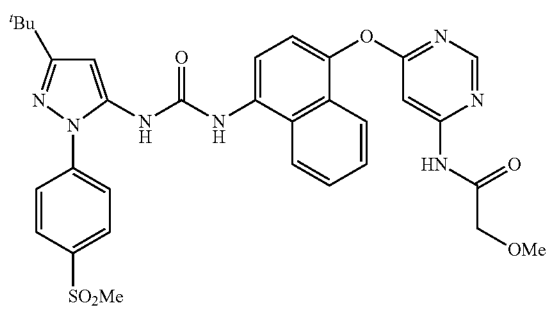 [SMILES: COCC(=O)Nc1cc(Oc2ccc(NC(=O)Nc3cc(C(C)(C)C)nn3-c3ccc(S(C)(=O)=O)cc3)c3ccccc23)ncn1] | N-(6-(4-(3-(3-tert-butyl-1-(4-(methylsulfonyl)phenyl)-1H-pyrazol-5-yl)ureido)naphthalen-1-yloxy)pyrimidin-4-yl)-2-methoxyacetamide. $R^t$ 2.32 min (Method 2); m/z 644 (M + H)$^+$ (ES$^+$); $^1$H NMR δ: 1.30 (9H, s), 3.28 (3H, s), 3.33 (3H, s), 4.09 (2H, s), 6.49 (2H, s), 7.35 (1H, d), 7.55 (1H, m), 7.63 (1H, m), 7.87 (1H, d), 7.86-7.94 (3H, overlapping m), 8.07-8.12 (3H, overlapping m), 8.45 (1H, d), 9.01 (1H, s), 9.12 (1H, s), 10.71 (1H, s). |
| 51 | 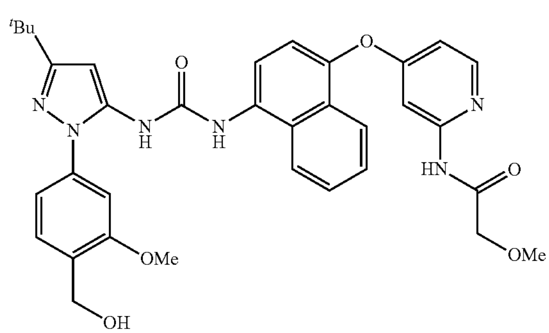 [SMILES: COCC(=O)Nc1cc(Oc2ccc(NC(=O)Nc3cc(C(C)(C)C)nn3-c3ccc(CO)c(OC)c3)c3ccccc23)ccn1] | N-(4-(4-(3-(3-tert-butyl-1-(4-(hydroxymethyl)-3-methoxyphenyl)-1H-pyrazol-5-yl)ureido)naphthalen-1-yloxy)pyridin-2-yl)-2-methoxy acetamide. $R^t$ 1.97 min (Method 2); m/z 625 (M + H)$^+$ (ES$^+$); $^1$H NMR δ: 1.29 (9H, s), 3.30 (3H, s), 3.85 (3H, s), 3.98 (2H, s), 4.55 (2H, s), 5.16 (1H, br s), 6.45 (1H, s), 6.70 (1H, dd), 7.13-7.17 (2H, overlapping m), 7.34 (1H, d), 7.52-7.59 (2H, overlapping m), 7.62-7.67 (2H, overlapping m), 7.83 (1H, d), 7.98 (1H, d), 8.10 (1H, d), 8.18 (1H, d), 8.84 (1H, s), 9.17 (1H, s), 10.05 (1H, s). |

TABLE 3-continued

Additional Compound Examples of the Invention

| Ex. No. | Structure | Name and Analytical Data |
|---|---|---|
| 52 | 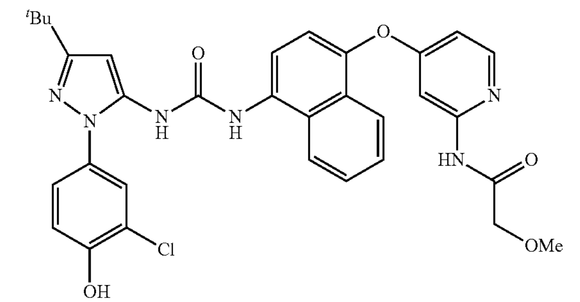 | N-(4-(4-(3-(3-tert-butyl-1-(3-chloro-4-hydroxyphenyl)-1H-pyrazol-5-yl)ureido)naphthalen-1-yloxy)pyridin-2-yl)-2-methoxyacetamide. R$^t$ 4.02 min (Method 1, basic); m/z 615 (M + H)$^+$ (ES$^+$); $^1$H NMR δ: 1.27 (9H, s), 3.30 (3H, s), 3.99 (2H, s), 6.38 (1H, s), 6.69 (1H, dd), 7.12 (1H, d), 7.33-7.36 (2H, overlapping m), 7.54 (1H, d), 7.57 (1H, m), 7.63-7.67 (2H, overlapping m), 7.83 (1H, d), 7.92 (1H, d), 8.05 (1H, d), 8.17 (1H, d), 8.75 (1H, s), 9.11 (1H, s), 10.06 (1H, s), 10.61 (1H, br s). |
| 53 | 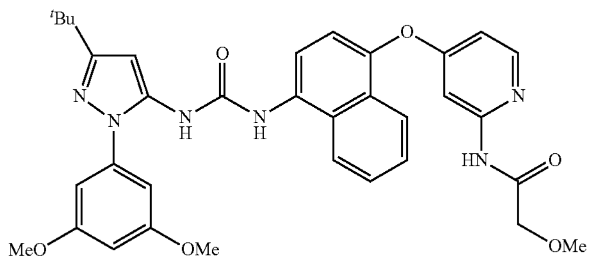 [SMILES: COCC(=O)Nc1cc(Oc2ccc(NC(=O)Nc3cc(C(C)(C)C)nn3-c3cc(OC)cc(OC)c3)c3ccccc23)ccn1] | N-(4-(4-(3-(3-tert-butyl-1-(3,5-dimethoxyphenyl)-1H-pyrazol-5-yl)ureido)naphthalen-1-yloxy)pyridin-2-yl)-2-methoxyacetamide. R$^t$ 5.10 min (Method 1, basic); m/z 625 (M + H)$^+$ (ES$^+$); $^1$H NMR δ: 1.28 (9H, s), 3.30 (3H, s), 3.81 (6H, s), 3.99 (2H, s), 6.43 (1H, s), 6.58 (1H, t), 6.69 (1H, dd), 6.75 (2H, d), 7.34 (1H, d), 7.57 (1H, m), 7.63-7.67 (2H, overlapping m), 7.85 (1H, d), 7.95 (1H, d), 8.11 (1H, d), 8.18 (1H, d), 8.86 (1H, s), 9.19 (1H, s), 10.07 (1H, s). |
| 54 | 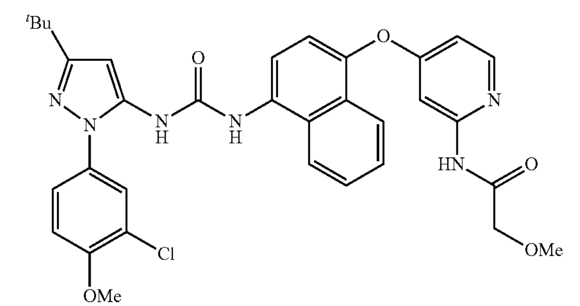 [SMILES: COCC(=O)Nc1cc(Oc2ccc(NC(=O)Nc3cc(C(C)(C)C)nn3-c3ccc(OC)c(Cl)c3)c3ccccc23)ccn1] | N-(4-(4-(3-(3-tert-butyl-1-(3-chloro-4-methoxyphenyl)-1H-pyrazol-5-yl)ureido)naphthalen-1-yloxy)pyridin-2-yl)-2-methoxyacetamide. R$^t$ 4.99 min (Method 1, basic); m/z 629 (M + H)$^+$ (ES$^+$); $^1$H NMR δ: 1.28 (9H, s), 3.30 (3H, s), 3.93 (3H, s), 3.99 (2H, s), 6.40 (1H, s), 6.69 (1H, dd), 7.32-7.35 (2H, overlapping m), 7.53 (1H, m), 7.57 (1H, m), 7.63-7.66 (3H, overlapping m), 7.84 (1H, d), 7.92 (1H, d), 8.05 (1H, d), 8.18 (1H, d), 8.78 (1H, s), 9.10 (1H, s), 10.05 (1H, s). |
| 55 | 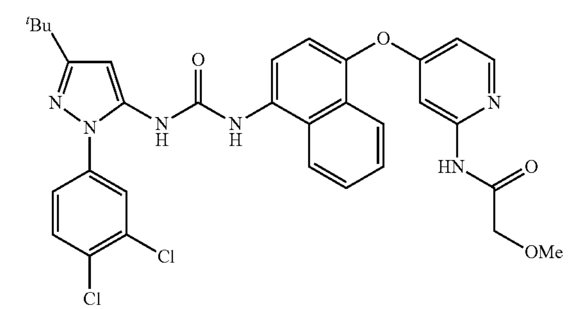 [SMILES: COCC(=O)Nc1cc(Oc2ccc(NC(=O)Nc3cc(C(C)(C)C)nn3-c3ccc(Cl)c(Cl)c3)c3ccccc23)ccn1] | N-(4-(4-(3-(3-tert-butyl-1-(3,4-dichlorophenyl)-1H-pyrazol-5-yl)ureido)naphthalen-1-yloxy)pyridin-2-yl)-2-methoxyacetamide. R$^t$ 2.83 min (Method 2); m/z 633 (M + H)$^+$ (ES$^+$); $^1$H NMR δ: 1.29 (9H, s), 3.31 (3H, s), 3.99 (2H, s), 6.44 (1H, s), 6.70 (1H, dd), 7.34 (1H, d), 7.58 (1H, m), 7.63-7.67 (3H, overlapping m), 7.81-7.87 (3H, overlapping m), 7.91 (1H, d), 8.08 (1H, d), 8.19 (1H, d), 8.87 (1H, br s), 9.10 (1H, br s), 10.03 (1H, br s). |
| 56 | 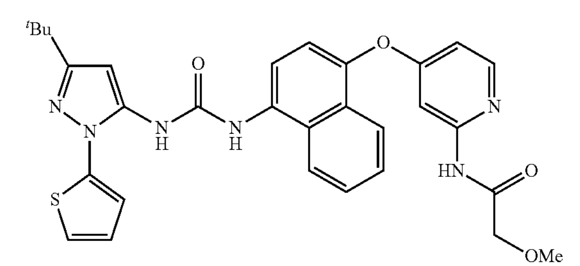 [SMILES: COCC(=O)Nc1cc(Oc2ccc(NC(=O)Nc3cc(C(C)(C)C)nn3-c3cccs3)c3ccccc23)ccn1] | N-(4-(4-(3-(3-tert-butyl-1-(thiophen-2-yl)-1H-pyrazol-5-yl)ureido)naphthalen-1-yloxy)pyridin-2-yl)-2-methoxyacetamide. R$^t$ 2.47 min (Method 2); m/z 571 (M + H)$^+$ (ES$^+$); $^1$H NMR δ: 1.27 (9H, s), 3.30 (3H, s), 3.99 (2H, s), 6.42 (1H, s), 6.71 (1H, dd), 7.14 (1H, dd), 7.28 (1H, dd), 7.35 (1H, d), 7.52 (1H, dd), 7.59 (1H, m), 7.65-7.70 (2H, overlapping m), 7.85 (1H, d), 7.97 (1H, d), 8.15 (1H, d), 8.19 (1H, d), 8.88 (1H, s), 9.27 (1H, s), 10.06 (1H, s). |

TABLE 3-continued

Additional Compound Examples of the Invention

| Ex. No. | Structure | Name and Analytical Data |
|---|---|---|
| 57 | 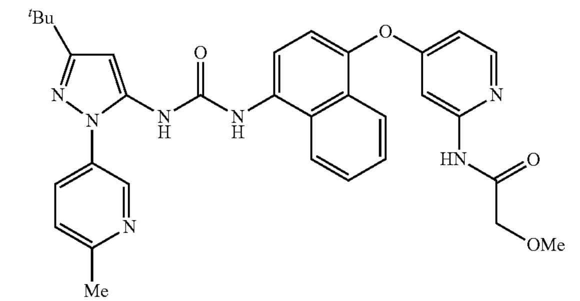 [SMILES: COCC(=O)Nc1cc(Oc2ccc(NC(=O)Nc3cc(C(C)(C)C)nn3-c3ccc(C)nc3)c3ccccc23)ccn1] | N-(4-(4-(3-(3-tert-butyl-1-(6-methylpyridin-3-yl)-1H-pyrazol-5-yl)ureido)naphthalen-1-yloxy)pyridin-2-yl)-2-methoxyacetamide. $R^t$ 2.29 min (Method 2); m/z 580 (M + H)$^+$ (ES$^+$); $^1$H NMR δ: 1.29 (9H, s), 2.57 (3H, s), 3.30 (3H, s), 3.99 (2H, s), 6.45 (1H, s), 6.70 (1H, dd), 7.34 (1H, d), 7.47 (1H, d), 7.58 (1H, m), 7.63-7.68 (2H, overlapping m), 7.84 (1H, br d), 7.89-7.94 (2H, overlapping m), 8.08 (1H, d), 8.18 (1H, d), 8.69 (1H, d), 8.87 (1H, s). 9.10 (1H, s), 10.02 (1H, s). |
| 58 | 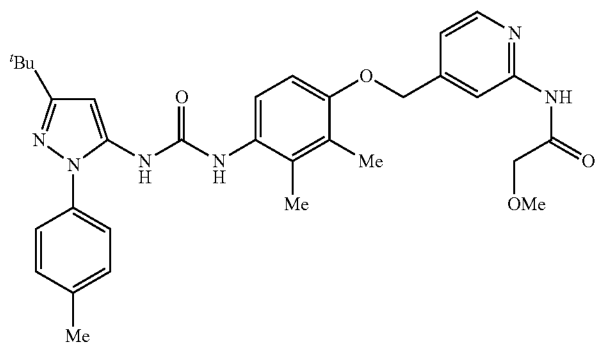 [SMILES: COCC(=O)Nc1cc(COc2ccc(NC(=O)Nc3cc(C(C)(C)C)nn3-c3ccc(C)cc3)c(C)c2C)ccn1] | N-(4-((4-(3-(3-tert-butyl-1-(p-tolyl)-1H-pyrazol-5-yl)ureido)-2,3-dimethylphenoxy)methyl)pyridin-2-yl)-2-methoxyacetamide. $R^t$ 5.12 min (Method 1, basic); m/z 571 (M + H)$^+$ (ES$^+$); $^1$H NMR δ: 1.25 (9H, s), 2.07 (3H, s), 2.20 (3H, s), 2.37 (3H, s), 3.37 (3H, s), 4.07 (2H, s), 5.16 (2H, s), 6.30 (1H, s), 6.80 (1H, d), 7.16-7.19 (2H, overlapping m), 7.31-734 (2H, overlapping m), 7.39-7.41 (2H, overlapping m), 8.14 (1H, s), 8.24 (1H, s), 8.30 (1H, d), 8.40 (1H, s), 10.00 (1H, s). |
| 59 | 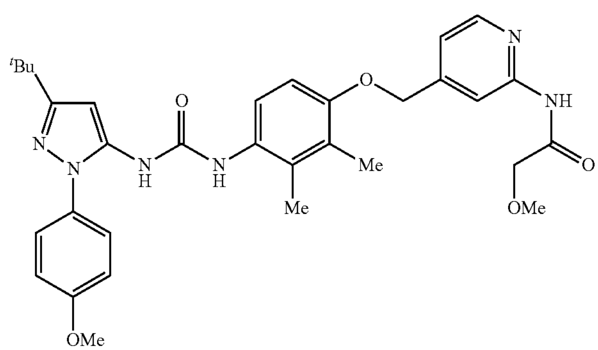 [SMILES: COCC(=O)Nc1cc(COc2ccc(NC(=O)Nc3cc(C(C)(C)C)nn3-c3ccc(OC)cc3)c(C)c2C)ccn1] | N-(4-((4-(3-(3-tert-butyl-1-(4-methoxyphenyl)-1H-pyrazol-5-yl)ureido)-2,3-dimethyl phenoxy)methyl)pyridin-2-yl)-2-methoxy acetamide. $R^t$ 5.00 min (Method 1, basic); m/z 587 (M + H)$^+$ (ES$^+$); $^1$H NMR δ: 1.30 (9H, s), 2.10 (3H, s), 2.25 (3H, s), 3.41 (3H, s), 3.86 (3H, s), 4.11 (2H, s), 5.20 (2H, s), 6.30 (1H, s), 6.86 (1H, d), 7.12 (2H, m), 7.21-7.23 (2H, overlapping m), 7.46 (2H, m), 8.18 (1H, s), 8.28 (1H, s), 8.36 (1H, d), 8.40 (1H, s), 10.06 (1H, s). |
| 60 | 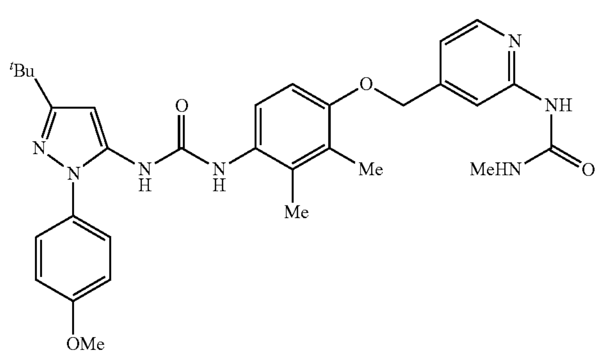 [SMILES: CNC(=O)Nc1cc(COc2ccc(NC(=O)Nc3cc(C(C)(C)C)nn3-c3ccc(OC)cc3)c(C)c2C)ccn1] | 1-(4-((4-(3-(3-tert-butyl-1-(4-methoxyphenyl)-1H-pyrazol-5-yl)ureido)-2,3-dimethylphenoxy)methyl)pyridin-2-yl)-3-methylurea. $R^t$ 5.03 min (Method 1, basic); m/z 572 (M + H)$^+$ (ES$^+$); $^1$H NMR δ: 1.25 (9H, s), 2.07 (3H, s), 2.20 (3H, s), 2.72 (3H, d), 3.31 (3H, s), 5.07 (2H, s), 6.27 (1H, s), 6.78 (1H, d), 6.95 (1H, d), 7.06 (2H, m), 7.18 (1H, d), 7.39-7.44 (3H, overlapping m), 8.12 (1H, s), 8.15 (2H, d), 8.33 (1H, s), 9.31 (1H, s). |

TABLE 3-continued

Additional Compound Examples of the Invention

| Ex. No. | Structure | Name and Analytical Data |
|---|---|---|
| 61 | 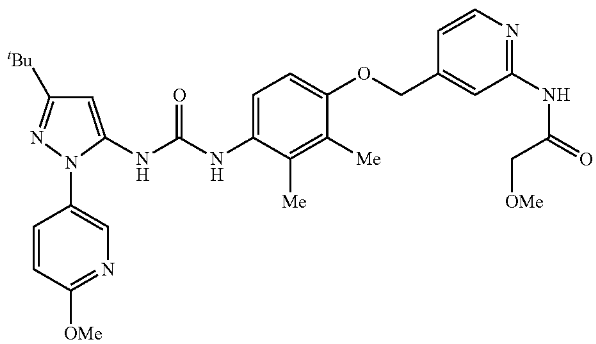 [SMILES: COCC(=O)Nc1cc(COc2ccc(NC(=O)Nc3cc(C(C)(C)C)nn3-c3ccc(OC)nc3)c(C)c2C)ccn1] | N-(4-((4-(3-(3-tert-butyl-1-(6-methoxypyridin-3-yl)-1H-pyrazol-5-yl)ureido)-2,3-dimethyl phenoxy)methyl)pyridin-2-yl)-2-methoxy acetamide. $R^t$ 4.92 min (Method 1, basic); m/z 588 (M + H)⁺ (ES⁺); ¹H NMR δ: 1.25 (9H, s), 2.05 (3H, s), 2.20 (3H, s), 3.36 (3H, s), 3.91 (3H, s), 4.06 (2H, s), 5.16 (2H, s), 6.30 (1H, s), 6.80 (1H, d), 6.98 (1H, d), 7.14-7.17 (2H, overlapping m), 7.83 (1H, d), 8.01 (1H, s), 8.23 (1H, s), 8.29-8.32 (2H, overlapping m), 8.45 (1H, s), 10.00 (1H, s). |
| 62 | 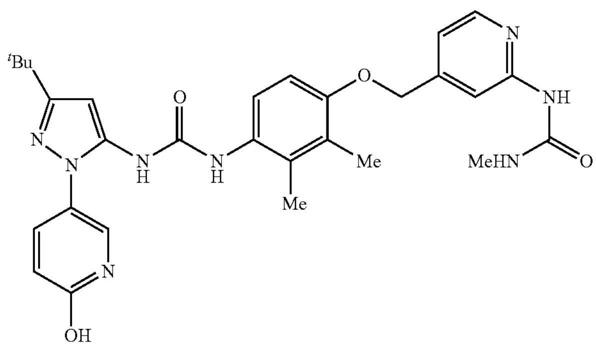 [SMILES: CNC(=O)Nc1cc(COc2ccc(NC(=O)Nc3cc(C(C)(C)C)nn3-c3ccc(O)nc3)c(C)c2C)ccn1] | 1-(4-(4-(3-(3-tert-butyl-1-(6-hydroxypyridin-3-yl)-1H-pyrazol-5-yl)ureido)-2,3-dimethyl phenoxy)pyridin-2-yl)-3-methylurea. $R^t$ 4.60 min (Method 1, basic); m/z 545 (M + H)⁺ (ES⁺); ¹H NMR δ: 1.25 (9H, s), 2.02 (3H, s), 2.13 (3H, s), 2.67 (3H, d), 6.29 (1H, s), 6.42 (1H, dd), 6.46 (1H, br d), 6.78 (1H, d), 6.90 (1H, d), 7.48 (1H, d), 7.54 (1H, dd), 7.68 (1H, br s), 7.96 (1H, br s), 8.02 (1H, d), 8.33 (1H, s), 8.62 (1H, s), 9.13 (1H, s), 11.92 (1H, br s). |
| 63 | 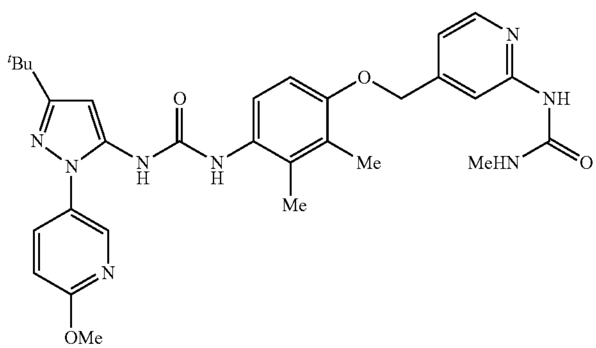 [SMILES: CNC(=O)Nc1cc(COc2ccc(NC(=O)Nc3cc(C(C)(C)C)nn3-c3ccc(OC)nc3)c(C)c2C)ccn1] | 1-(4-((4-(3-(3-tert-butyl-1-(6-methoxypyridin-3-yl)-1H-pyrazol-5-yl)ureido)-2,3-dimethyl phenoxy)methyl)pyridin-2-yl)-3-methylurea. $R^t$ 4.95 min (Method 1, basic); m/z 573 (M + H)⁺ (ES⁺); ¹H NMR δ: 1.25 (9H, s), 2.05 (3H, s), 2.19 (3H, s), 2.72 (3H, d), 3.91 (3H, s), 5.07 (2H, s), 6.30 (1H, s), 6.78 (1H, d), 6.95 (1H, d), 6.97 (1H, d), 7.15 (1H, d), 7.42 (1H, s), 7.83 (1H, d), 8.10 (1H, s), 8.15 (2H, d), 8.31 (1H, d), 8.45 (1H, s), 9.31 (1H, s). |
| 64 | 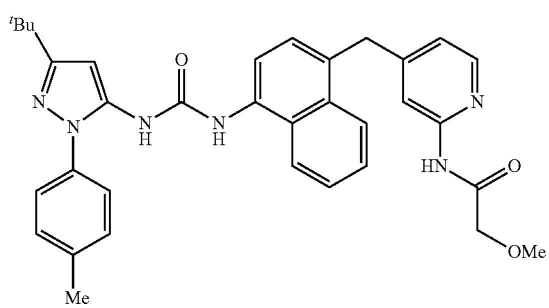 [SMILES: COCC(=O)Nc1cc(Cc2ccc(NC(=O)Nc3cc(C(C)(C)C)nn3-c3ccc(C)cc3)c3ccccc23)ccn1] | N-(4-((4-(3-(3-tert-butyl-1-(p-tolyl)-1H-pyrazol-5-yl)ureido)naphthalen-1-yl)methyl)pyridin-2-yl)-2-methoxyacetamide. $R^t$ 2.50 min (Method 2); m/z 577 (M + H)⁺ (ES⁺); ¹H NMR δ: 1.28 (9H, s), 2.39 (3H, s), 3.33 (3H, s), 4.00 (2H, s), 4.41 (2H, s), 6.40 (1H, s), 6.95 (1H, dd), 7.35-7.37 (2H, overlapping m) 7.42-7.46 (3H, overlapping m), 7.48-7.56 (2H, overlapping m), 7.87 (1H, d), 7.94-7.98 (2H, overlapping m), 8.03 (1H, m), 8.16 (1H, dd), 8.80 (1H, br s), 9.08 (1H, br s), 9.87 (1H, br s). |

TABLE 3-continued

Additional Compound Examples of the Invention

| Ex. No. | Structure | Name and Analytical Data |
|---|---|---|
| 65 | 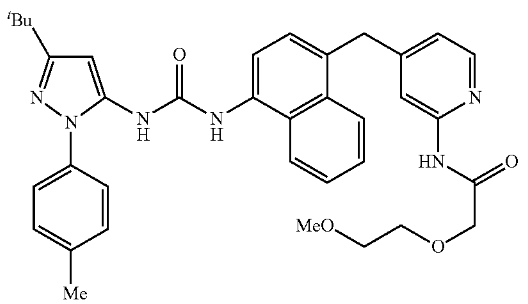 [SMILES: COCCOCC(=O)Nc1cc(Cc2ccc(NC(=O)Nc3cc(C(C)(C)C)nn3-c3ccc(C)cc3)c3ccccc23)ccn1] | N-(4-((4-(3-(3-tert-butyl-1-p-tolyl-1H-pyrazol-5-yl)ureido)naphthalen-1-yl)methyl) pyridin-2-yl)-2-(2-methoxyethoxy)acetamide. $R^t$ 2.50 min (Method 2); m/z 621 (M + H)$^+$ (ES$^+$); $^1$H NMR δ: 1.28 (9H, s), 2.08 (2H, s), 2.39 (3H, s), 3.26 (3H, s), 3.48 (2H, m), 3.63 (2H, m), 4.44 (2H, s), 6.40 (1H, s), 7.01 (1H, dd), 7.37 (2H, d), 7.42-7.46 (3H, overlapping m), 7.53-7.56 (2H, overlapping m), 7.88 (1H, d), 7.93-7.96 (2H, overlapping m), 8.03 (1H, dd), 8.19 (1H, d), 8.78 (1H, br s), 9.07 (1H, br s), 9.94 (1H, br s). |
| 66 | 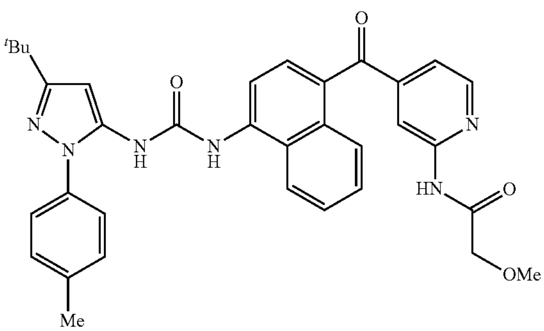 [SMILES: COCC(=O)Nc1cc(C(=O)c2ccc(NC(=O)Nc3cc(C(C)(C)C)nn3-c3ccc(C)cc3)c3ccccc23)ccn1] | N-(4-(4-(3-(3-tert-butyl-1-p-tolyl-1H-pyrazol-5-yl)ureido)-1-naphthoyl)pyridin-2-yl)-2-methoxyacetamide. $R^t$ 2.65 min (Method 2); m/z 591 (M + H)$^+$ (ES$^+$); $^1$H NMR δ: 1.28 (9H, s), 2.39 (3H, s), 3.34 (3H, s), 4.07 (2H, s), 6.45 (1H, s), 7.36-7.39 (3H, overlapping m), 7.45-7.47 (2H, overlapping m), 7.69-7.72 (3H, overlapping m), 8.19-8.23 (2H, overlapping m), 8.35 (1H, br s), 8.50 (1H, m), 8.53 (1H, dd), 9.07 (1H, br s), 9.50 (1H, br s), 10.38 (1H, br s). |
| 67 | 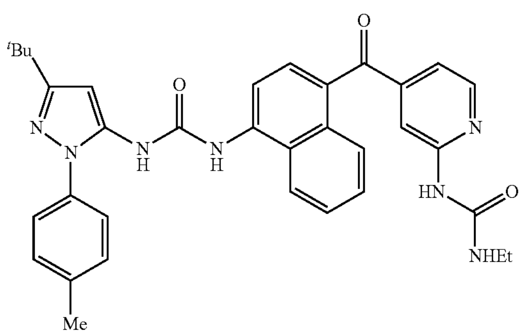 | 1-(3-tert-butyl-1-p-tolyl-1H-pyrazol-5-yl)-3-(4-(2-(3-ethylureido)isonicotinoyl)naphthalen-1-yl)urea. $R^t$ 2.64 min (Method 2); m/z 590 (M + H)$^+$ (ES$^+$); $^1$H NMR δ: 1.07 (3H, t), 1.29 (9H, s), 2.39 (3H, s), 3.16 (2H, m), 6.45 (1H, s), 7.16 (1H, dd), 7.38 (2H, d), 7.46 (2H, d), 7.66-7.76 (5H, overlapping m), 8.19-8.21 (2H, overlapping m), 8.38 (1H, d), 8.46 (1H, m), 9.04 (1H, brs), 9.33 (1H, br s), 9.47 (1H, br s). |

Biological Screening: Experimental Methods

Enzyme Inhibition Assay

The enzyme inhibitory activities of compounds disclosed herein were determined by fluorescence resonance energy transfer (FRET) using synthetic peptides labelled with both donor and acceptor fluorophores (Z-LYTE, Invitrogen Ltd., Paisley, UK). Recombinant, phosphorylated p38 MAPKγ (MAPK12:Invitrogen) was diluted in HEPES buffer, mixed with the test compound at the desired final concentrations and incubated for 2 hr at RT. The FRET peptide (2 μM) and ATP (100 μM) were added to the enzyme/compound mixture and incubated for 1 hr. Development reagent (protease) was added for 1 hr prior to detection in a fluorescence microplate reader (Varioskan® Flash, ThermoFisher Scientific). The site-specific protease cleaves non-phosphorylated peptide only and eliminates the FRET signal. Phosphorylation levels of each reaction were calculated using the ratio of coumarin emission (donor) over fluorescein emission (acceptor) for which high ratios indicate high phosphorylation and low ratios indicate low phosphorylation levels. The percentage inhibition of each reaction was calculated relative to non-inhibited control and the 50% inhibitory concentration (IC$_{50}$ value) then calculated from the concentration-response curve.

For the p38 MAPKα isoform (MAPK14: Invitrogen), enzyme activity was evaluated indirectly by determining the level of activation/phosphorylation of the down-stream molecule, MAPKAP-K2. The p38 MAPKα protein was mixed with the test compound for 2 hr at RT. The p38a inactive target MAPKAP-K2 (Invitrogen) and FRET peptide (2.0 μM), which is a phosphorylation target for MAPKAP-K2, and ATP (10.0 μM) were added to the enzymes/compound mixture and the resulting mixture incubated for 1 hr. Development reagent was then added and the mixture incubated for 1 hr before detection by fluorescence completed the assay protocol.

Cellular Potency Assays:

Cellular Potency as Determined by LPS-Induced TNFα/IL-8 Release in d-U937Cells

U937 cells, a human monocytic cell line, were differentiated to macrophage-type cells by incubation with phorbol myristate acetate (PMA; 100 ng/mL) for 48 to 72 hr. Cells were pre-incubated with final concentrations of test compound for 2 hr and were then stimulated with 0.1 μg/mL of LPS (from *E. Coli*: O111:B4, Sigma) for 4 hr. The supernatant was collected for determination of TNFα and IL-8 concentrations by sandwich ELISA (Duo-set, R&D systems). The inhibition of TNFα production was calculated as a percentage of that achieved by 10 μg/mL of BIRB796 at each concentration of test compound by comparison against vehicle control. The relative 50% effective concentration ($REC_{50}$) was determined from the resultant concentration-response curve. The inhibition of IL-8 production was calculated at each concentration of test compound by comparison with vehicle control. The 50% inhibitory concentration ($IC_{50}$) was determined from the resultant concentration-response curve.

Cellular Potency as Determined by LPS-Induced TNFα Release in THP-1 Cells

THP-1 cells, a human monocytic cell line, were stimulated with 3 μg/mL of LPS (from *E. Coli*; O111:B4, Sigma) for 4 hr and the supernatant collected for determination of the TNFα concentration by sandwich ELISA (Duo-set, R&D systems). The inhibition of TNFα production was calculated at each concentration by comparison with vehicle control. The 50% inhibitory concentration ($IC_{50}$) was determined from the resultant concentration-response curve.

Cellular Potency as Determined by Poly I:C-Induced ICAM-1 Induction in BEAS2B Cells Poly I:C (1 μg/mL) (Invivogen Ltd., San Diego, Calif.) was transfected into BEAS2B cells (human bronchial epithelial cells, ATCC) with Oligofectamine (Invitrogen, Carlsbad, Calif.). Cells were pre-incubated with final concentrations of test compounds for 2 hr and the level of ICAM1 expression on the cell surface was determined by cell-based ELISA. At a time point 18 hr after poly I:C transfection, cells were fixed with 4% formaldehyde in PBS and then endogenous peroxidase was quenched by the addition of 0.1% sodium azide and 1% hydrogen peroxide. Cells were washed with wash-buffer (0.1% Tween in PBS: PBS-Tween). and after blocking the wells with 5% milk in PBS-Tween for 1 hr, the cells were incubated with anti-human ICAM-1 antibody (Cell Signaling Technology, Danvers, Mass.) in 1% BSA PBS overnight at 4° C. The cells were washed with PBS-Tween and incubated with the secondary antibody (HRP-conjugated anti-rabbit IgG, Dako Ltd., Glostrup, Denmark). The ICAM-1 signal was detected by adding substrate and reading the absorbance at 450 nm against a reference wavelength of 655 nm using a spectrophotometer. The cells were then washed with PBS-Tween and total cell numbers in each well were determined by reading absorbance at 595 nm after Crystal Violet staining and elution by 1% SDS solution. The measured OD 450-655 readings were corrected for cell number by dividing with the OD595 reading in each well. The inhibition of ICAM-1 expression was calculated at each concentration of test compound by comparison with vehicle control. The 50% inhibitory concentration ($IC_{50}$) was determined from the resultant concentration-response curve.

MTT Assay: Determination of Cell Viability on Exposure to Test Compounds

Differentiated U937 cells were pre-incubated with each test compound under two protocols: the first for 4 hr in 5% FCS and the second in 10% FCS for 24 h. The supernatant was replaced with 200 μL of new media and 10 μL of MTT stock solution (5 mg/mL) was added to each well. After incubation for 1 hr the media were removed, 200 μL of DMSO was added to each well and the plates were shaken lightly for 1 hr prior to reading the absorbance at 550 nm. The percentage loss of cell viability was calculated for each well relative to vehicle (0.5% DMSO) treatment. Consequently an apparent increase in cell viability for drug treatment relative to vehicle is tabulated as a negative percentage.

LPS-Induced Neutrophil Accumulation in Mice

Non-fasted Balb/c mice were dosed by the intra tracheal route with either vehicle, or the test substance at the indicated times (within the range 2-12 hr) before stimulation of the inflammatory response by application of an LPS challenge. At T=0, mice were placed into an exposure chamber and exposed to LPS. After a further 8 hr the animals were anesthetized, their tracheas cannulated and BALF extracted by infusing and then withdrawing from their lungs 1.0 mL of PBS via the tracheal catheter. Total and differential white cell counts in the BALF samples were measured using a Neubaur haemocytometer. Cytospin smears of the BALF samples were prepared by centrifugation at 200 rpm for 5 min at RT and stained using a DiffQuik stain system (Dade Behring). Cells were counted using oil immersion microscopy.

Biological Screening Results

In Vitro Assays

The in vitro profiles of the compound examples disclosed herein, as determined using the protocols described above, are presented below (Table 4).

TABLE 4

In Vitro Profiles of Compound Examples.

| | Enzyme Inhibition | | LPS/TNFα | | LPS/IL-8 | PolyI:C/ICAM1 | MTT Assay[a] (Viability) | |
|---|---|---|---|---|---|---|---|---|
| | $IC_{50}$ | | $IC_{50}$ | $REC_{50}$ | $IC_{50}$ | | 4 h | 24 h |
| Example No | p38α | p38γ | THP-1 | d-U937 | d-U937 | BEAS2B | d-U937 | |
| 1 | 0.9 | 72.4 | 1.0 | 0.6 | 1.0 | 8.3 | −26.6 | 78.0 |
| 2 | 13.0 | 42.3 | 1.3 | 0.4 | 7.2 | 4.1 | −13.2 | 15.1 |
| 3 | 15.5 | 58.2 | 1.5 | 1.9 | 3.3 | 5.7 | −28.4 | −51.5 |
| 4 | 4.6 | 149.6 | 1.3 | 0.04 | 3.0 | 4.0 | −3.9 | −38.2 |
| 5 | 1.7 | 88.9 | 0.4 | 0.66 | 0.7 | 6.7 | 4.5 | −19.9 |
| 6 | 17.8 | 51.3 | 1.2 | 19.4 | 2.6 | 1.0 | −10.7 | −50.1 |
| 7 | 4.1 | 138.0 | 0.7 | 0.03 | 0.1 | 1.9 | −13.3 | −39.1 |
| 8 | 16.6 | 227.5 | 1.6 | 0.6 | 1.2 | 1.4 | −20.1 | −77.9 |
| 9 | 2.7 | 202.9 | 0.5 | 0.6 | 1.4 | 2.1 | −5.7 | 18.6 |
| 10 | 4.7 | 104.1 | 1.6 | 1.5 | 2.3 | 3.5 | −12.5 | −21.2 |
| 11 | 4.0 | 150.9 | 0.6 | 0.2 | 3.6 | 2.5 | −9.3 | −0.8 |
| 12 | 2.7 | 146.9 | 3.3 | 0.4 | 8.4 | 3.2 | −6.2 | −42.9 |
| 13 | 10.7 | 168.5 | 1.3 | 0.03 | 8.6 | 2.3 | −28.5 | 27.0 |

TABLE 4-continued

In Vitro Profiles of Compound Examples.

| | Enzyme Inhibition | | LPS/TNFα | | LPS/IL-8 | Polyl:C/ICAM1 | MTT Assay[a] (Viability) | |
|---|---|---|---|---|---|---|---|---|
| | $IC_{50}$ | | $IC_{50}$ | $REC_{50}$ | $IC_{50}$ | | 4 h | 24 h |
| Example No | p38α | p38γ | THP-1 | d-U937 | d-U937 | BEAS2B | d-U937 | |
| 14 | 17.0 | 399.6 | 3.2 | 0.6 | 7.3 | 1.9 | −0.4 | −50.0 |
| 15 | 23.6 | 81.5 | 1.5 | 1.6 | 2.4 | 16.3 | −15.4 | −66.2 |
| 16 | 4.5 | 54.3 | 1.2 | 1.2 | 29.6 | 8.1 | −16.7 | −6.2 |
| 17 | 14.3 | 76.3 | 2.0 | 1.4 | 24.5 | 25.3 | −6.1 | −7.6 |
| 18 | 8.8 | 95.5 | 1.2 | 0.7 | 40.0 | 3.7 | 8.2 | −2.9 |
| 19 | 0.4 | 260.5 | 1.8 | 8.1 | 24.5 | 368.7 | −1.7 | −11.7 |
| 20 | 3.6 | 142.8 | 0.9 | 0.2 | 0.6 | 4.4 | −32.6 | −9.0 |
| 21 | 26.0 | 340.7 | 2.5 | 6.6 | 30.3 | 6.3 | 2.7 | 5.3 |
| 22 | 14.0 | 7030 | 53.6 | 3.0 | 651.4 | 571.7 | 21.1[b] | 80.8[b] |
| 23 | 20.3 | 3012. | 12.4 | 3.4 | 21.4 | 20.3 | 15.2[b] | −1.7[b] |
| 24 | 1.5 | 1337 | 11.8 | 3.3 | 35.6 | 110.4 | −10.8 | −7.4 |
| 25 | 3.4 | 3010 | 0.9 | 0.5 | 0.7 | 21.8 | −7.6 | 4.7 |
| 26 | 48.2 | 779.1 | 3.5 | 0.4 | 1.0 | 4.4 | −27.9 | −33.2 |
| 27 | 74.3 | 1967 | 15.2 | 18.8 | 3519 | 283.9 | −4.6 | −23.9 |
| 28 | 1.4 | 9298 | 41.3 | 7.1 | 62.7 | 1578 | −23.7 | −34.5 |
| 29 | 7.7 | 14544 | 138.4 | 3304 | >1692 | 412.2 | 0.8 | −5.7 |
| 30 | 10.1 | >15601 | 10.2 | 107.6 | 1910 | 1494 | −6.3 | −46.1 |
| 31 | 17.1 | 77.2 | 1.0 | 0.8 | 19.6 | >149 | 1.7 | 50.1 |
| 32 | 7.7 | 78.4 | 0.7 | 0.1 | 0.7 | 5.5 | 5.8 | 42.2 |
| 33 | 5.3 | 179.8 | 1.0 | 0.7 | 7.0 | 4.4 | −1.3 | −24.1 |
| 34 | 2.0 | 89.3 | 1.5 | 1.0 | 1.9 | 4.4 | −25.8 | −43.4 |
| 35 | 11.3 | 324.2 | 1.6 | 0.6 | 1.9 | 2.1 | −15.4 | −41.3 |
| 36 | 15.1 | 153.0 | 0.8 | 0.1 | 0.8 | 4.9 | −5.2 | −1.6 |
| 37 | 29.1 | 116.7 | 1.5 | 1.4 | 18.1 | 2.6 | 5.3 | 42.7 |
| 38 | 15.7 | 122.3 | 1.7 | 18.4 | 21.8 | 9.8 | −1.7 | −38.2 |
| 39 | 30.7 | 81.8 | 1.8 | 1.8 | 23.2 | 2.9 | −12.6 | 21.6 |
| 40 | 15.6 | 113.4 | 1.5 | 0.9 | 6.2 | 4.8 | −12.1 | −12.0 |
| 41 | 26.1 | 875.3 | 7.6 | 15.2 | 10.4 | 21.4 | −26.2 | 1.3 |
| 42 | 25.0 | 238.9 | 2.8 | 7.2 | 18.9 | 22.2 | −10.7 | −24.9 |
| 43 | 8.3 | 192.3 | 2.0 | 1.6 | 8.9 | 1.7 | −12.8 | 0.1 |
| 44 | 15.1 | 194.2 | 1.2 | 0.1 | 5.9 | 7.5 | −4.0 | −16.4 |
| 45 | 18.9 | 48.7 | 2.2 | 0.3 | 0.5 | 30.9 | −14.4 | 13.9 |
| 46 | 36.2 | 104.3 | 2.3 | 0.4 | 2.0 | 41.2 | −12.6 | −47.9 |
| 47 | 8.4 | 262.2 | 17.3 | 17.0 | 24.3 | 2.4 | 3.5 | −21.7 |
| 48 | 0.6 | 123.1 | 3.4 | 2.4 | 5.0 | 32.7 | −16.1 | −11.3 |
| 49 | 5.2 | 184.7 | 0.8 | 0.5 | 0.8 | 10.7 | −15.9 | 11.8 |
| 50 | 9.5 | 39.3 | 13.3 | 4.5 | 272.3 | 100.4 | −8.0 | −10.4 |
| 51 | 11.9 | 149.3 | 1.6 | 0.9 | 38.7 | 2.5 | −5.2 | 61.0 |
| 52 | 1.9 | 332.3 | 8.2 | 16.3 | >1626 | 5.7 | 8.5 | −48.8 |
| 53 | 29.9 | 83.4 | 1.2 | 0.4 | 20.0 | 27.4 | 3.1 | −0.9 |
| 54 | 9.1 | 199.2 | 1.3 | 0.2 | 2.7 | 0.7 | 0.1 | −7.5 |
| 55 | 14.9 | 101.7 | 4.3 | 0.8 | 5.5 | 14.7 | −16.1 | −71.1 |
| 56 | 6.6 | 55.0 | 0.6 | 0.0 | 0.5 | 13.4 | 4.8 | 43.1 |
| 57 | <0.2 | 246.3 | 1.6 | 0.3 | 17.2 | 8.6 | −3.4 | 76.0 |
| 58 | 10.6 | 329.2 | 387.7 | 10.4 | 45.6 | 474.4 | −2.8 | 12.0 |
| 59 | 12.7 | 4148 | 241.5 | 104.5 | 164.6 | 277.3 | 11.3 | 0.9 |
| 60 | 13.0 | >17483 | 122.4 | 24.3 | 363.6 | >175 | 17.2 | −0.2 |
| 61 | 12.8 | 2814 | 1257 | 119.6 | 203.7 | >1702 | 3.5 | −5.1 |
| 62 | 14.8 | 20.3 | 2.6 | 2.5 | 14.4 | 24.6 | −1.1 | −2.6 |
| 63 | 16.2 | >17452 | 28.3 | 26.3 | 124.7 | 178.3 | 32.5 | 21.2 |
| 64 | 17.1 | 1648 | 10.9 | 2.1 | 7.4 | 20.1 | −3.7[b] | 61.6[b] |
| 65 | 1.2 | 274.7 | 10.7 | 10.9 | 18.9 | 62.7 | −1.5[b] | 55.9[b] |
| 66 | 7.3 | 7359 | 2.9 | 1.0 | 170.7 | 48.4 | 11.0[b] | 71.1[b] |
| 67 | 18.8 | 442.9 | 6.5 | 17.6 | 21.9 | 13.8 | −9.9[b] | 8.8[b] |

[a]MTT assay was conducted at 1 μg/mL except were indicated otherwise;
[b]assay performed at 10 μg/mL.

In Vivo Assays:

The ability of selected compound examples disclosed herein, to inhibit LPS-induced neutrophil accumulation in the lungs of mice, using the screening protocol described above, are presented below (Tables 5-7). Treatment of mice with compound Example 67 was found to produce a marked and long-lasting inhibition of neutrophil accumulation into the BALF when administered 2 and 12 hr prior to LPS challenge (Table 5).

TABLE 5

The effects of treatment with compound Example 67 on LPS-induced airway neutrophilia in mice.

| Treatment with Compound | Neutrophil numbers in BAL × $10^5$/ml (% inhibition) | |
|---|---|---|
| Example (0.2 mg/mL) | 2 hr pre-dose | 12 h pre-dose |
| Vehicle | 17.6 ± 2.4 | — |
| 67 | 10.5 ± 1.5 (40) | 14.2 ± 1.7 (20) |

Furthermore, treatment of mice with each of the following compound Examples: 13, 16, 34, or 45 produced inhibitory effects versus neutrophil accumulation into the BALF when the test substances were dosed 8 hr prior to LPS challenge (Tables 6 and 7). The inhibitory effects of treatment with either compound Example 13 (Table 6) or compound Example 16 (Table 7) were particularly marked.

TABLE 6

The effects of treatment with compound Examples 45 and 13 on LPS-induced airway neutrophilia in mice.

| Treatment with Compound Example (0.2 mg/mL) | Neutrophil numbers in BAL × $10^5$/mL 8 h pre-dose | % inhibition of Influx |
|---|---|---|
| Vehicle | 17.3 ± 2.7 | — |
| 45 | 13.2 ± 2.2 | 24 |
| 13 | 9.9 ± 1.2 | 43 |

TABLE 7

The effects of treatment with compound Examples 34 and 16 on LPS-induced airway neutrophilia in mice.

| Treatment with Compound Example (0.2 mg/mL) | Neutrophil numbers in BAL × $10^5$/mL 8 h pre-dose | % inhibition of Influx |
|---|---|---|
| Vehicle | 14.0 ± 2.33 | — |
| 34 | 12.0 ± 1.7 | 14 |
| 16 | 6.3 ± 1.2 | 55 |

The invention claimed is:

1. A compound of formula (I):

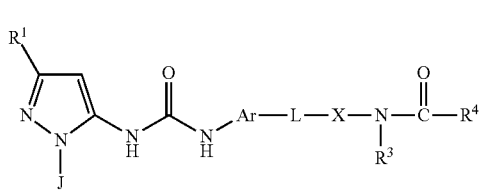

(I)

wherein:
J represents

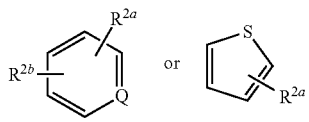

Ar is a naphthylene ring which may be optionally substituted by one or more groups independently selected from $C_{1-6}$ alkyl, $C_{1-6}$ alkoxy, amino, $C_{1-4}$ mono alkyl amino and $C_{2-8}$ di-alkyl amino;

Q is N, or CH;

$R^1$ is H,
  phenyl, or
  a saturated or unsaturated branched or unbranched $C_{1-10}$ alkyl in the form of an acyclic or alicyclic chain wherein one or more carbons in the chain are optionally replaced by a heteroatom(s) independently selected from —O—, —N— and $S(O)_n$ and the chain is optionally substituted by:
    one oxo group, and/or
    one or more halogen atoms;

$R^{2a}$ is H, halo, or a saturated or unsaturated branched or unbranched $C_{1-8}$ alkyl chain, wherein one or more carbons are optionally replaced by a heteroatom(s) independently selected from —O—, —N— and/or $S(O)_m$ and the chain is optionally substituted by one or more halogen atoms;

$R^{2b}$ is H, halo, $C_{1-6}$ alkoxy or $C_{1-6}$ alkyl optionally substituted by OH;

L is a saturated or unsaturated branched or unbranched $C_{1-6}$ alkyl chain, wherein one or more carbons are optionally replaced by a heteroatom selected from —O— and/or S, and the chain is optionally substituted by one or two oxo groups;

X is a pyridine or pyrimidine ring optionally substituted by $C_{1-3}$ alkyl, or $C_{1-3}$ haloalkyl;

$R^3$ is H;

$R^4$ is selected from:
a) a saturated or unsaturated, branched or unbranched $C_{1-10}$ alkyl chain, wherein optionally at least one carbon is replaced by a heteroatom independently selected from O, N, $S(O)_p$, wherein said chain is optionally, substituted by one or more groups independently selected from oxo, halogen, a $C_{6-10}$ aryl group, a 5 or 6 membered heteroaryl group, a 5 or 6 membered heterocyclyl group or a $C_{3-8}$ cycloalkyl group,
  each aryl, heteroaryl, heterocyclyl or cycloalkyl group bearing 0 to 3 substituents selected from halogen, hydroxyl, $C_{1-6}$ alkyl, $C_{1-6}$ alkoxy, $C_{1-6}$ haloalkyl, amino, $C_{1-4}$ mono or $C_{2-8}$ di-alkyl amino, $C_{1-4}$ mono or $C_{2-8}$ di-acyl amino, $S(O)_q C_{1-6}$ alkyl, $C_{0-6}$ alkylC(O)$C_{1-6}$ alkyl or $C_{0-6}$ alkylC(O)NC$_{0-6}$ alkyl $C_{0-6}$ alkyl, $C_{0-6}$ alkylC(O)$C_{1-6}$ heteroalkyl,
  with the proviso that the atom linked directly to the carbonyl in —NR$^3$C(O)— is not an oxygen or a sulfur atom; and
b) a $C_{0-8}$ alkyl-heterocycle wherein the heterocyclyl group has 5 or 6 members and comprises at least one heteroatom selected from O, N, and S, and said heterocycle is optionally substituted by one, two or three groups independently selected from halogen, hydroxyl, $C_{1-6}$ alkyl, $C_{1-6}$ alkoxy, $C_{1-6}$ haloalkyl, amino, $C_{1-4}$ mono and $C_{2-8}$ di-alkyl amino, $C_{1-4}$ mono or $C_{2-8}$ di-acyl amino, $S(O)_q C_{1-6}$ alkyl, $C_{0-6}$ alkylC(O)$C_{1-6}$ alkyl, $C_{0-6}$ alkylC(O)NC$_{0-6}$ alkyl $C_{0-6}$ alkyl or $C_{0-6}$ alkylC(O)$C_{0-6}$ heteroalkyl;

n is 0, 1 or 2;
m is 0, 1 or 2;
p is 0, 1 or 2;
q is 0, 1 or 2;
or a pharmaceutically acceptable salt thereof, including all stereoisomers, tautomers and isotopic derivatives thereof with the proviso that when:

L represents a saturated or unsaturated branched or unbranched $C_{1-6}$ alkyl-chain wherein one or more carbons are optionally replaced by —O— and the chain is optionally substituted by one or more halogen atoms, and $R^1$ is $C_{1-6}$ alkyl optionally substituted by a hydroxyl group, and J represents:

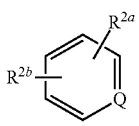

wherein Q is CH, and
$R^{2a}$ is hydrogen, then
$R^{2b}$ does not represent H or $C_{1-6}$ alkyl optionally substituted by a hydroxyl group.

2. A compound of formula (I) according to claim 1, wherein $R^1$ is —$C_{1-6}$ alkyl optionally substituted by OH, $C_{3-10}$ cycloalkyl, $C_{3-10}$ heterocycloalkyl, $C_{1-6}$ haloalkyl or $C_{1-6}$ alkylOC(O)CH$_3$.

3. A compound of formula (I) according to claim 1, wherein $R^1$ is methyl, ethyl, propyl, iso-propyl, butyl or tert-butyl.

4. A compound of formula (I) according to claim 1, wherein $R^1$ is —C(CH$_3$)$_2$CH$_2$OH.

5. A compound of formula (I) according to claim 1, wherein $R^1$ is cyclopropyl, 1-methylcyclopropyl, cyclopentyl, cyclohexyl, 1-methylcyclohexyl, or adamantyl.

6. A compound of formula (I) according to claim 1, wherein $R^1$ is tetrahydropyranyl or 4-methyltetrahydro-2H-pyran-4-yl.

7. A compound of formula (I) according to claim 1, wherein $R^1$ is —CF$_3$, —CF$_2$CF$_3$ or —CCl$_3$.

8. A compound of formula (I) according to claim 1, wherein $R^1$ is phenyl.

9. A compound of formula (I) according to claim 1, wherein $R^{2a}$ in

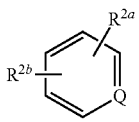

is in the 3, or 4 position.

10. A compound of formula (I) according to claim 1, wherein $R^{2a}$ is methyl, ethyl, n-propyl, iso-propyl, n-butyl or tert-butyl.

11. A compound of formula (I) according to claim 1, wherein $R^{2a}$ is —OH.

12. A compound of formula (I) according to claim 1, wherein $R^{2a}$ is halo.

13. A compound of formula (I) according to claim 1, wherein $R^{2a}$ is selected from —$C_{1-6}$ alkyl substituted by a hydroxyl group, $C_{1-6}$ alkoxy, —S$C_{1-6}$ alkyl, —SO$_2C_{1-6}$ alkyl or —OCF$_3$.

14. A compound of formula (I) according to claim 1, wherein $R^{2a}$ is —NR'R" wherein R' is H, —$C_{1-3}$ alkyl or —SO$_2C_{1-3}$alkyl, and R" is H or —$C_{1-3}$.

15. A compound of formula (I) according to claim 1, wherein $R^{2a}$ is —NHSO$_2$CH$_3$.

16. A compound of formula (I) according to claim 1, wherein $R^{2b}$ is selected from H or halo.

17. A compound of formula (I) according to claim 1, wherein $R^{2a}$ is chloro and $R^{2b}$ is chloro.

18. A compound of formula (I) according to claim 1, wherein $R^{2a}$ is chloro and $R^{2b}$ is —OCH$_3$.

19. A compound of formula (I) according to claim 1, wherein $R^{2a}$ is —OCH$_3$ and $R^{2b}$ is —OCH$_3$.

20. A compound of formula (I) according to claim 1, wherein $R^{2a}$ chloro is and $R^{2b}$ is —OH.

21. A compound of formula (I) according to claim 1, wherein Ar is 1,4 naphthyl.

22. A compound of formula (I) according to claim 1, wherein L is selected from O, —OCH$_2$— or —OCH$_2$CH$_2$—.

23. A compound of formula (I) according to claim 1, wherein X is pyridine.

24. A compound of formula (I) according to claim 1, wherein $R^4$ is selected from:

a) a saturated or unsaturated, branched or unbranched $C_{1-10}$ alkyl chain, wherein at least one carbon is replaced by a heteroatom independently selected from O, N, S(O)$_p$, wherein said chain is optionally, substituted by one or more groups independently selected from oxo, halogen, a $C_{6-10}$ aryl group, a 5 or 6 membered heteroaryl group, a 5 or 6 membered heterocyclyl group or a $C_{3-8}$ cycloalkyl group, each aryl, heteroaryl, heterocyclyl or cycloalkyl group bearing 0 to 3 substituents selected from halogen, hydroxyl, $C_{1-6}$ alkyl, $C_{1-6}$ alkoxy, $C_{1-6}$ haloalkyl, amino, $C_{1-4}$ mono or $C_{2-8}$ di-alkyl amino, $C_{1-4}$ mono or $C_{2-8}$ di-acyl amino, S(O)$_q C_{1-6}$ alkyl, $C_{0-6}$ alkylC(O)$C_{1-6}$ alkyl or $C_{0-6}$ alkylC(O)NC$_{0-6}$ alkyl$C_{0-6}$ alkyl, $C_{0-6}$ alkylC(O)$C_{1-6}$ heteroalkyl, with the proviso that the atom linked directly to the carbonyl in —NR$^3$C(O)— is not an oxygen or a sulfur atom; and b) a $C_{0-8}$ alkyl-heterocycle wherein the heterocyclyl group has 5 or 6 members and comprises at least one heteroatom selected from O, N, and S, and said heterocycle is optionally substituted by one, two or three groups independently selected from halogen, hydroxyl, $C_{1-6}$ alkyl, $C_{1-6}$ alkoxy, $C_{1-6}$ haloalkyl, amino, $C_{1-4}$ mono and $C_{2-8}$ di-alkyl amino, $C_{1-4}$ mono or $C_{2-8}$ di-acyl amino, S(O)$_q C_{1-6}$ alkyl, $C_{0-6}$ alkylC(O)$C_{1-6}$ alkyl, $C_{0-6}$ alkylC(O) N$C_{0-6}$ alkyl $C_{0-6}$ alkyl or $C_{0-6}$ alkylC(O)$C_{0-6}$ heteroalkyl.

25. A compound of formula (I) according to claim 1, wherein J represents:

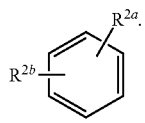

26. A compound of formula (I) according to claim 1, wherein said compound is:

N-(4-(4-(3-(1-(4-aminophenyl)-3-tert-butyl-1H-pyrazol-5-yl)ureido)naphthalen-1-yloxy)pyridin-2-yl)-2-methoxyacetamide;

N-(4-(4-(3-(3-tert-butyl-1-(4-(methylsulfonamido)phenyl)-1H-pyrazol-5-yl)ureido)naphthalen-1-yloxy)pyridin-2-yl)-2-methoxyacetamide;

N-(4-((4-(3-(3-tert-butyl-1-(4-methoxyphenyl)-1H-pyrazol-5-yl)ureido)naphthalen-1-yl)oxy) pyridin-2-yl)-2-methoxyacetamide;

N-(4-(4-(3-(3-tert-butyl-1-(4-methoxyphenyl)-1H-pyrazol-5-yl)ureido)naphthalen-1-yloxy) pyridin-2-yl)-2-hydroxyacetamide;
N-(4-((4-(3-(3-tert-butyl-1-(4-hydroxyphenyl)-1H-pyrazol-5-yl)ureido)naphthalen-1-yl)oxy) pyridin-2-yl)-2-methoxyacetamide;
1-(3-tert-butyl-1-(4-methoxyphenyl)-1H-pyrazol-5-yl)-3-(4-(2-(3-cyclopropylureido)pyridin-4-yloxy)naphthalen-1-yl)urea;
3-(4-(4-(3-(3-tert-butyl-1-(4-methoxyphenyl)-1H-pyrazol-5-yl)ureido)naphthalen-1-yloxy) pyridin-2-yl)-1,1-dimethylurea;
N-(4-(4-(3-(3-tert-butyl-1-(4-methoxyphenyl)-1H-pyrazol-5-yl)ureido)naphthalen-1-yloxy) pyridin-2-yl)pyrrolidine-1-carboxamide;
N-(4-((4-(3-(3-tert-butyl-1-(4-methoxyphenyl)-1H-pyrazol-5-yl)ureido)naphthalen-1-yl)oxy) pyridin-2-yl)morpholine-4-carboxamide;
N-(4-(4-(3-(3-tert-butyl-1-(4-methoxyphenyl)-1H-pyrazol-5-yl)ureido)naphthalen-1-yloxy) pyridin-2-yl)-4-methylpiperazine-1-carboxamide;
N-(4-(4-(3-(3-tert-butyl-1-(3,4-dimethoxyphenyl)-1H-pyrazol-5-yl)ureido)naphthalen-1-yloxy) pyridin-2-yl)-2-methoxyacetamide;
N-(4-((4-(3-(3-tert-butyl-1-(3-chloro-4-hydroxyphenyl)-1H-pyrazol-5-yl)ureido)naphthalen-1-yl)oxy)pyridin-2-yl)morpholine-4-carboxamide;
N-(4-(4-(3-(3-tert-butyl-1-(3-chloro-4-(hydroxymethyl) phenyl)-1H-pyrazol-5-yl)ureido) naphthalen-1-yloxy) pyridin-2-yl)-2-methoxyacetamide;
N-(4-(4-(3-(3-tert-butyl-1-(4-(methylthio)phenyl)-1H-pyrazol-5-yl)ureido)naphthalen-1-yloxy) pyridin-2-yl) pyrrolidine-1-carboxamide;
3-(4-(4-(3-(3-tert-butyl-1-(4-(methylsulfonyl)phenyl)-1H-pyrazol-5-yl)ureido)naphthalen-1-yloxy)pyridin-2-yl)-1,1-dimethylurea;
N-(4-(4-(3-(3-tert-butyl-1-(6-methoxypyridin-3-yl)-1H-pyrazol-5-yl)ureido)naphthalen-1-yloxy) pyridin-2-yl)-2-methoxyacetamide;
N-(4-(4-(3-(3-tert-butyl-1-(6-hydroxypyridin-3-yl)-1H-pyrazol-5-yl)ureido)naphthalen-1-yloxy) pyridin-2-yl)-2-methoxyacetamide;
N-(4-(4-(3-(3-tert-butyl-1-(4-methylthiophen-2-yl)-1H-pyrazol-5-yl)ureido)naphthalen-1-yloxy) pyridin-2-yl)-2-methoxyacetamide;
N-(4-((4-(3-(1,3-diphenyl-1H-pyrazol-5-yl)ureido)naphthalen-1-yl)oxy)pyridin-2-yl)-2-methoxy acetamide;
2-methoxy-N-(4-(4-(3-(3-(4-methyltetrahydro-2H-pyran-4-yl)-1-p-tolyl-1H-pyrazol-5-yl)ureido) naphthalen-1-yloxy)pyridin-2-yl)acetamide;
N-(4-(4-(3-(3-tert-butyl-1-p-tolyl-1H-pyrazol-5-yl)ureido)naphthalen-1-ylthio)pyridin-2-yl)-2-methoxyacetamide;
N-(4-(4-(3-(3-tert-butyl-1-p-tolyl-1H-pyrazol-5-yl)ureido)-1-naphthoyl)pyridin-2-yl)-2-(2-methoxyethoxy) acetamide;
1-(3-tert-butyl)-1-p-tolyl-1H-pyrazol-5-yl)-3-(4-((2-(3-ethylureido)pyridin-4-yl)methyl) naphthalen-1-yl)urea;
N-(4-((4-(3-(3-cyclopropyl-1-p-tolyl-1H-pyrazol-5-yl) ureido)naphthalen-1-yl)oxy)pyridin-2-yl)-2-methoxyacetamide;
2-methoxy-N-(4-(4-(3-(3-(1-methylcyclopropyl)-1-p-tolyl-1H-pyrazol-5-yl)ureido)naphthalen-1-yloxy)pyridin-2-yl)acetamide;
2-methoxy-N-(4-(4-(3-(3-(1-methylcyclohexyl)-1-p-tolyl-1H-pyrazol-5-yl)ureido)naphthalen-1-yloxy)pyridin-2-yl)acetamide;
N-(4-(4-(3-(3-(adamantan-1-yl)-1-p-tolyl-1H-pyrazol-5-yl)ureido)naphthalen-1-yloxy)pyridin-2-yl)-2-methoxyacetamide;
2-methoxy-N-(4-(4-(3-(3-(tetrahydro-2H-pyran-4-yl)-1-p-tolyl-1H-pyrazol-5-yl)ureido) naphthalen-1-yloxy) pyridin-2-yl)acetamide;
2-methoxy-N-(4-(4-(3-(1-p-tolyl-3-(trifluoromethyl)-1H-pyrazol-5-yl)ureido)naphthalen-1-yloxy) pyridin-2-yl) acetamide;
2-methoxy-N-(4-(4-(3-(3-(perfluoroethyl)-1-p-tolyl-1H-pyrazol-5-yl)ureido)naphthalen-1-yloxy) pyridin-2-yl) acetamide;
N-(4-(4-(3-(3-tert-butyl-1-(4-((N-methylsulfamoyl)methyl)phenyl)-1H-pyrazol-5-yl)ureido) naphthalen-1-yloxy)pyridin-2-yl)-2-methoxyacetamide;
N-(4-(4-(3-(3-tert-butyl-1-(3-hydroxyphenyl)-1H-pyrazol-5-yl)ureido)naphthalen-1-yloxy) pyridin-2-yl)-2-methoxyacetamide;
1-(3-tert-butyl-1-(4-hydroxyphenyl)-1H-pyrazol-5-yl)-3-(4-(2-(3-methylureido)pyridin-4-yloxy) naphthalen-1-yl)urea;
3-(4-(4-(3-(3-tert-butyl-1-(4-hydroxyphenyl)-1H-pyrazol-5-yl)ureido)naphthalen-1-yloxy) pyridin-2-yl)-1,1-dimethylurea;
N-(4-(4-(3-(3-tert-butyl-1-(4-hydroxyphenyl)-1H-pyrazol-5-yl)ureido)naphthalen-1-yloxy) pyridin-2-yl)pyrrolidine-1-carboxamide;
N-(4-(4-(3-(3-tert-butyl-1-(3-methoxyphenyl)-1H-pyrazol-5-yl)ureido)naphthalen-1-yloxy) pyridin-2-yl)-2-methoxyacetamide;
1-(4-(4-(3-(3-tert-butyl-1-(4-methoxyphenyl)-1H-pyrazol-5-yl)ureido)naphthalen-1-yloxy) pyridin-2-yl)-3-methylurea;
N-(4-(4-(3-(3-tert-butyl-1-(6-methoxypyridin-3-yl)-1H-pyrazol-5-yl)ureido)naphthalen-1-yloxy) pyridin-2-yl) morpholine-4-carboxamide;
N-(4-(4-(3-(3-tert-butyl-1-(4-(trifluoromethoxy)phenyl)-1H-pyrazol-5-yl)ureido)naphthalen-1-yloxy)pyridin-2-yl)-2-methoxyacetamide;
N-(4-(4-(3-(3-tert-butyl-1-(4-chlorophenyl)-1H-pyrazol-5-yl)ureido)naphthalen-1-yloxy)pyridin-2-yl)-2-methoxyacetamide;
Methyl-4-(3-tert-butyl-5-(3-(4-((2-(2-methoxyacetamido)pyridin-4-yl)oxy)naphthalen-1-yl) ureido)-1H-pyrazol-1-yl)benzoate;
N-(4-(4-(3-(3-tert-butyl-1-(4-(methylthio)phenyl)-1H-pyrazol-5-yl)ureido)naphthalen-1-yloxy)pyridin-2-yl)-2-methoxyacetamide;
1-(3-tert-butyl-1-(4-(methylsulfonyl)phenyl)-1H-pyrazol-5-yl)-3-(4-((2-ureidopyridin-4-yl)oxy) naphthalen-1-yl)urea;
1-(3-tert-butyl-1-(4-(methylsulfonyl)phenyl)-1H-pyrazol-5-yl)-3-(4-((2-(3-methylureido)pyridin-4-yl)oxy)naphthalen-1-yl)urea;
1-(3-tert-butyl-1-(4-(methylsulfonyl)phenyl)-1H-pyrazol-5-yl)-3-(4-(2-(3-cyclopropylureido) pyridin-4-yloxy) naphthalen-1-yl)urea;
N-(4-(4-(3-(3-tert-butyl-1-(4-(methylsulfonyl)phenyl)-1H-pyrazol-5-yl)ureido)naphthalen-1-yloxy)pyridin-2-yl)-4-methylpiperazine-1-carboxamide;
N-(4-(4-(3-(3-tert-butyl-1-(4-(methylsulfonyl)phenyl)-1H-pyrazol-5-yl)ureido)naphthalen-1-yloxy)pyridin-2-yl)morpholine-4-carboxamide;
N-(6-(4-(3-(3-tert-butyl-1-(4-(methylsulfonyl)phenyl)-1H-pyrazol-5-yl)ureido)naphthalen-1-yloxy)pyrimidin-4-yl)-2-methoxyacetamide;

N-(4-(4-(3-(3-tert-butyl-1-(4-(hydroxymethyl)-3-methoxyphenyl)-1H-pyrazol-5-yl)ureido) naphthalen-1-yloxy)pyridin-2-yl)-2-methoxyacetamide;

N-(4-(4-(3-(3-tert-butyl-1-(3-chloro-4-hydroxyphenyl)-1H-pyrazol-5-yl)ureido)naphthalen-1-yloxy)pyridin-2-yl)-2-methoxyacetamide;

N-(4-(4-(3-(3-tert-butyl-1-(3,5-dimethoxyphenyl)-1H-pyrazol-5-yl)ureido)naphthalen-1-yloxy) pyridin-2-yl)-2-methoxyacetamide;

N-(4-(4-(3-(3-tert-butyl-1-(3-chloro-4-methoxyphenyl)-1H-pyrazol-5-yl)ureido)naphthalen-1-yloxy)pyridin-2-yl)-2-methoxyacetamide;

N-(4-(4-(3-(3-tert-butyl-1-(3,4-dichlorophenyl)-1H-pyrazol-5-yl)ureido)naphthalen-1-yloxy) pyridin-2-yl)-2-methoxyacetamide;

N-(4-(4-(3-(3-tert-butyl-1-(thiophen-2-yl)-1H-pyrazol-5-yl)ureido)naphthalen-1-yloxy)pyridin-2-yl)-2-methoxyacetamide;

N-(4-(4-(3-(3-tert-butyl-1-(6-methylpyridin-3-yl)-1H-pyrazol-5-yl)ureido)naphthalen-1-yloxy) pyridin-2-yl)-2-methoxyacetamide;

N-(4-((4-(3-(3-tert-butyl-1-p-tolyl-1H-pyrazol-5-yl)ureido)naphthalen-1-yl)methyl)pyridin-2-yl)-2-methoxyacetamide;

N-(4-((4-(3-(3-tert-butyl-1-p-tolyl-1H-pyrazol-5-yl)ureido)naphthalen-1-yl)methyl)pyridin-2-yl)-2-(2-methoxyethoxy)acetamide;

N-(4-(4-(3-(3-tert-butyl-1-p-tolyl-1H-pyrazol-5-yl)ureido)-1-naphthoyl)pyridin-2-yl)-2-methoxy acetamide; or 1-(3-tert-butyl-1-p-tolyl-1H-pyrazol-5-yl)-3-(4-(2-(3-ethylureido)isonicotinoyl)naphthalen-1-yl) urea;

or a pharmaceutically acceptable salt of any one thereof, including all stereoisomers, tautomers and isotopic derivatives thereof.

27. A pharmaceutical composition comprising a compound according to claim 1, in combination with one or more pharmaceutically acceptable diluents or carriers.

28. A compound of claim 1 wherein:

J represents

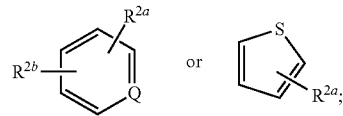

$R^{2a}$ is H, OH, halo, —$C_{1-6}$ alkoxy, —$SC_{1-6}$ alkyl, —$SO_2C_{1-6}$ alkyl, —$OCF_3$, —NR'R" where R' is H, —$C_{1-3}$ alkyl or —$SO_2C_{1-3}$ alkyl and R" is H or —$C_{1-3}$ alkyl, —$NHSO_2CH_3$;

$R^{2b}$ is H, halo, or $C_{1-6}$ alkoxy; and at least one of $R^{2a}$ and $R^{2b}$ is not hydrogen.

* * * * *